(12) United States Patent
Blaha et al.

(10) Patent No.: US 12,161,410 B2
(45) Date of Patent: Dec. 10, 2024

(54) SYSTEMS AND METHODS FOR VISION ASSESSMENT

(71) Applicant: Vivid Vision, Inc., San Francisco, CA (US)

(72) Inventors: James J. Blaha, San Francisco, CA (US); Benjamin T. Backus, Oakland, CA (US); Manish Z. Gupta, San Francisco, CA (US)

(73) Assignee: Vivid Vision, Inc., San Francisco, CA (US)

( * ) Notice: Subject to any disclaimer, the term of this patent is extended or adjusted under 35 U.S.C. 154(b) by 0 days.

(21) Appl. No.: 18/463,371

(22) Filed: Sep. 8, 2023

(65) Prior Publication Data

US 2024/0099575 A1  Mar. 28, 2024

Related U.S. Application Data

(63) Continuation of application No. 16/191,324, filed on Nov. 14, 2018, now abandoned.
(Continued)

(51) Int. Cl.
*A61B 3/024* (2006.01)
*A61B 3/00* (2006.01)
(Continued)

(52) U.S. Cl.
CPC ............ *A61B 3/024* (2013.01); *A61B 3/0025* (2013.01); *A61B 3/0033* (2013.01);
(Continued)

(58) Field of Classification Search
CPC ......... A61B 3/024; A61B 3/025; A61B 3/033; A61B 3/041; A61B 3/091; A61B 3/113;
(Continued)

(56) References Cited

U.S. PATENT DOCUMENTS

| | | |
|---|---|---|
| 4,995,717 A | 2/1991 | Damato |
| 5,880,812 A | 3/1999 | Solomon |

(Continued)

FOREIGN PATENT DOCUMENTS

| | | |
|---|---|---|
| CN | 107224261 A | 10/2017 |
| EP | 23 12994 B1 | 1/2021 |

(Continued)

OTHER PUBLICATIONS

Aderman et al. (Jun. 2015) "Dichoptic Virtual Reality Therapy for Amblyopia in Adults", Investigative Ophthalmology & Visual Science, 56(7):2191.

(Continued)

*Primary Examiner* — Travis S Fissel
(74) *Attorney, Agent, or Firm* — Mintz, Levin, Cohn, Ferris, Glovsky and Popeo, P.C.

(57) ABSTRACT

Methods and systems for assessing a visual field of a person are provided. Information can be presented to a person undergoing a visual field testing in a manner that utilizes the person's natural tendency to look at an object that is displayed so that it attracts the person's attention. A fixation target can be displayed on a display viewed by a user. Once it is determined that the user has viewed the fixation target and the person's eye(s) location is determined, a test target is displayed on the display in a location corresponding to a location on the user's visual field. The test target is determined to be either detected or missed based on user input acquired as the user is viewing the display.

20 Claims, 32 Drawing Sheets

Related U.S. Application Data

(60) Provisional application No. 62/586,151, filed on Nov. 14, 2017.

(51) Int. Cl.
*A61B 3/113* (2006.01)
*G06F 3/01* (2006.01)
*G06F 3/02* (2006.01)

(52) U.S. Cl.
CPC .......... *A61B 3/0041* (2013.01); *A61B 3/0091* (2013.01); *A61B 3/113* (2013.01); *G06F 3/012* (2013.01); *G06F 3/013* (2013.01); *G06F 3/02* (2013.01)

(58) Field of Classification Search
CPC .. A61B 3/028; A61B 3/08; A61B 3/09; G06F 3/012; G06F 3/013; G06F 3/02
USPC ........ 351/201, 205, 206, 211, 222–225, 245, 351/246
See application file for complete search history.

(56) References Cited

U.S. PATENT DOCUMENTS

| | | |
|---|---|---|
| 5,910,834 A | 6/1999 | Mcclure et al. |
| 6,290,357 B1 | 9/2001 | Massengill et al. |
| 7,681,130 B1 | 3/2010 | Lavallee et al. |
| 8,057,036 B2 | 11/2011 | Hess et al. |
| 8,066,372 B2 | 11/2011 | Cooperstock et al. |
| 8,454,166 B2 | 6/2013 | Fateh |
| 9,706,910 B1 | 7/2017 | Blaha et al. |
| 2002/0047987 A1 | 4/2002 | Massengill et al. |
| 2004/0100617 A1 | 5/2004 | Abitbol |
| 2005/0105051 A1 | 5/2005 | Jones et al. |
| 2006/0087618 A1 | 4/2006 | Smart et al. |
| 2009/0091706 A1 | 4/2009 | Derr |
| 2010/0073469 A1 | 3/2010 | Fateh |
| 2010/0086221 A1 | 4/2010 | Stankiewicz et al. |
| 2010/0207877 A1 | 8/2010 | Woodard |
| 2010/0216104 A1 | 8/2010 | Reichow et al. |
| 2010/0283969 A1 | 11/2010 | Cooperstock et al. |
| 2012/0069002 A1 | 3/2012 | Kuribayashi et al. |
| 2013/0155376 A1 | 6/2013 | Huang et al. |
| 2013/0171596 A1 | 7/2013 | French |
| 2013/0308099 A1 | 11/2013 | Stack |
| 2014/0028678 A1 | 1/2014 | Chmielewski et al. |
| 2014/0107429 A1 | 4/2014 | Simkovich et al. |
| 2014/0214502 A1 | 7/2014 | Bahl et al. |
| 2014/0276130 A1 | 9/2014 | Mirelman et al. |
| 2014/0306866 A1 | 10/2014 | Miller et al. |
| 2014/0340639 A1 | 11/2014 | Rust |
| 2014/0340642 A1 | 11/2014 | You et al. |
| 2014/0347390 A1 | 11/2014 | Poulos et al. |
| 2015/0029322 A1 | 1/2015 | Ragland et al. |
| 2015/0140529 A1 | 5/2015 | Tinjust |
| 2015/0338915 A1 | 11/2015 | Publicover et al. |
| 2016/0161767 A1 | 6/2016 | Childers |
| 2017/0049316 A1 | 2/2017 | Donaldson |
| 2017/0273552 A1 | 9/2017 | Leung et al. |
| 2017/0340200 A1 | 11/2017 | Blaha et al. |
| 2019/0046029 A1 | 2/2019 | Tomasi et al. |
| 2019/0150727 A1 | 5/2019 | Blaha et al. |
| 2019/0365594 A1 | 12/2019 | Geisinger et al. |
| 2020/0329961 A1 | 10/2020 | Oz et al. |
| 2021/0076930 A1 | 3/2021 | Blaha et al. |
| 2021/0290053 A1 | 9/2021 | Tran et al. |
| 2023/0380679 A1 | 11/2023 | Backus et al. |

FOREIGN PATENT DOCUMENTS

| | | |
|---|---|---|
| JP | 2011161122 A | 8/2011 |
| JP | 2017529964 A | 10/2017 |
| WO | 2014182977 A1 | 11/2014 |
| WO | 2016051136 A1 | 4/2016 |
| WO | 2017143091 A1 | 8/2017 |
| WO | 2017182596 A1 | 10/2017 |

OTHER PUBLICATIONS

Backus, Benjamin T. (Sep. 2011) "Recruitment of New Visual Cues for Perceptual Appearance", Sensory Cue Integration, Computational Neuroscience Series, 101-119.

Bettin et al. (2013) "Glaucoma: Present Challenges and Future Trends", Ophthalmic Research, 50(4):197-208.

Blaha et al. (Mar. 2014) "Diplopia: A Virtual Reality Game Designed to Help Amblyopics", Virtual Reality (VR), IEEE, 163-164.

Bonnen et al. (Mar. 2015) "Continuous Psychophysics: Target-Tracking to Measure Visual Sensitivity", Journal of Vision, 15(3):14 ( 16 pages).

Cooper (2007) "Computerized Vision Therapy for Home and Office Treatment of Accommodative and Vergence Disorders, and Amblyopia", Journal of Behavioral Optometry, 18(4):88-93.

Damato, B. E. (1985) "Oculokinetic Perimetry: A Simple Visual Field Test for Use in the Community", British Journal of Ophthalmology, 69(12):927-931.

Friedman et al. (2004) "Prevalence of Open-Angle Glaucoma Among Adults in the United States", Archives of Ophthalmology, 122(4):532-538.

Godinez (Oct. 2020) "Cue Scaffolding to Train Stereo-Anomalous Observers to Rely on Disparity Cues", Journal of Vision, 20(11):300.

Hess et al. (Feb. 2012) "An iPOD Treatment of Amblyopia: An Updated Binocular Approach", Optometry, 83 (2):87-94.

Law et al. (Sep. 2011) "Improvement in Stereoacuity through Training with Correlated Cues", Journal of Vision, 11(11):1016-1016.

Manor (2003) "Defining the Temporal Threshold for Ocular Fixation in Free-Viewing Visuocognitive Tasks", Journal of Neuroscience Methods, 128(1-2):85-93.

Matsumoto et al. (2016) "Visual Field Testing with Head-Mounted Perimeter 'imo'", PloS One, 11(8):e0161974 (12 pages).

McPeek et al. (1999) "Saccades Require Focal Attention and Are Facilitated by a Short-Term Memory System.", Vision Research, 39(8):1555-1566.

Morales et al. (2000) "Comparison Between Tendency-Oriented Perimetry (TOP) and Octopus Threshold Perimetry", Ophthalmology, 107(1):134-142.

Mutlukan et al. (1993) "Clinical Evaluation of A Multi-Fixation Campimeter for The Detection of Glaucomatous Visual Field Loss", British Journal of Ophthalmology, 77(6):332-338.

Mutlukan et al. (1992) "The Dark Perimetric Stimulus", The British Journal of Ophthalmology, 76(5):264-267.

Nordqvist, Joseph (Apr. 23, 2013) "Tetris Video Game Helps Treat Lazy Eye", Medical News Today. MediLexicon, Intl., 3 pages.

Qui et al. (2014) "Association Between Visual Field Defects and Quality of Life in the United States", Ophthalmology, 121(3):733-740.

Tham et al. (2014) "Global Prevalence of Glaucoma and Projections of Glaucoma Burden through 2040: A Systematic Review and Meta-Analysis", Ophthalmology, 121(11):2081-2090.

Vajaranant (2012) "The Changing Face of Primary Open-Angle Glaucoma in the United States: Demographic and Geographic Changes from 2011 to 2050", American Journal of Ophthalmology, 154(2):303-314.

Waddingham et al. (2006) "Virtual Reality for Interactive Binocular Treatment of Amblyopia", International Journal on Disability and Human Development, 201-208.

Wroblewski et al. (2014) "Testing of Visual Field with Virtual Reality Goggles in Manual and Visual Grasp Modes", BioMed Research International, 10 pages.

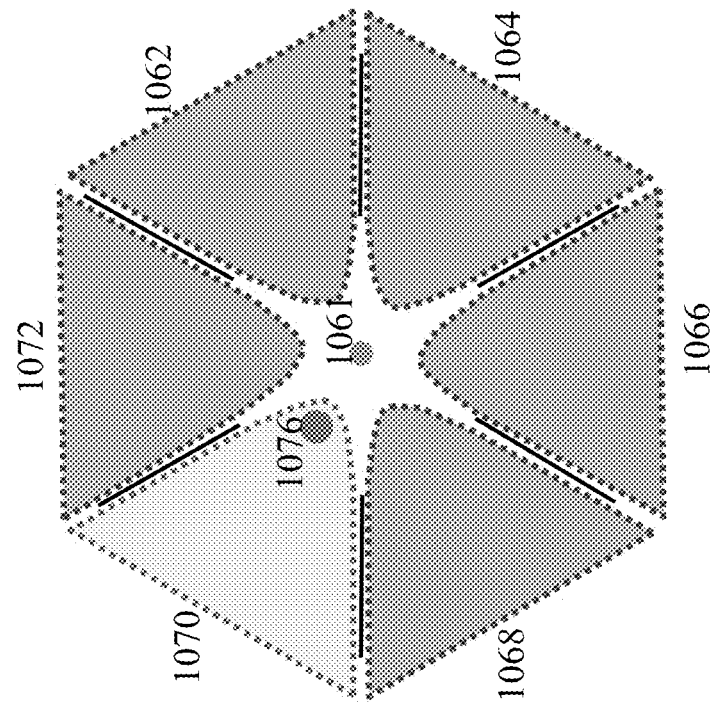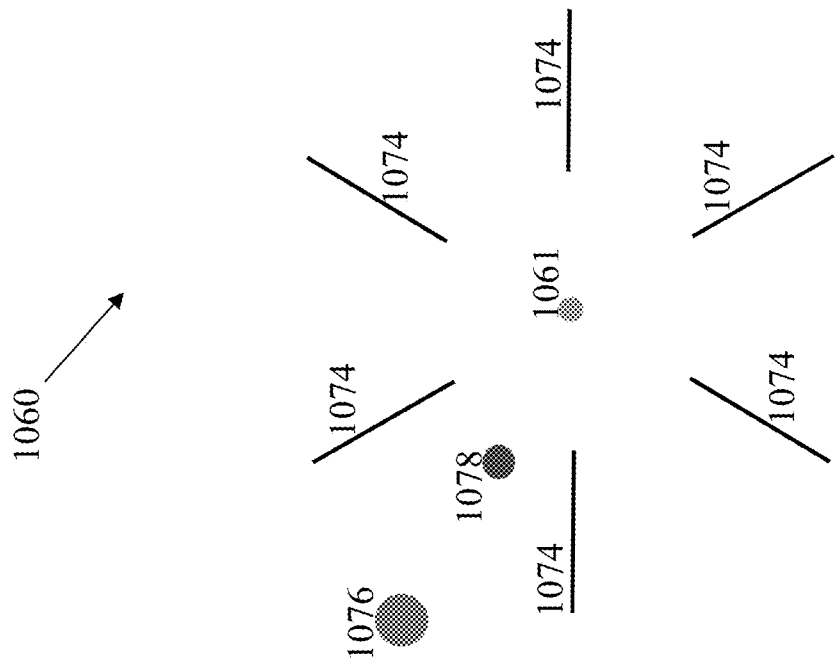
FIG. 10E

SYSTEMS AND METHODS FOR VISION ASSESSMENT

CROSS REFERENCE TO RELATED APPLICATIONS

The present application claims priority to U.S. Patent Application No. 62/586,151, filed Nov. 14, 2017, entitled SYSTEMS AND METHODS FOR VISION ASSESSMENT, the disclosure of which is incorporated herein by reference in its entirety.

TECHNICAL FIELD

Systems and methods for visual field analysis, for diagnosing and monitoring vision disorders including glaucoma, are provided.

BACKGROUND

Many diseases of the visual system first manifest as a selective geographic loss of vision at one or more locations. Screening for disease, monitoring progression during treatment, and developing new treatments depend on a quality assessment of defects in the patient's visual field. A visual field analysis, also referred to as "perimetry," involves measuring how well a patient can see at different locations on her or his retina.

Glaucoma is a progressive disease in which peripheral vision is lost due to damage in retinal ganglion cells, whose axons form the optic nerve. For example, primary open-angle glaucoma (POAG), which is estimated to affect several millions in the United States, can lead to loss of vision if not detected early. Perimetry is typically used for detecting, monitoring disease progression, and evaluating new treatments for POAG and other visual disorders.

Current techniques for perimetry are costly and are often inconvenient to a patient. Therefore, it is difficult to administer a cluster of perimetry tests to a patient within a short window of time, which limits the ability to characterize the patient's vision at that time. Also, a patient typically needs to be instructed to keep his/her head still, which can cause physical discomfort from posture maintenance, and reduces fixation accuracy. Furthermore, individual test results may be less reliable than desired, which compromises the usefulness of the administered tests.

Accordingly, there is a need for improved techniques for analysis of a patient's visual field.

SUMMARY

Methods and systems for assessing and monitoring a visual field of a person are provided. Information can be presented to a person undergoing a visual field testing in a manner that utilizes the person's natural tendency to look at an object that is displayed so that it attracts the person's attention. A fixation target can be displayed on a display viewed by a user. Once it is determined that the user has viewed the fixation target and the person's eye(s) location is determined, a test target is displayed on the display in a location corresponding to a location on the user's visual field, i.e., on the user' retina. Thus, once it is known where the user's eyes are positioned, the test target can be displayed on the display such that the test target is intended to be viewed on a specific location of the patient's retina. The test target is determined to be either detected or missed based on user input acquired as the user is viewing the display. For example, the test target is determined to be detected if a pointer also displayed on the display (which can be controlled by the user in various ways) is moving towards the location of the test target. However, if the pointer is moving in a direction different from that of the test target, or if the pointer is not moving and a certain amount of time has elapsed, the test target can be determined to be missed. Multiple test targets can be displayed in this way in different locations, such that multiple locations on the user's retina are tested. The assessment can be used for testing the patient's visual field, for monitoring progression of a disease, monitoring progression of a treatment, and for any other purposes.

In one aspect, a system for assessment of a visual field of a user is provided, the system including computing hardware configured to perform various operations. The operations include displaying, on the virtual reality environment on a virtual reality display of a head-mountable virtual reality device, a fixation target, the virtual reality environment comprising a pointer that is controlled by the user wearing the head-mountable virtual reality device. For example, in various embodiments a virtual reality environment may be any visual stimulus displayed to the user that is processed and simulated on a computer and displayed to the user based, at least in part, on the user's head position. This includes head-mounted or off-head displays, displays commonly referred to as augmented reality or mixed reality, and computer monitors configured to track the movement of the head and update the image to create a window-like effect. The operations further include determining whether at least one eye of the user is fixating on the fixation target, when it is determined that the eye is fixating on the fixation target, displaying a test target of a plurality of test targets in a first location on the virtual reality environment, the first location corresponding to a first location of the visual field of the user, receiving user input comprising indication of movement of the pointer in the virtual reality environment and determining whether the user input indicates that the pointer is moving towards the first location, and acquiring, based on the received user input, an indication of whether the test target has been detected by the user, and storing the indication. The operations further include iteratively performing the displaying, determining, displaying, receiving, and acquiring until all test targets of the plurality of test targets have been displayed, and providing assessment of a condition of the visual field based on results of the determination of the detection by the user of the test targets during the iterative performance of the displaying, determining, displaying, receiving, and acquiring steps.

The details of one or more variations of the subject matter described herein are set forth in the accompanying drawings and the description below. Other features and advantages of the subject matter described herein will be apparent from the description and drawings, and from the claims.

BRIEF DESCRIPTION OF DRAWINGS

The present disclosure will be more fully understood from the following detailed description taken in conjunction with the accompanying drawings, in which:

FIG. 10E illustrates a test for which a patient may respond by specifying one of six possible sectors for the location of a test target;

DETAILED DESCRIPTION

Figure 1A:
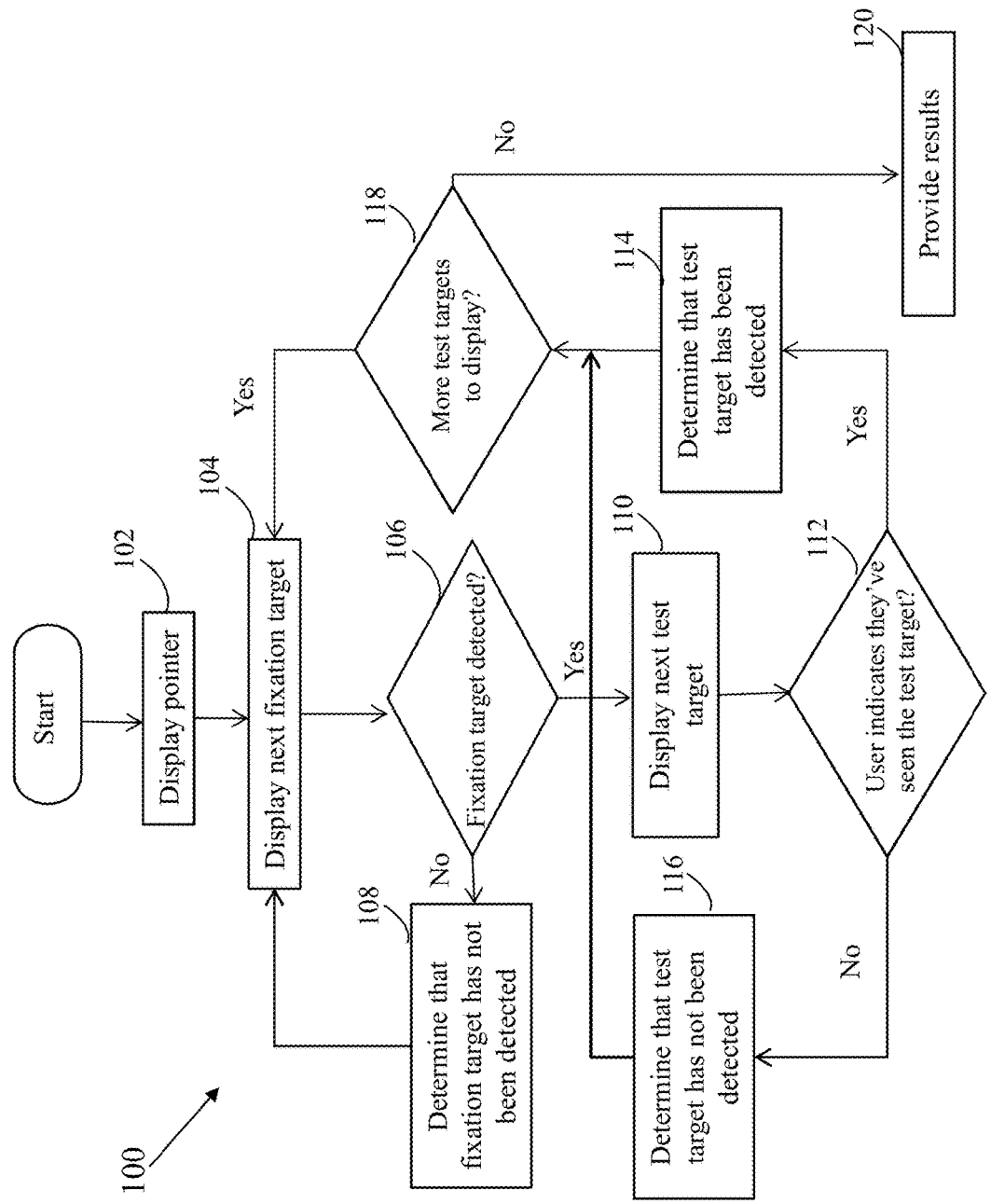
FIG. 1A is a flowchart illustrating a process of administering a test to a patient to assess the patient's visual field, in accordance with some embodiments.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used. Like reference symbols in the various drawings indicate like elements.

In certain embodiments, methods and devices are provided for diagnosis and monitoring patients' visual disorders, including disorders affecting a visual field of a patient. In an exemplary embodiment, the methods and devices are used in head-mountable virtual reality devices that provide a visual reality environment on their virtual reality displays. However, the methods and devices can be utilized in any other devices with similar environments, such as augmented reality or mixed reality environments in a mobile computing device or other computing device(s). Therefore, it is to be understood that the systems and methods described herein apply to virtual reality, augmented, reality, mixed reality, or similar environments. The patient's visual field can be assessed by displaying images to the patient at various locations in the patient's visual field and determining which locations are blind spots or have reduced sensitivity. Thus, it can be detected that the patient does not see an image displayed on the display viewed by the patient at the location corresponding to a blind spot or retinal area of decreased function. The images are presented to patients in a manner that exploits natural propensity of people to look at an object that attracts their attention.

In one exemplary embodiment, a head-mountable virtual reality device has computing hardware configured to perform operations for analyzing a patient's visual field. The analysis (which can include either or both diagnosis and monitoring of a treatment) can be performed in an automated manner and in the way that is comfortable to the patient. Moreover, the head-mountable virtual reality device can be used to perform the analysis in a cost-saving manner. Various diseases, such as, for example, glaucoma, brain tumor, stroke, intraocular cancer, and detached retina, as well as routine eye care check-ups, can be addressed using a high quality visual field test which can be performed in a relatively short time period. For example, in some embodiments, the analysis can be performed in 5 minutes or less, though it should be appreciated that other time periods can be required depending on various factors, including the desired statistical confidence, the amount of time the patient has to take the test, visual fatigue, and the purpose of the test (e.g. for screening vs monitoring).

A traditional set-up for perimetry is somewhat cumbersome. For example, a patient is required to maintain visual fixation or gaze point on a target that can be disposed centrally on a display. The patient is required to keep his/her eyes still throughout the examination by gazing steadily at the central object (target) while test targets are presented, which can be referred to as a stationary-eye perimetry. However, many patients, particularly elder patients and children, are unable to comply with this requirement, even if they have normal vision, because they tend to look away from the central target, towards a new salient target or test target (foveation reflex). The traditional techniques do not account for covert visual attention and certain eye movements. Covert attention, which is the attention deployed to a location without accompanying eye movements, acts like a gain field that modulates how well the brain can detect a target at a given location, independent of where the eyes are pointed. A lack of covert attention to any part of the visual field reduces behaviorally measured visual sensitivity at that location. The effort to maintain fixation on a single central target over time can require covert attention to the fixation target. Thus, patients can fail to detect visual targets presented at other locations in the display, which they otherwise would have detected, if their covert attention is allocated to the wrong location. Another complication can be than patients with cataract can see flashes from scattered light in the eye, even though they may not see the actual target location. The techniques in accordance with the present disclosure, however, allow patients to move their eyes off of a single fixation target.

Another disadvantage associated with the traditional perimetry is that it is typically unnatural for patients not to make eye movements and to keep their eyes on a certain target. Thus, even if initially a patient can accurately fixate his/her eyes on a target, the fixation becomes challenging as the test progresses and the patient is required to keep gazing at the same target. The test can be restarted if it is determined that the patient does not properly fixate on the central target. In some cases, test results may need to be discarded when rates of fixation errors are determined to be high. The techniques in accordance with the present disclosure allow patients to change fixation from one target to another, which makes it unnecessary for them to practice fixating or start over.

Furthermore, because existing systems accept a "yes/no," or another type of a binary user input during a test, it may be easier for a patient to "cheat" by guessing whether or not a target was displayed. Patients often guess when test targets appear, and, although a medical professional supervising the test may be able to take actions to compensate for such guessing, such actions nevertheless lengthen the testing and increase the cost to administer the test. Also, the accuracy of the testing can be generally compromised when there is likelihood that a patient can guess an input. A further advantage of the described approach is that there is less room for patients to provide incorrect input, such as by guessing a correct answer. In particular, the described techniques reduce a number of false positives because the chance of guessing a correct location can be an order of magnitude smaller than the chance of guessing that a target has been presented.

In addition, conventional campimetry techniques, such as standard automated perimetry (SAP), for examining and assessing a person's visual field, can have certain limitations, which may prevent some patients from positioning their head at the correct location. For example, patients that are bedridden or confined to a wheelchair may not be able to maintain their head at the correct position for both conventional campimetry and standard automated perimetry.

In some embodiments, a pointer (e.g., an image of a relatively small object) can be displayed on a display of a device, such as a virtual reality (VR) display of a head-mountable virtual reality device or a display of a computing device, and the pointer is controllable based on user input. Thus, when the display is a display of a head-mountable virtual reality device, the pointer ("head pointer") will move as the patient wearing the head-mountable device moves his/her head. In this way, movements of the patient's head operate as user input—the patient "points" at objects displayed on the display by movement his/her head towards the objects, which can be displayed at various locations within the patient's field of view on the display. The position of the head pointer changes as the user's head moves, but the pointer itself can remain in the same position relative to the patient (e.g., in the center of the user's field of view). In various embodiments, the patient holds a rotationally and/or a positionally tracked hand controller that is used as a pointer to provide input to the test in much the same way as the head pointer does.

A patient's field of view can be divided into detection zones such that each zone corresponds to a spot in the patient's visual field. When a head-mountable virtual reality device presents a VR environment on the device's VR display, test targets appear (e.g., in the patient's peripheral vision) and the patient can react to each target, if that target was seen by the patient, by turning the patient's head toward the target and thus moving the pointer. The target, which can have various characteristics (as discussed in more detail below), is intended to attract the patient's attention, such that a natural tendency of a person to look towards a new image on the display is utilized. The test target has a detection zone associated therewith, and the target is displayed within that zone. When the pointer is moved in the correct direction, towards the location of the test target (which may no longer be visible, since it was displayed for a brief period of time (e.g., 0.3 seconds)) and it is determined that the test target is detected, a subsequent fixation target can appear on the display. The fixation target can be displayed in the vicinity of the detection zone associated with the test target, or, in some embodiments, within the detection zone. Furthermore, in some embodiments, the fixation target can be in the form of a movable object. The movement can be linear, a random walk, quick jumps, or in the form any pattern(s), or a combination thereof. Also, the fixation target can be displayed in the form of a representation of an object or a person that is moving as part of a 2D or 3D scene, such as a game-like or movie-like scene is displayed. Such representation can be seen by the patient as being "chased" by the pointer, which can also be in the form of a representation of any suitable object. In some implementations, the fixation target can be (e.g., moving) part of a scene that resembles a real world. Also, the fixation target can be displayed as part of a real movie or a video clip.

Regardless of its specific format and whether and in which way it can move, the fixation target is intended to be looked at by the patient before the patient moves his/head (or another body part or an input device held by the user) towards the location where the test target was displayed. As the pointer at least partially overlaps the fixation target (or "collides" with it), the fixation target is determined to be seen by the user, and the position of the user's eye(s) is thus determined. Once the position of the user's eyes is determined, a subsequent test target is displayed at a location corresponding to a location in the patient's visual field. In some embodiments, for the fixation target determined to be detected, the pointer is required to remain in the vicinity of the fixation target for certain duration. Once the pointer is disposed at a predetermined distance within the fixation target (e.g., overlaps with the target), a subsequent test target is displayed in another location on the display (if there are more test targets to display in a current test or session) that is mapped to a corresponding location on the patient's retina, whereas the fixation target disappears. If the patient sees the subsequent test target, the patient moves the pointer towards the location of that subsequent test target, based on the natural tendency of the eyes to turn towards an object that attracted attention. In this way, multiple locations in the patient's visual field can be tested to ultimately provide an overall assessment of the condition of the patient's retina.

The fixation target can be presented to one eye or to both eyes simultaneously. When the fixation target is presented to just one eye, the test target is presented to the same eye. In a person with normal binocular vision, a binocularly visible fixation target provides greater stability of fixation and is preferred for that reason is preferred. However, some people do not fixate binocular targets accurately with both eyes simultaneously. For example, a person with amblyopia or strabismus history may use one eye to fixate, with the other eye not being pointed at its fixation target simultaneously. In that case, a binocular fixation target should not be used, because the location of the test target cannot be determined accurately relative to the visual axis of that eye. The test can include determination, at the start of the test, whether to use binocular fixation targets. For example, a person with strabismus may see targets that were intended for the blind spot when those targets are presented to the eye that does not control fixation. At that point the test can use monocular fixation targets instead.

The system may use a model to estimate the viewer's true fixation. The model could take inputs including, but not limited to head position, head velocity, eye positions, eye velocities, and information about the test target (e.g. the pixels on the screen that changed preceding their estimated fixation). This would allow the system to make a better estimate of the patients fixation during the time the test target is shown, allowing for more accurate placement on a specific part of the retina.

FIG. 1A illustrates one embodiment of a method 100 of testing or assessment a patient's visual field in accordance with the described techniques. The process shown in FIG. 1A can start at any suitable time, upon any suitable trigger. For example, if the patient/user is performing the assessment in a home environment (or otherwise outside a clinical setting), the process can start when the user initiates a system configured to performed the described techniques. The system can be, for example, a computing device (e.g., a smartphone or a personal computer) and a head-mountable VR device. A specific test can be selected by the user or the test can be selected and presented automatically to the user. For example, a specific test can be selected in advance by a clinician. In some cases, the clinician can remotely monitor user's performance of the test in real time, or the clinician can assess the test results after the test has been completed. In some embodiments, selecting a test involves selecting a template and a layout of the template, which are discussed in more detail below. The template can be selected to assess extent of the visual field and sensitivity of the patient's vision in different parts of the visual field. Various parameters of the test can be set up in advance, and/or adjusted in real time, as discussed below in more detail below. In some embodiments, at least some of the parameters can be adjusted in real time, as the test is being administered. Furthermore, in some embodiments, locations of the test targets and fixation targets can be selected dynamically. For example, probabilistic approaches (e.g., a Bayesian approach) can be used.

As shown in FIG. 1A, a pointer (e.g., a head pointer or another type of pointer such as, e.g., a pointer controlled by a hand controller) can be displayed in the patient's field of view, at block 102. At block 104, a next fixation target can then be displayed on a certain background, which is the first fixation when the assessment (testing) begins. The next fixation target can have any suitable properties and it can be displayed in the patient's field of view at a randomly selected or a predetermined location. The position of the head pointer or hand-held pointer can be updated equally with changes in the position of the head or hand that controls the pointer. Alternatively the position of the pointer can be updated with a gain greater than 1.0 to make it easier for the patient to move the pointer quickly. Alternatively the position of the pointer can be updated with a gain less than 1.0 to make it easier for the patient to achieve success in a task at fixation. To smooth the movement of the pointer in the case of tremor or lack of fine motor control in a patient, the position of the pointer can be updated with a delay that allows for integration of the head or hand position over time, or various other algorithms can be used to control the pointer's position relative to the fixation target.

The fixation target is presented with the goal of acquiring input indicating that a fixation task associated with the fixation target is completed. The fixation task can be defined as a task that a patient is required to complete to perform proper fixation on the fixation target. For example, the fixation task can be a task of moving a pointer towards the fixation target such that (in some cases), the pointer at least partially overlaps with the fixation target. The fixation target, which can have any of various properties (e.g., it can be movable in various ways such that it jumps on the display, or it can have various features that can be displayed to cause the patient to look at the fixation target), can be displayed until the patient completes the required fixation task such that the fixation target (and features of the fixation target) are viewed by the patient. In some embodiments, the fixation task performed by the patient includes moving the pointer so that it overlaps at least in part with the fixation target. Thus, as shown in FIG. 1A, at decision block 106, it is determined whether the fixation target has been detected/seen by the patient. The described techniques can require verification that the patient's fovea is fixated on the fixation target. If it is determined, at block 106, that the fixation target was not seen by the patient (e.g., no indication is received (e.g., based on tracking of the patient's head and/or patient's eyes) that the patient has seen that fixation target), the process 100 can follow to block 108 where it is determined that the fixation target has not been detected. The process 100 then returns to block 104, where the fixation target that has not been detected by the patient continues being displayed One or more properties of the fixation target can be changed, with the intent to display the fixation target in a manner more visible to the patient. However, in some implementations, if it is determined that the patient has not seen the displayed fixation target, additional one or more fixation targets can be displayed (at block 104) until an indication is received (e.g., based on tracking of the patient's head and/or patient's eyes) that the patient has seen that fixation target.

Once it is determined, at decision block 106, that the patient has seen the fixation target (or one of more than one such fixation targets), such that the fixation task is deemed completed, the location of the patient's eyes is determined and a next test target (also referred to as "test target" or "stimulus") is displayed, at block 110. The test target can be displayed to one or both eyes of the user. In the beginning of the testing, the next test target is the first test target. The test target can have various properties, as described in more detail below. In some cases, a location in the patient's field of view to display the test target can be selected randomly, and/or from a number of predetermined locations (corresponding to locations on the retina) that are intended to be tested. The test target can be displayed for a certain duration of time, for example, for a duration of time in a range from about 100 milliseconds (ms) to about 300 ms, or for another suitable time period.

The pointer can also have various properties. In at least one implementation, the pointer is in the form of a spot (e.g., in one example, of about 0.8 degrees in diameter, though it can have any suitable size and shape) which moves with the head of the patient, is controlled by a hand-held controller or another user input device.

In some embodiments, once the fixation task is determined to have been completed, the test target can be displayed (at block 110) for a short period of time, such that it is perceived by the patient as "flashed." As mentioned above, the described techniques require verification that the patient's fovea is fixated on the fixation target. It is during this fixation time that the test target is briefly displayed or flashed. Because the fovea is small, and it has much better vision than peripheral vision, a high-detail or high-attention task can be required to be done at the fixation target, such that can be accurately determined where the patient's eye is pointed. If it is known where the eye is pointed, a test target can be displayed in a location in the patient's field of view that corresponds to a specific location on the patient's retina. In this way, regardless of its properties, a fixation target is displayed in the manner that allows identifying where the patient's eye (one or both eyes) is pointed.

Thus, the fixation target(s) can be displayed at least in part simultaneously with a time when the test target is flashed. In some embodiments, the fixation target(s) can disappear from the patient's field of view once the test target has been displayed. In some embodiments, when a pointer is moved towards the location of the test target, both the fixation target and the test target may have disappeared from the patient's view. However, in some embodiments, the fixation target (or a portion thereof) can remain on the display, or one or more of its properties can change, while the next test target is displayed. At decision block 112, the user indicates whether they've seen the test target. This may be from the user moving a pointer towards the test target, the user moving her head towards the test target, a pupil response, a button press, or some combination of these indications. If the user indicates that they've seen the target, it is thus determined, at block 114, that the test target has been detected since the patient was able to perceive the test target (e.g., in the form of a flash) on a specific location on the patient's retina. This result is stored in a suitable format and in suitable memory hardware. It should be appreciated that processing at block 112 can additionally or alternatively involve determining whether the pointer is not moving towards the location of the test target and a predetermined period of time has passed (which can be an adjustable parameter). If it is determined that the pointer is not moving towards the location of the test target (e.g., the pointer is not moving or moving in the wrong direction) and a predetermined period of time has passed, it can be determined that the test target has not been detected—i.e., it has been missed because the corresponding location at the retina has a defect.

It is natural for a person to move his/her head in a direction of a target that attracted the person's attention, and a human orienting response starts with an eye movement, followed by a catch-up head movement, during which the eyes counter-roll to maintain fixation. In one implementation, if it is detected that the pointer moves (e.g., as a result of movement of the patient's head) in a correct direction towards the location of the test target (e.g., within the correct 30-degree sector when its excursion has reached 5 degrees), it can be determined that the target is has been detected by the patient.

Referring to FIG. 1A, if it is determined, at decision block 112, that the pointer is not moving towards the location of the test target, it is thus determined, at block 116, that the test target has not been detected. This can involve determining that a predetermined period of time has passed without the pointer being brought in the direction of the test target. Alternatively, a model may be used to determine whether or not the test target has been detected. This model would take inputs including, but not limited to, head position, head velocity, eye position, eye velocity and information about what visual test target has been displayed to the viewer (e.g. how the pixels on the screen changed leading up to seeing/ not seeing the test target). The process 100 can then proceed to decision block 118 where it is determined whether there are other test targets to display, and, if this is the case, the process 100 follows to block 104 to display a fixation target, which can be followed by displaying (at block 110) a test target, as discussed above.

If it has been determined, at block 114, that the test target has been detected, the process 110 follows to decision block 118 where it can be determined whether there are other test targets to display. If there are more test targets to display, the process 100 returns to block 104 where the next fixation target can be displayed, and, if that fixation target has been detected (which is determined at block 106), a next test target can be displayed at block 110. The fixation target may disappear from the patient's field of view, or it can remain being displayed. It should be appreciated that the processing at block 118 is shown by way of example only, since it can be determined whether a certain condition has been met, to decide whether to proceed to display a subsequent test target. For example, in some embodiments, the process 100 can be executed for a predetermined period of time, such that the process 100 terminates when that period of time has passed. The process 100 can also terminate based on other factors—e.g., when a certain number of test targets has been missed by the patient, or by a more complex model, etc.

As shown in FIG. 1A, if it is determined, at block 118, that there are no other test targets to display (which depends on the test parameters), the process may terminate and results of the test can be provided in suitable format, at block 120. For example, the results can be provided to a computing device of the patient and/or to a computing device of a clinician (which can be a remote device), the results can be displayed in a textual, graphical, or any other format, stored, and otherwise manipulated. Diagnosis can be generated based on the results, which can include probability of the patient's having more than one disease, current progress of the patient, or by a more complex model, etc.

Figure 1B:
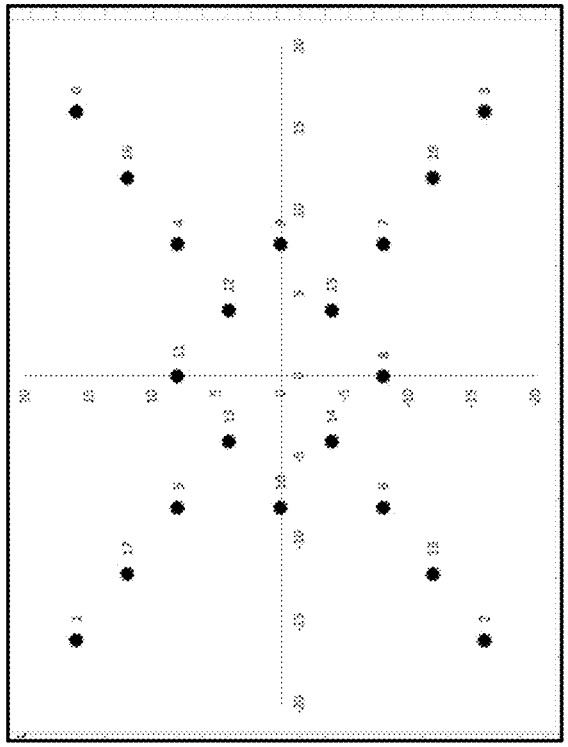
FIG. 1B is a spreadsheet for controlling a visual field test according to various embodiments of the disclosed technology.

It should be appreciated that, in some embodiments, it can be determined, at block 118, whether there are more test targets to display in a current layout of a current template. The layout can determine one or more of locations, number, order, and other features related to displaying the test targets. The template can include more than one layout, and the layouts of a template can have common characteristics. The template can be generated from a spreadsheet or other data file, such as the spreadsheet 150 of FIG. 1B for the layout 175. In one embodiment a spreadsheet contains a row for each possible stimulus or test target with columns for each property. Properties of the test target controlled by the columns can include position, luminance, duration, size, background luminance, movement, and shape. One or more of the columns may include text written in a simple programming language that is interpreted and used to determine the conditions under which a specific test target or a group of test targets will be displayed. That simple programming language would allow for the loaded layout to use information such as the status of individual or groups of stimuli seen, missed, presented, or remaining to be presented to determine if new stimuli should be enabled during testing. For example, a group of test targets may be enabled when half of a different group of stimuli are missed. The person administering the test may be able to edit the spreadsheet or data file using a text editor or it may be generated by a computer program. One purpose of using a spreadsheet or data file to control the test in this manner is to allow changes to the test without having to re-write or re-compile the computer code that otherwise administers the test. This allows non-programmers to create layouts that use information collected during the test in their testing strategies.

Once it is determined, at block 118, that all test targets in the current layout have been displayed, or the algorithm has reached a particular level of statistical confidence, or a disease classification has been made to a certain confidence, or time has run out, the process 100 can proceed to selection of a next layout in the template or to another template if there are no more layouts in the currently selected template. It should be appreciated, however, that in some embodiments a template may not be used and the information to be displayed on the display can be determined randomly. The information (e.g., properties, number, and locations of test targets, properties and locations of fixation targets, etc.) can be adjusted dynamically, for example, based on the user's current performance of the test and/or other factors.

The described techniques allow detecting and monitoring various patient's conditions (e.g., glaucoma). A patient's visual field is assessed by testing different locations within that visual field, and determining which locations have blind spots and/or have decreased function. Results of the assessment can be analyzed in various ways, as discussed in more detail below.

The described techniques can be implemented in any suitable system which can include a device having a display on which images are presented to a patient, a device controlling the presentation of the images on the display, an input device that is controlled by the patient performing a visual activity (e.g., a test, task, etc.) and that is configured to acquire user input from the patient. The same device can include both the display and the input device. For example, a head-mountable virtual reality device can have a virtual reality (VR) display, and user input is acquired in the form of movements of head and/or eyes of the user wearing the head-mountable virtual reality device and viewing the VR display. The head-mountable virtual reality device can be in the form of VR glasses having a built-in VR display, VR goggles, and any other headset VR device. Regardless of the implementation of the head-mountable virtual reality device, the described embodiments involve tracking movement of the head of the patient wearing the head-mountable device. In various embodiments, external cameras track movement of the head of a patient, for example when the patient is using a monitor or phone instead of a head-mountable device. Additionally, eye tracking can be used as well. Electroencephalogram (EEG) signals, and any other types of signals, can be acquired as well. Thus, various sensors can be used to acquire information as the user/patient is performing a test in accordance with the described techniques.

In some implementations, the user (e.g., the patient) can view a device's display (e.g., a display of a smartphone, personal computer, tablet, smart watch, etc.) and user input can be acquired either via an input mechanism that is part of that device (e.g., a touch button, touchscreen display) and/or via a separate input device, such as a computer mouse, a joystick, keyboard, another hand-held controller, etc. The user input can be received via one or more of a gesture and motion tracking device (which can recognize movements and gestures of user's hand, arm, other body parts, the entire body, etc.), a microphone, at least one camera, an omnidirectional treadmill, and a game pad. In various embodiments, user input can be received using at least one sensor selected from the group consisting of a head tracking sensor, a face tracking sensor, a hand tracking sensor, a body tracking sensor, a voice recognition sensor, a heart rate sensor, a skin capacitance sensor, an electrocardiogram sensor, a brain activity sensor, a geolocation sensor, at least one retinal camera, a balance tracking sensor, a body temperature sensor, a blood pressure monitor, and a respiratory rate monitor.

Furthermore, a computing device used by the patient to perform activities (e.g., tests) in accordance with the described techniques can be associated with eye tracking or other sensors monitoring the eyes (or the entire face) of the patient as the patient is performing the activity. For example, a smart TV or another device can have real-time eye tracking sensor(s) such that eyes of a viewer are monitored, which can be utilized in conjunction with the technique described herein. A smartphone or a personal computer can similarly have built-in eye tracking technology which can be utilized in addition to (or instead of, depending on the implementation) user input acquired using various devices controlled by the user. In addition, in some embodiments, values of various parameters of the head-tracking device or another device used by the patient are monitored. For example, images can be obtained to determine whether camera lenses are in a proper condition, etc. In some cases wearing glasses inside a VR HMD can interfere with the proper functioning of eye tracking devices inside the headset. To solve this problem, a lens insert can be manufactured to hold one or more trial lenses inside the headset so that the viewer's glasses are not required during the test. These inserts are typically sized to match commonly available trial lens sets. Alternatively, a custom insert may be made to order and sent for a particular user's prescription. Alternatively, the patient can wear contact lenses.

Figure 2A:
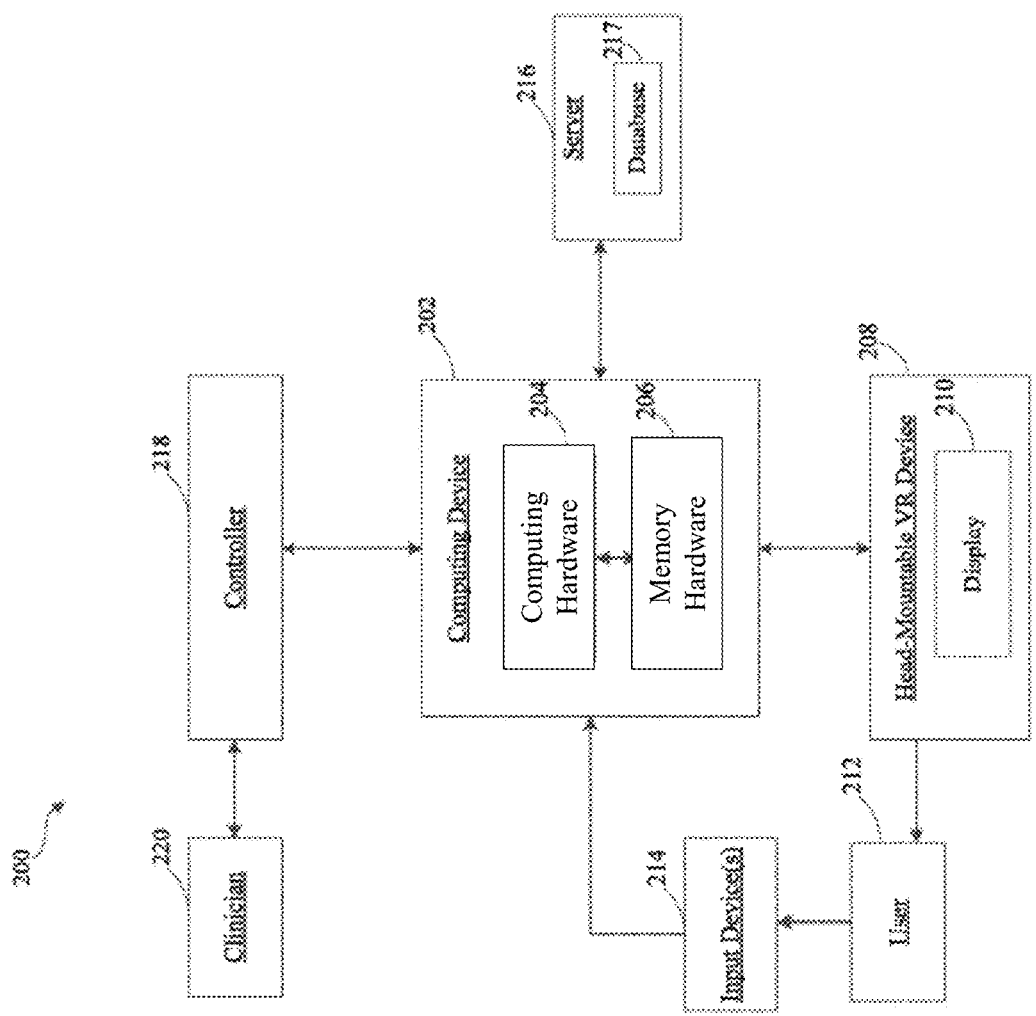
FIG. 2A is a block diagram illustrating a system in which some embodiments can be implemented.

FIG. 2A illustrates one embodiment of a system 200 which can be configured to perform a process of assessing a visual field of a user 212, such as, for example, the process 100 shown in of FIG. 1A or any other process in accordance with the described techniques. The user 212 can be any patient, of any suitable age and having any demographic characteristics, e.g., a child or an adult. The system 200 includes a computing device 202 including computing hardware 204 and memory hardware 206 coupled to the computing hardware 204. In this example, the system 200 also includes a head-mountable virtual reality (VR) device 208 configured to communicate with the computing device 202 and having a display 210 configured to display virtual reality (VR) environment to the user 212 wearing the VR device 208 such that the VR environment is viewed by the user. As shown in FIG. 2A, the system 200 can also include one or more input devices 214 configured to acquire user input based on active input received from user 212 and/or based on passively acquired sensor image data (e.g., head and eye tracking sensor(s)). Information acquired by the one or more input devices 214 is transmitted to the computing device 202, as shown in FIG. 2A.

As also shown in FIG. 2A, the computer system 200 can include or it can communicate via a remote connection with a server 216 which can include one or more databases 217 stored on one or more memory hardware and configured to store information acquired by the computing device 202 and other computing devices. The information, at least in part, can also be stored in the memory hardware 206 of the computing device. The server can automatically process data that can be accessed from devices communicating with it. The server can coordinate communication between the clinician and user.

As further shown in FIG. 2A, the computer system 200 can also include a controller 218, such as, for example, a touch display coupled to the computing device 202 and configured to receive user input from a clinician 220 or other type of input for controlling operation of the computing device 202 and the VR device 208 in connection with diagnosing, assessing or treating a vision disorder afflicting the user 212. In some embodiments, the controller 218 can be part of the computing device 202. However, in other embodiments, the controller 218 can be or can be included in a remote computing device (e.g., a clinician's computing device).

The computing device 202 can be any suitable computing device, such as a desktop or laptop personal computer, a personal digital assistant (PDA), a smart mobile phone, a server, or any other suitable computing device that can be operated by a user and can present services to a user. As mentioned above, the computing device 202 includes the computing hardware 204 and the memory hardware 206. Computer-executable instructions implementing the techniques described herein can be encoded on the memory hardware 206, which can include a hard disk drive, a Compact Disk (CD) or a Digital Versatile Disk (DVD), a persistent or non-persistent solid-state memory hardware (e.g., Flash memory, Magnetic RAM, etc.), or any other suitable memory hardware. The memory hardware has at least one physical property that is altered in some way during a process of recording data thereon. For example, a magnetization state of a portion of a physical structure of a computer-readable medium may be altered during a recording process.

In some embodiments, the computing device 202 can be coupled to the head-mountable VR device 208 via a wired or wireless connection. Similarly, the computing device 202 can be coupled to the controller 218 via a wired or wireless connection.

The head-mountable VR device 208 can be any suitable wearable device configured to provide a virtual reality, augmented reality, mixed reality, holographic reality space, or similar environment to the user 212 of that device 208. For clarity of presentation, examples herein may refer to VR or virtual reality. However, an augmented reality, mixed reality, holographic reality space or similar environment may be used for the disclosed examples and embodiments, and when applying the disclosed technology. The VR device 208 includes computing hardware, a visual interface such that the display 210, and memory hardware for storing computer-executable instructions for execution by the computing hardware. In some aspects, portions of the display of the VR device 208 can be transparent, semi-transparent, or opaque. The VR device 208 can be a holographic computing device having a see-through holographic display. For example, the VR device can be a HoloLens device developed by Microsoft Corporation. The VR device can be in the form of smart glasses or it can have other configuration.

The display 210 of the VR device 208 can display a different image to each eye of the use thus providing the user a sense of depth and 3D vision. The VR device 208 is configured to use a head tracking technology such that the device 208 acquires and transmits to the computing device 202, and/or to another computing device, information about the position and/or rotation of the head of the user 212. The display 210 can also be configured to implement eye tracking technology, which allows the VR device 208 to acquire information about the position, xy location, rotation, pupil size indicating pupil dilation of the user's eyes, and any other information that can be acquired by tracking user's eyes.

The VR device 208 provides a VR visual environment that gives a user a more realistic feeling of being part of such environment and a larger field of view where an accurate control of the image being shown to each eye can be achieved. Furthermore, when a user is wearing the head-mountable VR device 208, brightness can be a more controllable parameter since the VR device 208 itself provides a source of light to the displayed images. Other parameters of the displayed images are also more controllable thus allowing generating more consistent results, which can be particularly advantageous for reproducibility of the activities performed by the user and comparison of performance results for the same user or along multiple tests.

Figure 2B:
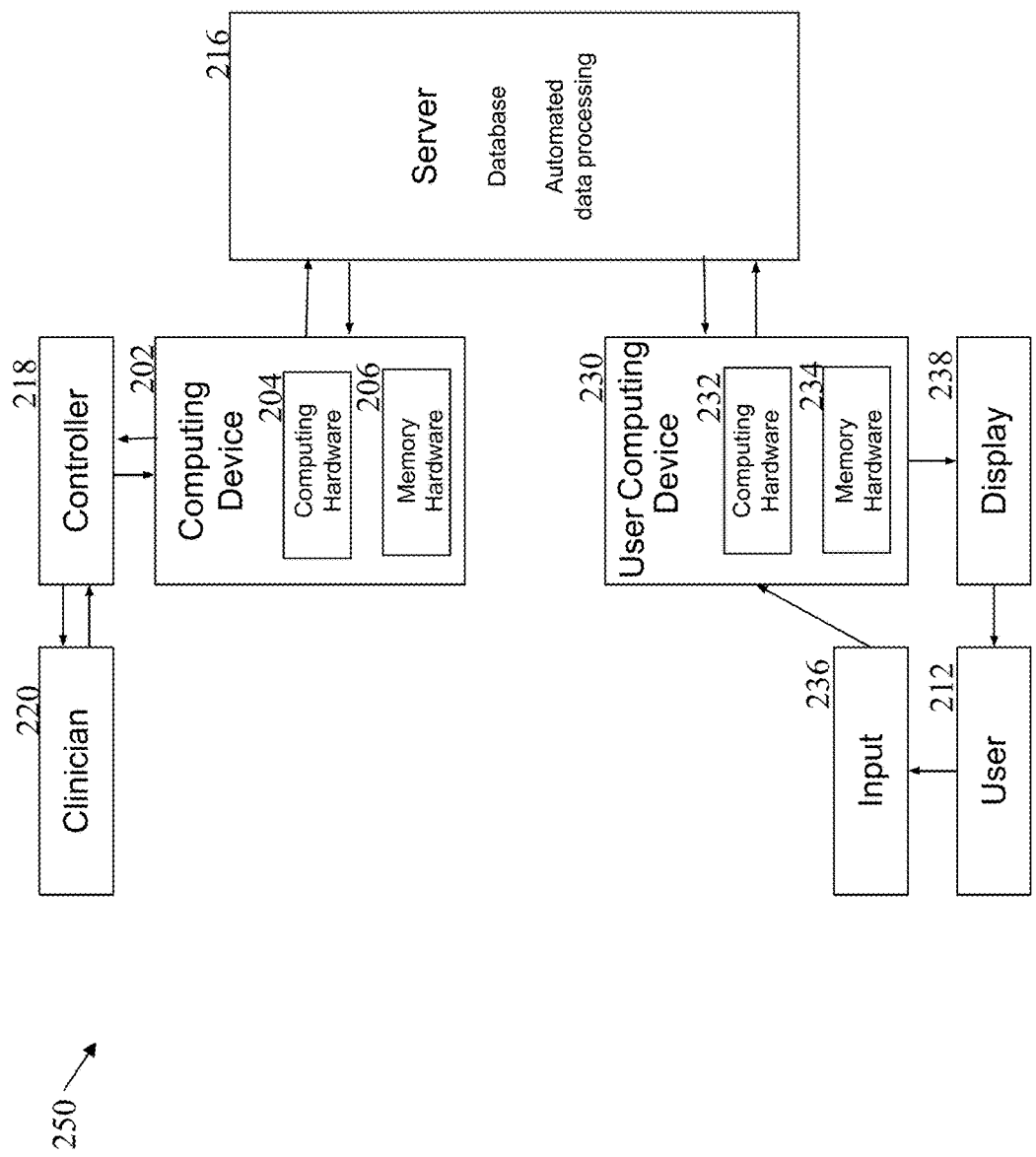
FIG. 2B is a block diagram illustrating a system in which some embodiments can be implemented.

However, it should be appreciated that the system 200 is shown to have the VR device 208 by way of example only. FIG. 2B illustrates system 250, in which the head-mountable VR device 208 may not be present. In such embodiments, visual information (e.g., fixation and test targets and any other visual information) can be displayed for view by a patient on a user computing device 230 (e.g., a smartphone, a personal computer, etc.) and user input 236 can be acquired in various manners that can be different from acquiring user input via a VR device.

As mentioned above, the VR device 208 can acquire and transmit to the computing device 202 input in the form of information on user's eye movement and/or information on user's head movement. The user input can also be acquired based on the user's using one or more input devices 214 communicatively coupled to the computing device 202. Non-limiting examples of the input device 214 include a mouse, keyboard, gesture/motion tracking device, microphone, camera(s), omnidirectional treadmill, game pad, body temperature monitor, pulse rate monitor, blood pressure monitor, respiratory rate monitor, electroencephalography device, or any other device.

The computing device 202 and the VR device 208 can be used in a home setting or other environment outside of a medical facility. Thus, the computing device 202 coupled to the VR device 208 can be controlled by the user 212 operating the devices. It should be understood that, if the user 212 is a young child who needs assistance with operating the devices, a parent or other person can assist such user.

In some aspects, the computing device 202 and the VR device 208 can be employed in a clinical setting such as in a suitable medical facility. In such scenarios, operation of the computing device 202 can be controlled via the controller 218 which can be, e.g. a touchscreen device coupled to the computing device 202 and operated by a clinician 220. The touchscreen device can mirror images visible to the user 212 via the VR display 210 (e.g., images for the left and right eyes of the user 212) and it can be configured so as to receive input for controlling the virtual environment images displayed on the VR display 210. The controller 218 can be a monitor or a computing device similar to the computing device 202, or any other device. Regardless of the particular type of the controller 218, a display associated with the controller 218 can be used to control in real time, as the user 212 is wearing the VR device 208, the virtual environment provided to the user 212.

In some aspects, the controller 218 can communicate with the computing device 202 wirelessly over a computing network including wireless communication medium or media for exchanging data between two or more computers, such as the Internet. The controller 218 can thus be located at any location assessable via the computing network, including a location geographically remote from a location of the computing device 202. Thus, a user equipped with the computing device 202, such as a mobile phone (e.g., a smartphone or any hand-held computing device which can be a convergent device encompassing capabilities of multiple devices), and a suitable VR device 208 (which can be a low-cost headset as known in the art or developed in the future) can be located remotely from a clinician operating the controller 218 to control via the computing device 202 the virtual environment of the user. This telemedicine technique can simplify, decrease costs of, and make more accessible early diagnosis and timely treatment of many vision disorders. Because communication between trained medical professionals and patients is simplified and fewer or no hospital visits can be required, more patients can receive access to proper treatment of vision problems. The telemedicine approach can be particularly advantageous for persons living in rural, remote locations where such persons would otherwise have limited access to adequate vision care.

As shown in FIG. 2A, the computing device 202 can communicate with the server 216 over a communication network, such as the Internet. The server 216 acts as a central repository of data relating to vision treatment platforms (e.g., a platform performing the process of FIG. 1A or another process in accordance with the described technique) executed on a plurality of computing devices including the computing device 202. Data relating to all measurements and treatments conducted using the described techniques, including timing data, can be recorded and stored on the database 217 in the server 216, which can be one or more databases. The users can then view a complete history of their visual performance. The data stored on the server 216 can be accessible to the user via a computing device, such as the computing device 202 or any other device, in a manner that allows the user to sort and analyze the historical data in various ways, view various statistics derived from the data, compare that user's performance to the performance of other users (e.g., based on averages generated from all of the users, or any other parameters). The results of the analysis and comparison can be presented to the user or other person (e.g., a clinician) in visual formats that facilitate understanding of the results. The user can be enabled to customize the manner of the representation of the results.

As shown in FIG. 2B, the user computing device 230 can communicate with the server 216 over a communication network, such as the Internet. The server 216 acts as a central repository of data relating to vision treatment platforms (e.g., a platform performing the process of FIG. 1A or another process in accordance with the described technique) executed on a plurality of computing devices including the user computing device 230. Data relating to all measurements and treatments conducted using the described techniques, including timing data, can be recorded and stored on the database 217 in the server 216, which can be one or more databases. The users can then view a complete history of their visual performance. The data stored on the server 216 can be accessible to the clinician via a computing device, such as the computing device 202, and to the user via a computing device, such as the user computing device 230 or any other device, in a manner that allows each of the clinician and user to sort and analyze the historical data in various ways, view various statistics derived from the data, compare that user's performance to the performance of other users (e.g., based on averages generated from all of the users, or any other parameters). The results of the analysis and comparison can be presented to the user or other person (e.g., a clinician) in visual formats that facilitate understanding of the results. The user can be enabled to customize the manner of the representation of the results.

It should be appreciated that, as mentioned above, the VR device 208 is shown in FIG. 2A by way of example only. As shown in FIG. 2B, a user computing device 230 including computing hardware 232 and memory hardware 234 coupled to the computing hardware 232 having or associated with a display 238 can be used to implement the described techniques. For example, test stimuli or targets can be rendered on a user interface of a display 238 of a smart phone, a personal computer, tablet, TV, smart watch, etc. Thus, in some embodiments, a display of a computing device other than a head-mountable device 208 is configured to be viewed by the user 212. Furthermore, in some embodiments, more than one user input device can be used—e.g., a head-mountable VR device 208 and a hand-held user computing device 230. In some cases, visual information can be displayed and user input can be acquired for testing purposes such that position and movements of the entire user's body can be monitored, which may or may not be done in combination with one or more input devices.

The system in accordance with some embodiments is configured to accept user input indicating a location of a detected target, and user input is deemed appropriate if the user input includes an indication of a location of the target, along with an indication of detection of the target. A requirement for an extended training of patients to keep their gaze fixated on a target can be reduced or eliminated.

As mentioned above, because a head-mountable device is used to display targets in a virtual reality environment rendered by a display, a test (or other activity) does not require patient comfort to be compromised. For example, the test does not require a patient to hold still, sit up straight for a certain duration of time, and to keep her or his head still (either with or without a specific head-immobilizing support such as a chin rest). Young, weak, and elderly patients can have difficulty maintaining necessary physical position relative to an existing system, and many may thus be unable to complete testing. The use of the head-mountable device in some embodiments described herein eliminates a need for immobile, bulky, and costly equipment, while decreasing discomfort experienced by some patients. The head-mountable device is typically of a smaller size, more portable, and less costly than existing devices and systems for perimetry. The head-mountable device can be used in conjunction with a variety of input devices. For example, monitored user input can include head, hand, other body part or entre body, eye tracking, etc. In some cases, sensors can be attached to the user's body (e.g., head or another part) and user input in an objective form can be received.

Furthermore, the described techniques can involve displaying information on other types of displays such as, for example, computer monitors, smart phones, and TV monitors. Various types of user input devices can be utilized. Also, as mentioned above, sensors can be attached to the user's body (e.g., head or another part) and user input in an objective form can be received.

In some embodiments, sequential-foveation perimetry (SFP) techniques are used, which overcome potential shortcomings of fixation loss by exploiting, instead of suppressing, the tendency of a person to look towards a new visual target. This is achieved by presenting visual information to a patient in a manner that encourages the patient to look at test targets as they are presented. Also, the visual information is presented in the manner that input can be received from the user indicating the location of the presented test target. In this way, a number of occurrences of false positives is reduced, because the information is presented such that the patient is prevented from responding to a test target that the patient did not see.

The described system can utilize statistical methods to determine locations in the visual field to test, estimate the likelihood that results are indicative of a disease, and monitor progression of the disease over any time period (e.g., days, weeks, months, or years). The testing and other activities can be performed either with or without eye tracking, as well as other response methods. The activities can be implemented for screening for diseases that affect the visual field, as well as for mapping out various threshold values across the retina. Also, the activities, such as testing, can be used to map out binocular (cortical) scotomas in patients with strabismus and/or amblyopia. Information acquired when each patient is being tested can be stored in a suitable location. A Bayesian or another approach can be used to analyze the collected data.

If the test is used for screening, a pattern of visual field loss in which both eyes show a similar deficit can be used to diagnose cortical damage.

In some embodiments, at least one target is displayed on a display of a head-mountable device such that the targets are displayed (e.g., briefly flashed) as "white-on-white" spots of light. For example, targets can be displayed on a white (or another light-colored) background, with the targets being in the form of various light-colored objects. In other embodiments, "dark-on-white" tests can be used, such that targets are displayed on a white (or another light-colored) background, with the targets being in the form of various dark-colored objects (e.g., darks spots). The "dark-on-white" tests have a potential to better engage a person's visual system's OFF subsystem, which is more sensitive than the ON subsystem. In other embodiments, additionally or alternatively, targets can include moving Gabor targets. Furthermore, in some embodiments, various parameters of a displayed test target can vary. Non-limiting examples of such parameters include location of the target, contrast, brightness, target's size, color, motion, duration, etc. Colored and/or flickering test targets, as well as targets of any other type, can be presented.

In some embodiments, the head-mountable device can be Oculus Rift™ Samsung Gear™, and HTC Vive™, or any other head-mountable device. The head-mountable device can be configured such that it can be worn by a patient for a relatively long period of time, without causing patient discomfort. The head-mountable device can be configured to be used for a patient at home, such as no or minimal (e.g., via a telemedicine platform, or any other communication manner) supervision by a medical professional is required. Also, a headset is configured to be mounted to a patient, so that the patient does not have to keep his/her head stationary (e.g., in an uncomfortable chin/forehead rest, as in some conventional set-ups for perimetry). Moreover, the headset can be worn by the patient while the patient is sitting, standing, or lying down, without compromising performance of tests using the headset.

The headset can have built-in eye tracking sensors. Furthermore, in some embodiments, various other techniques can be used to determine whether targets have been seen by the patient. Non-limiting examples of such techniques include electroencephalogram (EEG) and measurement of pupil size/response. In some embodiments, electroretinography (ERG) can be used to determine if patient's photoreceptors and ganglion cells are responding to light hitting the retina.

Targets can be presented in a way that encourages patients to naturally look at the targets when they appear. Because, as mentioned above, user input is acquired indicating a target's location, occurrences of false positives are reduced. Furthermore, patient instruction sand performance monitoring can be automated, physicians can monitor their patients' visual field tests remotely, new tests can be evaluated, and targets can be presented to either (or both) eyes on a given trial. Also, data acquired during each test can be stored for subsequent analysis.

In some embodiments, as discussed above, test targets can be displayed in conjunction with a "head-pointing" technique which involves displaying a target such that a patient is required to turn his/her head towards the target. Testing is implemented such that the patient is meant to fixate his/her gaze on a fixation target (i.e., look at the fixation target with his/her fovea) presented on the display. Also, test stimuli (or test targets) are presented to the display at a particular location of the patient's visual field. The testing can be administered such that a patient is instructed to perform a task that requires the patient to fixate on the fixation target. In some embodiments, a test can be administered using a template that includes one or more layouts with logic to control how the test is administered. A layout can be configured to test different areas of a patient's visual field. A layout to be administered to a patient can be selected based on patient's characteristics, prior results of the patient's visual field assessment, and/or based on other factors. During a test, a display of a head-mountable device worn by the patient, or another display, displays a head pointer, such as a small object (e.g., a reticule, a virtual dot, etc.) visible to the patient that is rendered so that it has constant coordinates relative to the patient's head. In this way, regardless of the position and movements of the patient's head, the head pointer is displayed such that it appears "straight ahead" of the user. Thus, when the patient' head turns, the location of the head pointer, as the patient views it, remains the same as prior to the head turn. Once a test target is displayed (e.g., "flashed"—displayed for a relatively short period of time), the patient moves his/her head towards a detection zone, which is an area to which the head pointer should be moved to indicate that the patient has detected the test target. The detection zone is a predetermined area in the patient's visual field, and a size (e.g., its area) of the test target can be selected such that the test target is smaller than the detection zone.

For each patient, a type of a test to present to that patient can be selected, which involves selecting various test parameters such as, e.g., points (e.g., in the form of detection zones) to test, selecting type(s) of test targets or stimuli (including various properties of the stimuli—e.g., a size, color, shape, duration of being rendered, frequency of being rendered, etc.), and order of the presentation of the test targets on the display. The test parameters can be selected manually, e.g., via suitable user interface configured to receive input from a user such as a health care professional, or the test parameters can be selected, at least in part, automatically. For example, the test parameters can be selected, prior to or during the test, automatically, which can be done based on various factors, such as patient-specific characteristics (e.g., age, gender, anatomical characteristics, medical conditions(s), etc.) and historical information on the patient's prior performance of the test.

Furthermore, it should be appreciated that, in some embodiments, instead or in addition to tracking movements of the patient's head, another type of user input can be detected to determine whether the patient was able to see a test target. For example, the user input can include an input received from eye tracking sensor, an eye pointer, or another device.

In some embodiments, test targets can be displayed, e.g., in a VR environment presented on a VR display of a head-mountable VR device, in the form of a series of fixation of targets. A head-pointer object is also displayed, which can move as the user's head is moved. After at least one target is displayed on the display of the head-mountable device worn by a patient, it is detected whether user input is received indicating that a patient has "positioned" (e.g., by moving his/her head, or in other ways) the head-pointer at least partially on (or over) a fixation target. When it is detected that the user input is received and the received user input indicates that the head pointer is correctly positioned at least partially on the fixation target in the virtual environment, a next target can be displayed. In this way, the patient may not be specifically instructed to fixate his/her gaze on a target. Rather, fixation on the displayed target is required to do the task quickly, because the head-pointer object is required to be made to "collide with" (partially overlap) the fixation target, and both the head pointer object and fixation target can be of a relatively small size. Sufficient visual acuity to perform this task requires gaze fixation.

When the user input is received indicating that the head pointer object is within a certain distance to or at least partially overlaps the fixation target, another visual test target can be displayed. It should be appreciated that the head-pointer object can be "positioned" at least partially over the fixation target in various ways. For example the head-pointer object can be displayed at least partially over the target, or the target can be displayed to be at least partially over the head-pointer object. In some scenarios, it may be required that the head-pointer object is "positioned" entirely over or within the head-pointer object. Any visual representation in the virtual environment can be used, such that the user (with one or both eyes) perceives the head-pointer object to be moved towards the target. Each test target can be displayed for a certain duration of time (e.g., about 300 ms, in one example), and the patient can moves the head-pointer object visible to the patient towards the test target (if the target is visible to the patient).

In at least one embodiment, the testing method can involve displaying blind spot targets to each eye, and instructing the patient to adjust a position of a headset until the blind spot targets disappear from a display of the headset (the blind spot targets are targets that are placed at the correct location on the retina in each eye so as to land on the blind spots of the retina). Further, in a tutorial mode, sham (training) targets can be displayed such that the patient learns to perform the test (the tutorial mode can be optional). Also, prior to performing a test (e.g., during the tutorial mode), calibration of response times, motor control, and pointer accuracy can be performed to change various parameters of the test, such as, e.g., a duration of time which is required to pass from a time when a test target was displayed to determine that the test target has been missed (when no appropriate indication based on user input was received). After the training/setting mode has been completed, a template (e.g., a testing algorithm), and a first/current layout of the template can be selected. The testing method can then be performed, e.g., similarly to process 100 (FIG. 1A), or in other ways.

Figure 3:
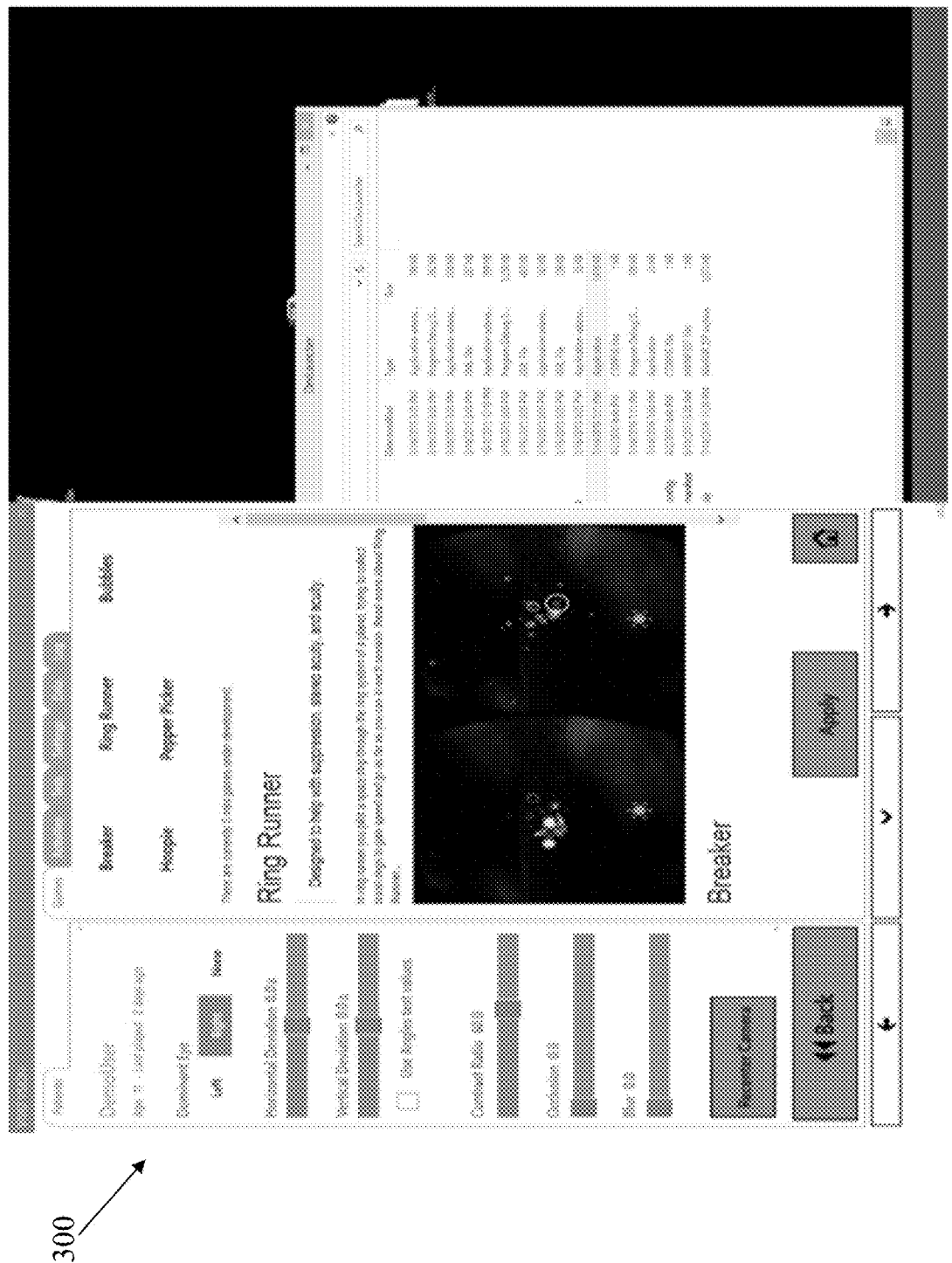
FIG. 3 is an example of a user interface of a computing device rendered in accordance with some embodiments.

FIG. 3 illustrates an example of a user interface 300 that can be rendered on a display of a computing device used by a person (e.g., a healthcare professional) supervising a patient performing a visual test or activity. The user interface can additionally or alternatively be rendered to the patient. As shown in FIG. 3, the user interface includes a panel (on the left) indicating patient information and including features (e.g., buttons and sliding bars, in this example) that allow adjusting various parameters (dominant eye, horizontal deviation, vertical deviation, contrast ratio, occlusion, blur). The user interface also includes a right panel including several tabs—"Games," "Activities," "Tests," "Settings," "Data," and "Log." In this example, a game of Ring Runner is selected that is designed to help with suppression, stereo acuity and acuity. The information presented in connection with the Ring Runner being selected relates to the description of the game: "in ring runner you pilot a space ship through the ring system of a planet trying to collect boost rings to gain speed and go as far as you can in each session."

Figure 4:
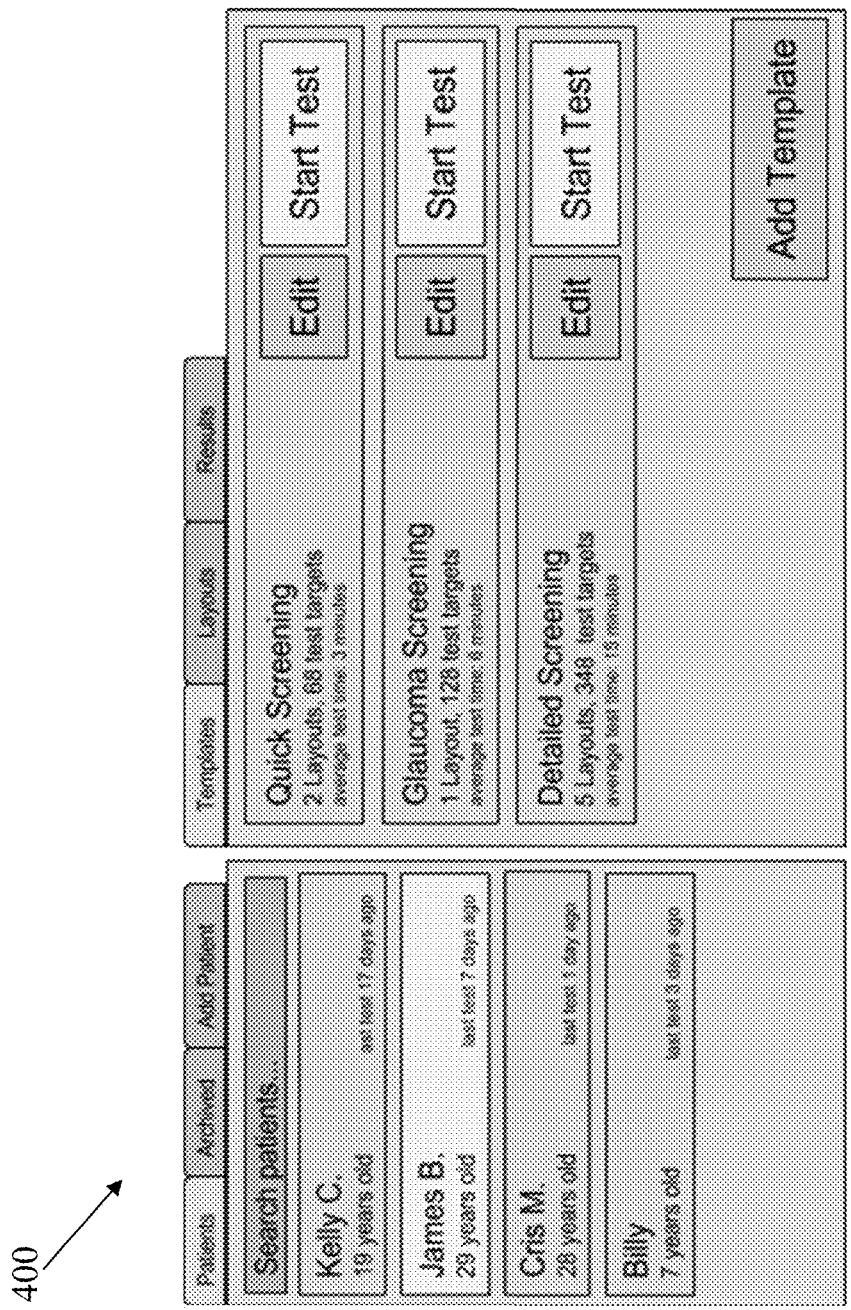
FIG. 4 is an example of information that can be displayed on a user interface of a computing device rendered in accordance with some embodiments.
Figure 5:
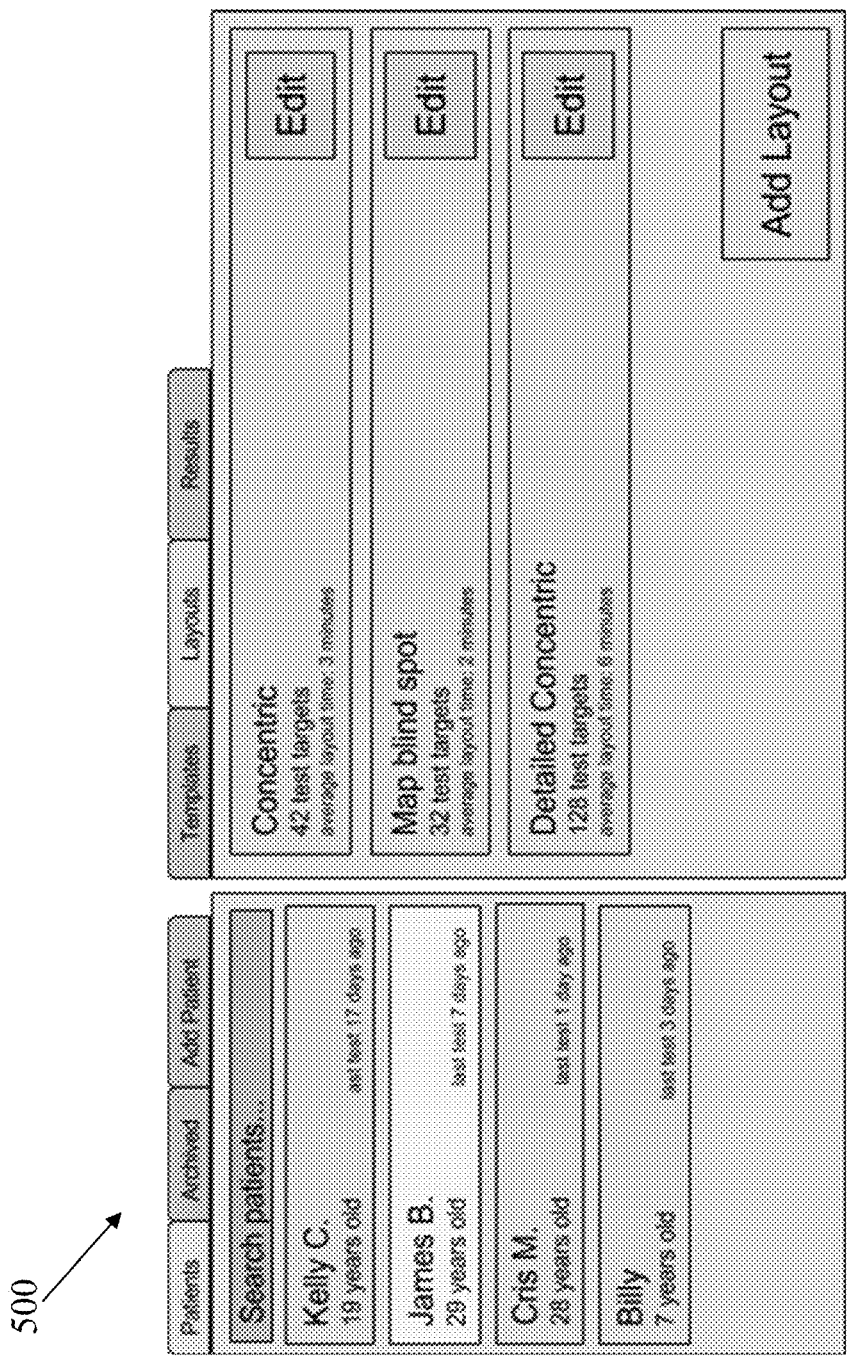
FIG. 5 is another example of the information shown on the user interface of FIG. 4.

FIG. 4 shows schematically an example of a user interface 400 including various selectable tabs. In this example, tabs of a left panel include "Patients," "Archived," and "Add Patient." Tabs of a right panel include tabs "Templates," "Layouts," and "Results." In FIG. 4, the tab "Patients" is selected that includes various information on patients. Also, the tab "Templates" is shown selected that includes various types of screening tests and control buttons associated with each of the tests. Thus, a template can be selected and it can be started (i.e., used for testing) or edited. Each template allows a user (e.g., a healthcare practitioner) to define algorithm(s) for testing. Each template may use more than one layout. For example, a screening layout can be created which can continue to layouts designed for specific deficits. Once a test is selected (e.g., a "Start Test" virtual button is selected, the use interface renders information related to the test. FIG. 5 shows schematically another example 500 of the user interface of FIG. 4, with the "Layouts" tab selected.

During a test, a user interface of a computing device can display information related to the test and performance of the test by the patient. The information can include, for example, information on the current status of the test, as well as options to pause, start, or modify one or more parameters related to the test. Once the test is completed, results of the test can be rendered on the user interface.

For each layout, default settings related to that layout can be modified. For example, a test target can be selected for editing such that default settings for that test target are overridden. Some testing algorithms can use layouts (e.g., a basic grid search). However, other testing algorithms do not depend on a layout and employ probabilistic (e.g., Bayesian) approaches to determine where and how parts of the visual fields are tested.

In some embodiments, a layout can specify a test target size, a test target duration (a time during which the test target is to be displayed), a test target brightness, a test target detection radius, a fixation target size, a fixation task, qualifiers and/or quantifiers to confirm fixation, a number of test targets, and properties (e.g., color, brightness, etc.) of a background on which the test targets and fixation targets are to be displayed.

One example of settings for a layout is as follows:
Test target size: 0.1-2 degree, default 0.43 degrees;
Test target duration: 0.1-1 seconds, default 0.2 seconds;
Test target brightness: 0-1, default 0 (black);
Test target detection radius: 0.1 to 10 degrees, default 4 degrees;
Fixation target size: 0.1-2 degree, default 0.5 degrees;
Fixation task: abxy buttons, tracing, default none;
Confirm fixation: true, false, default true;
Layout: 42 points, concentric;
Background brightness: 0-1, default 1 (white).

Figure 6A:
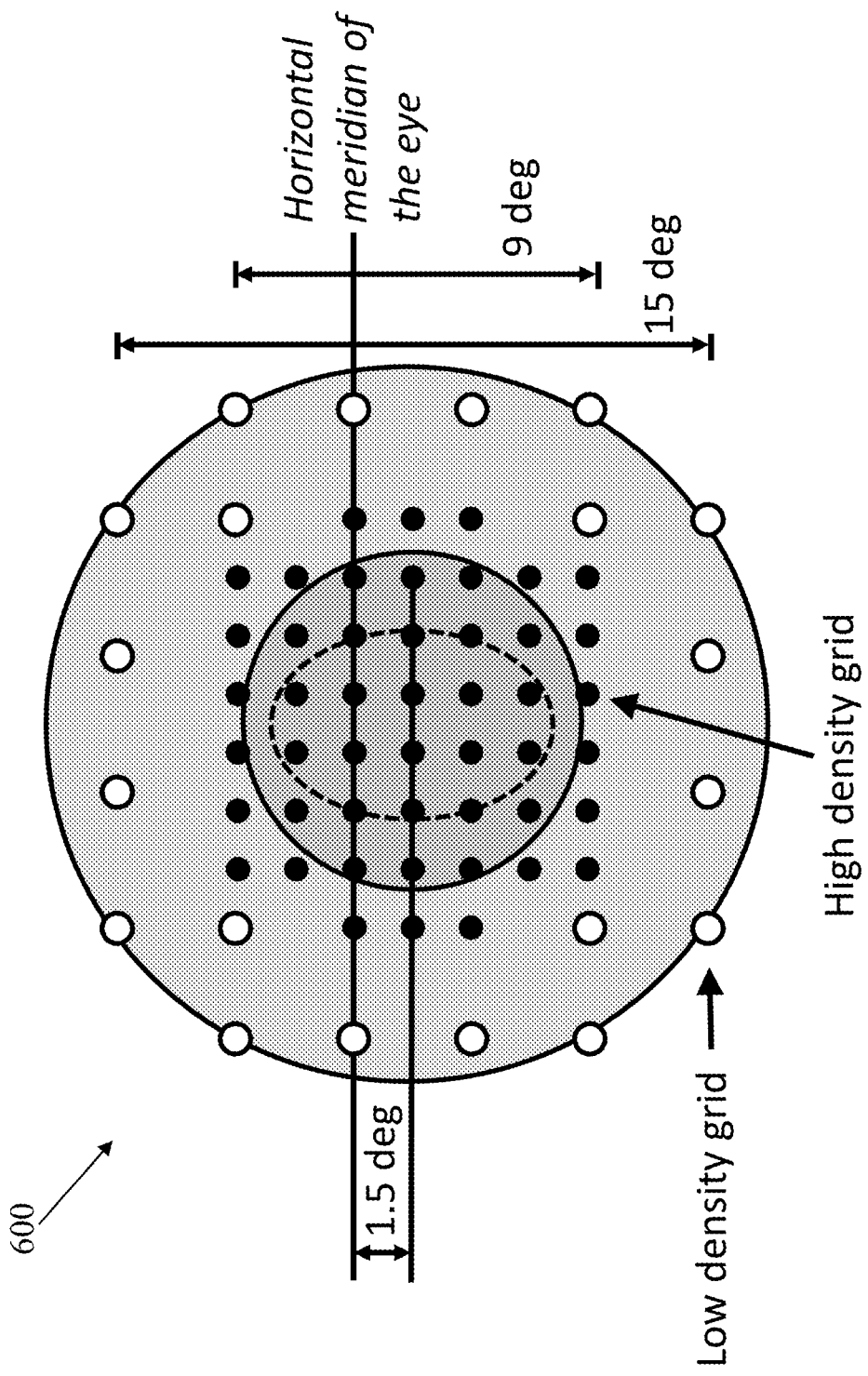
FIG. 6A is a schematic illustration of one example of a blind spot mapping layout of a template, in accordance with some embodiments.

It should be appreciated that various other layouts can be used in the described techniques. FIG. 6A illustrates one example 600 of a blind spot mapping layout of a template. As shown, the blind spot mapping layout includes a high density grid disposed in a center of the layout, and a low density grid that surrounds the high density grid. The dashed oval represents the average location of the blind spot, which is typically 5 degrees wide by 7 degrees high. In a person with highly stable fixation, a blind spot map can be used to register the data from the visual field test to a photograph or other anatomical image of the retina.

Figure 6B:
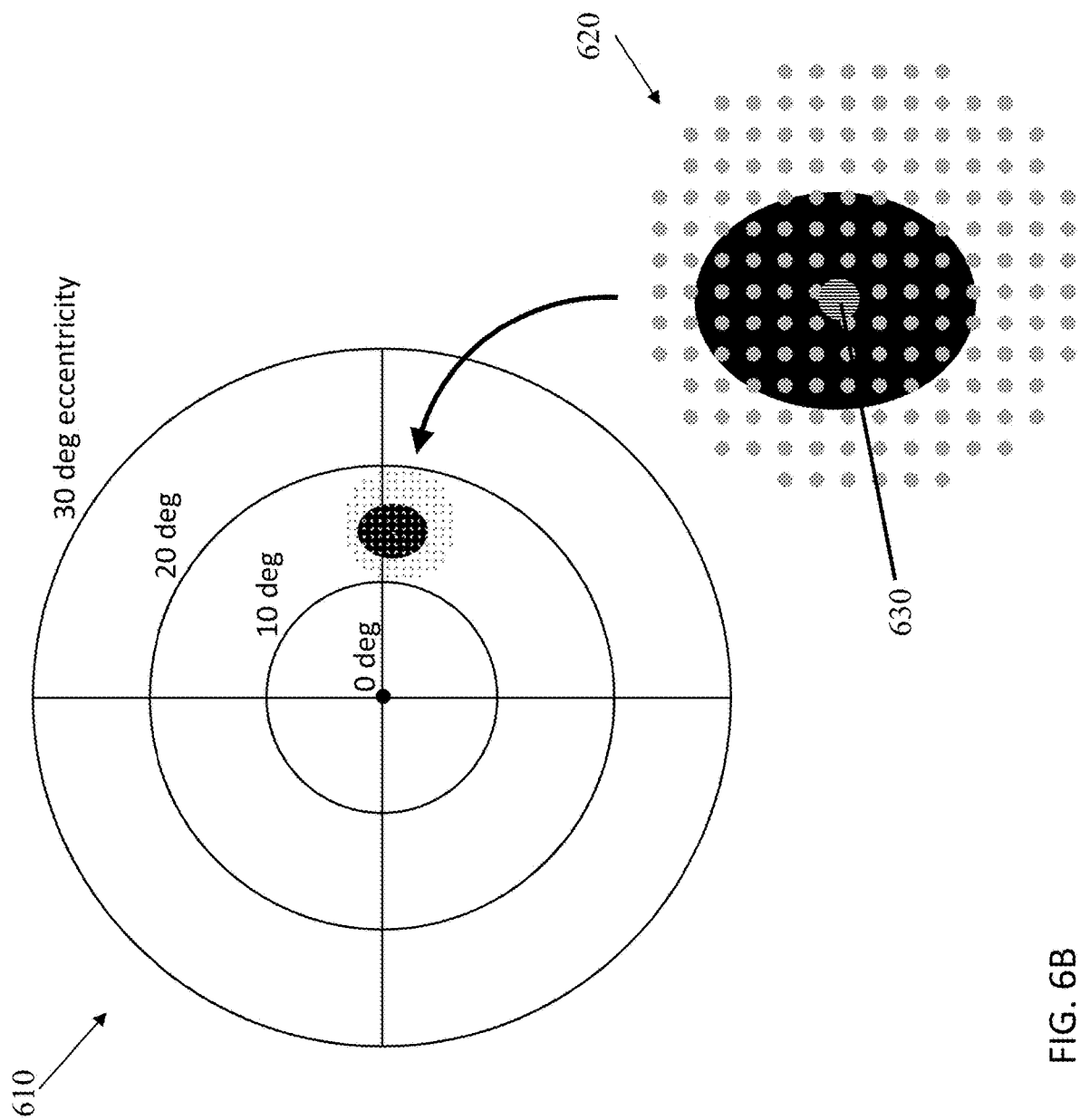
FIG. 6B illustrates a sampling grid that covers the expected location of the normal blind spot at a spatial resolution of 0.7 deg target spacing.
Figure 6C:
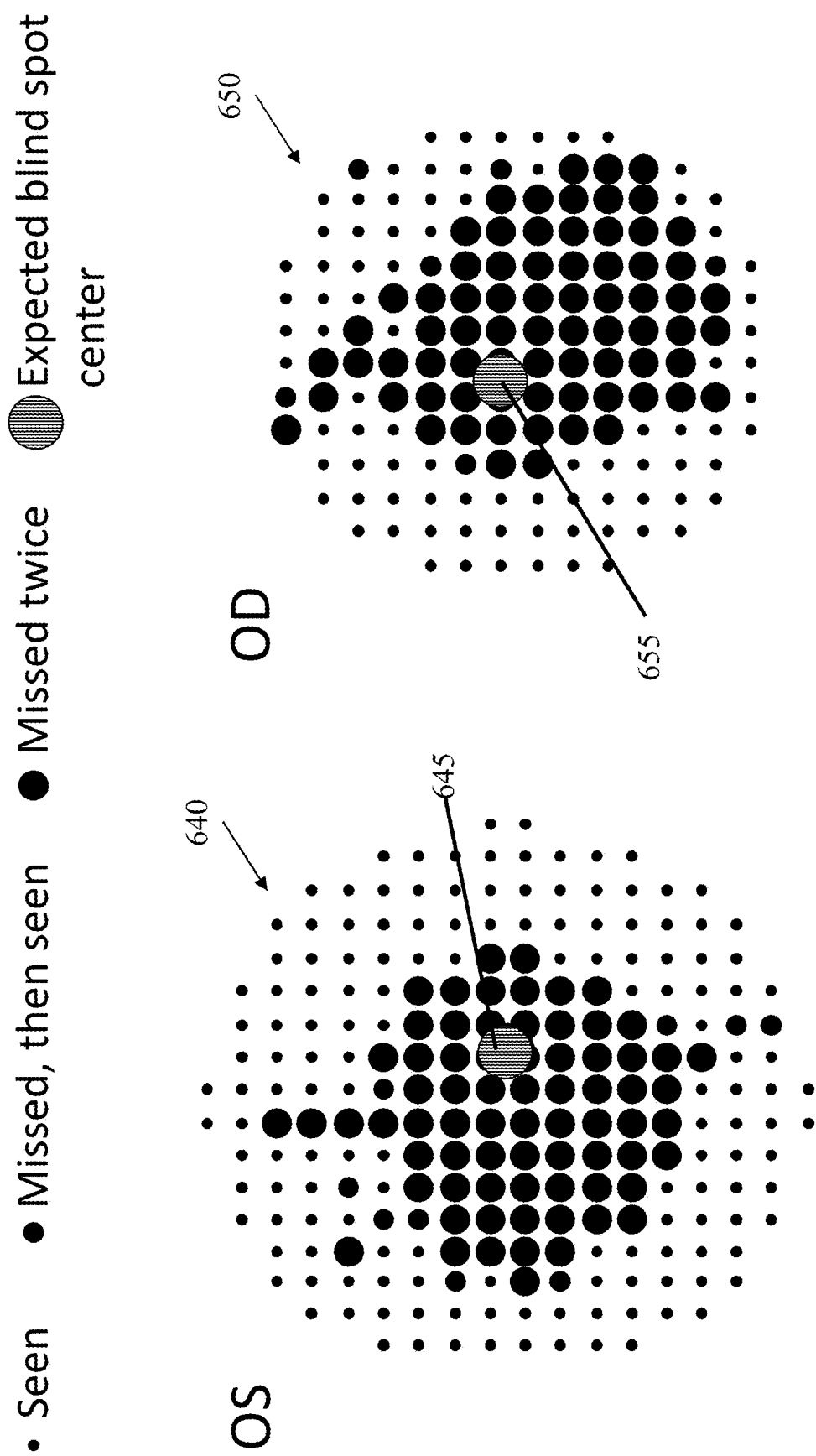
FIG. 6C illustrates two sets of data obtained by testing in the left and right eyes.

FIG. 6B illustrates a sampling grid 610, with close up 620, that covers the expected location of the normal blind spot at high spatial resolution (0.7 deg target spacing). The circle 630 with a vertical line pattern corresponds to the standard blind spot test location. The test parameters for the example in FIG. 6B may include:
Background luminance: white (~80 cd/m$^2$)
Target luminance: 0.5×white (~40 cd/m$^2$)
Target duration: 300 ms
Lattice spacing: 0.7 deg
Target spot size: 0.3 deg diameter
Total test time: 15 min, 45 sec
Array center: (15.0, −2.0) deg
Array radius: 5 deg FIG. 6C illustrates two sets of data 640 and 650 obtained by testing in the left and right eyes, respectively. In these images, small spots represent locations where the target was seen and not tested again; medium-size spots represent locations where the target was missed, then shown again and seen; and large spots represent locations where the target was missed twice. The circles 645 and 655 with vertical line patterns correspond to the standard blind spot test location for each eye. These targets were also missed twice.

Figure 6D:
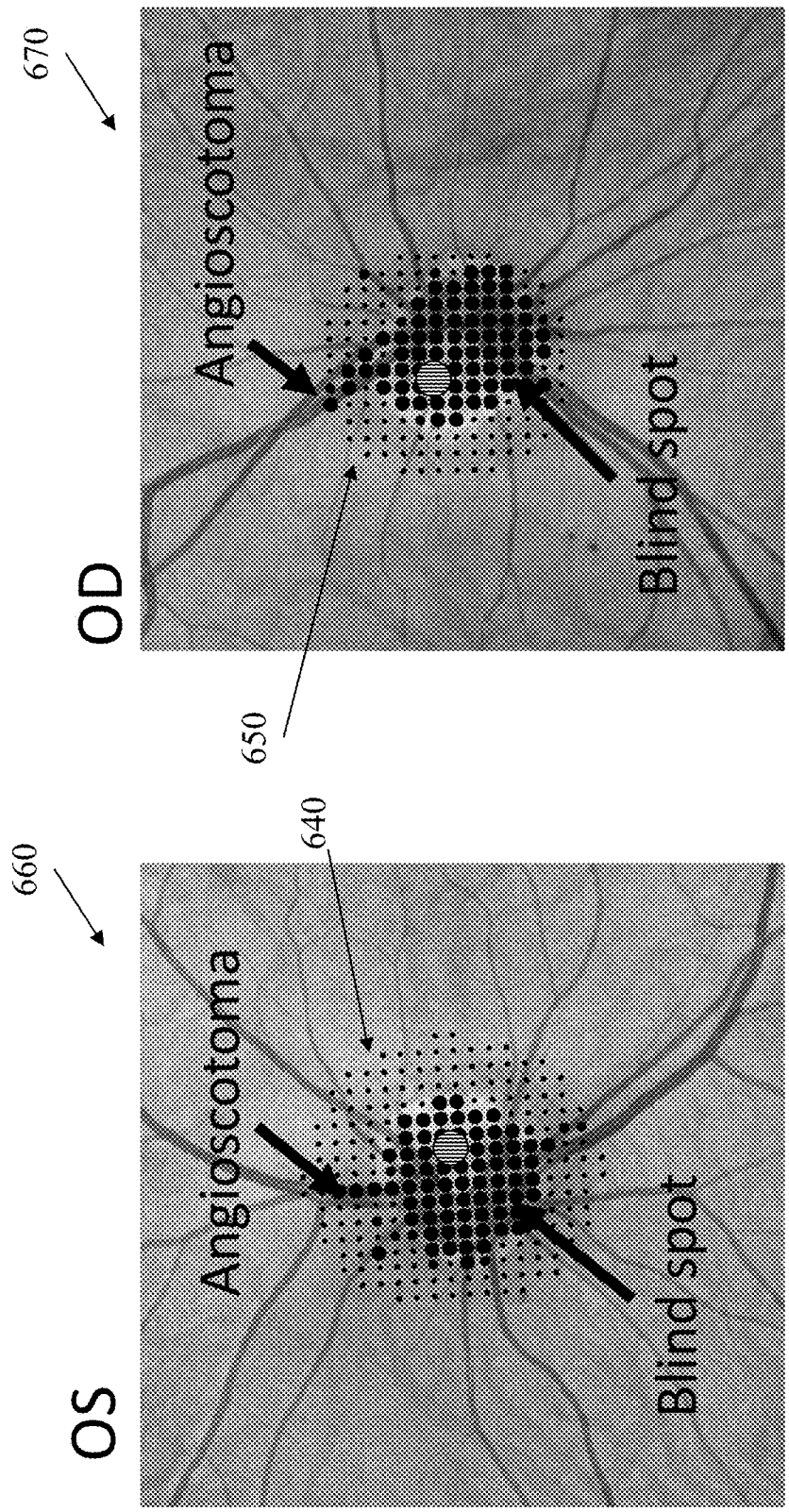
FIG. 6D shows the data of FIG. 6C graphically overlaid onto the respective fundus images from the same person.

FIG. 6D shows the data 640 and 650 of FIG. 6C graphically overlaid onto the respective fundus images 660 and 670 from the same person. The data have been rotated, scaled, and translated to match the vascular pattern of each eye. By overlaying the data of 6C over the vascular pattern of each eye, it is possible to identify angioscotomata patterns, in which patterns of blind spots correspond to blood vessels. Angioscotomata patterns form streaks or linear segments, in contrast to the blind spot formed by the location of the optic nerve.

Figure 6E:
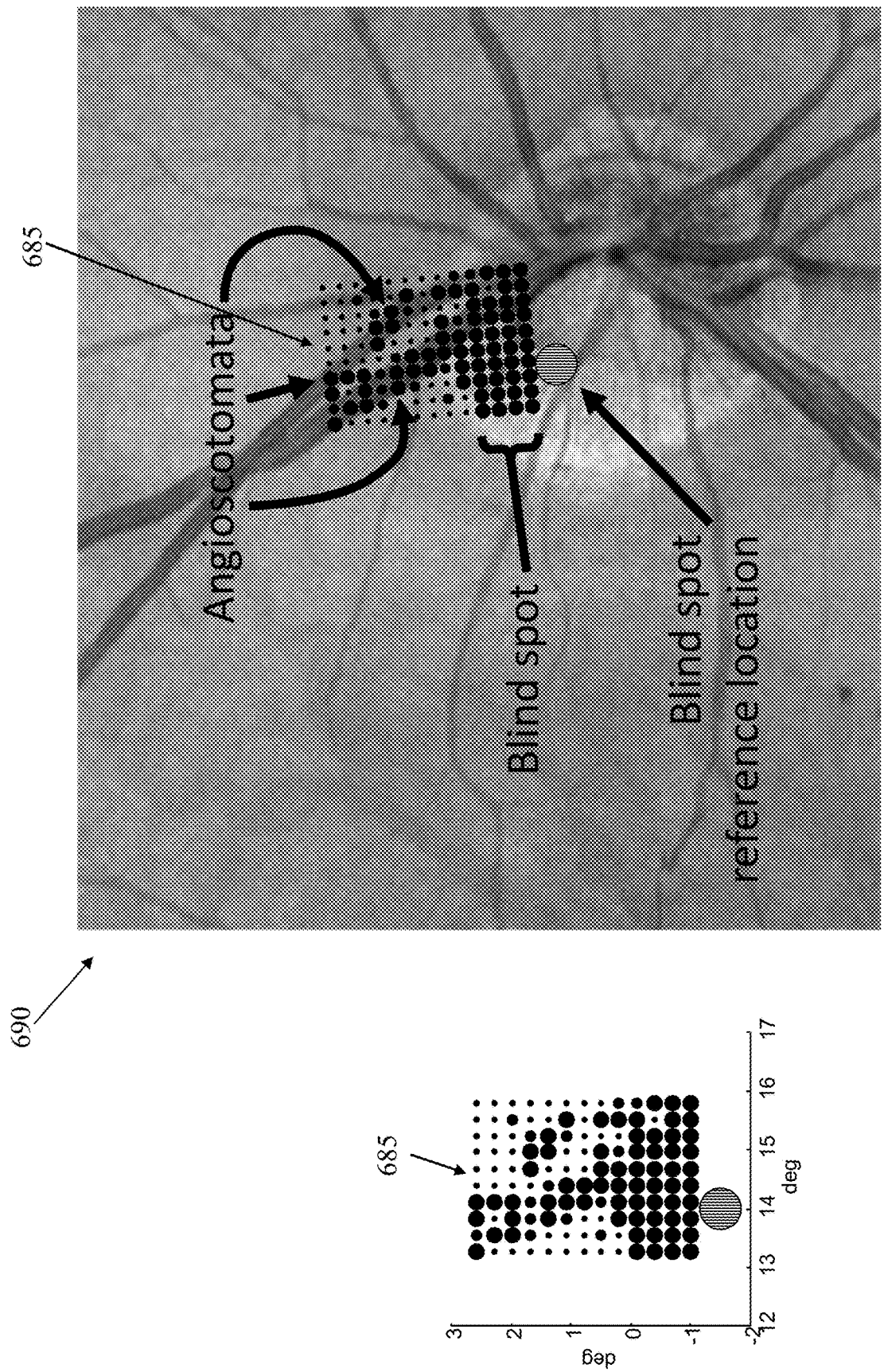
FIG. 6E shows another test pattern at a spatial resolution of 0.3 deg target spacing, showing angioscotomata.

FIG. 6E shows another test pattern 685 at higher spatial resolution (0.3 deg target spacing). The same fitting parameters (rotation, scaling, and translation) as used to overlay data from the test patterns 640 and 650 on the retinal images 660 and 670 in FIG. 6D was used to transform the data 685 in FIG. 6E and overlay the data 685 on retinal image 690. Consequently it can be appreciated that the locations of blood vessels in the eye can be measured with high precision using the fixation and testing strategy of the device described, and that subsequent visual field data can be co-registered spatially with high precision.

This method of mapping the normal blind spot and this method of mapping the blood vessel locations at the blind spot or elsewhere on the retina can be used to register visual field testing data that have been distorted by magnification or minification of the images due to the wearing of ophthalmic corrections. Currently, visual field testers do not take into account magnification such as would be caused by wearing plus lenses, nor minification such as would be caused by minus lenses.

In the illustrated embodiments, results of the test can be analyzed and interpreted automatically. For example, in some embodiments, visual fields are interpreted intraocularly and binocularly by comparing corresponding points in different quadrants of the same eye and of the other eye. When any particular test target or cluster of test targets is missed, the likelihood of abnormality is estimated by reporting the chances of that test target or cluster being missed in the age-matched and sex-matched normal population. This process results in each test target result being classified as normal (1), borderline (0) or abnormal (−1).

In some embodiments, point-for-point comparison with a panel of reference fields (e.g., homonymous hemianopia, bitemporal hemianopia, arcuate defect, nasal step, etc.) (or a test databank) provides a differential diagnosis, with relevant conditions being listed in order of their likelihood. In some cases, in a relatively brief screening test, results can be provided in the form of "normal" or "abnormal." In some implementations, when a test is performed as part of monitoring of a patient's condition, each test location can be scored as "improved," "deteriorated," or "unchanged." It should be appreciated that any number of any suitable qualifying and quantifying parameters can be used. A suitable visual representation of the results can be displayed in any format, e.g., as a plot indicating change in the patient's condition over time. In some embodiments, confidence scores are provided for test results, and recommendations on further testing can be included along with expected changes in confidence.

Test Results

Test results can be presented to a user (e.g., a healthcare professional) in any suitable format, such as an electronic format—i.e., on a display of the computing device, in a video, audio, or a combination thereof format. In some embodiments, test results include patient information, medical history information, and test session information. The patient information can include, for example, patient's name, date of birth, medical record number, gender, and/or any other suitable information. The medical history information can include, for example, clinical diagnoses (e.g., a prior diagnosis by a healthcare professional), diagnosis code number(s), and/or any other suitable information. The test session information can include, for example, date and time of test, test strategy, test diagnosis if available, result grid for each eye, test duration, fixation target interaction success (if applicable), name and address of a person supervising the test, departmental logo, reference to a test website, and/or any other suitable information. The result grid can display information on test targets that the patient saw in the form of empty spots or circles. Missed test targets can be displayed in the form of filled circles, with the color and intensity of the fill representing the color and intensity of the missed test target. The margins, color and intensity of the background zones can be shown (e.g., average for a paper printout and changing over time for the results presented in the form of a video). The result can also include fixation errors in a suitable format.

Regardless of the specific format in which the test results are provided, the results and any other related information (e.g., patient-specific information) can be handled and stored in conformance with requirements for electronic protected health information. Thus, the information is handled and stored in compliance with the Health Insurance Portability and Accountability Act (HIPAA).

Test Parameters

In the described embodiments, any property that varies across the visual field can be controlled, adjusted, and measured. Non-limiting examples the properties include contrast/brightness, binocular disparity, interocular suppression, movement, and color. The described techniques can also detect when an object has become salient within the visual field. Salient objects attract attention and cause orienting towards themselves. Orienting can be defined as a turn of the eyes and/or head towards the object that elicited it. Other detectable responses that coincide with or come after the orientation include the pupil response, EEG, and ERG, galvanic skin response, among others. Properties of objects that cause them to be salient in a bottom-up fashion (without instructions to the patient) include changes in local luminance (spots that are light or dark, for example) and motion. Properties that the patient will orient towards because of instructions, that cause them to become salient, include color (e.g. "look for red spots"), depth (e.g. "look for a target that is closer than the others"). In general, the "salience map" constructed within a person's visual system directs their visual resources towards objects of interest. These resources include both overt allocations of attention (head turns and eye movements) and covert allocations of attention—central nervous system switching to increase visual processing of a particular part of the visual field, or to detect a test target property of interest based on the task that the patient was instructed to do, such as responding to colored objects.

Fixation Target and Task

In the described embodiments, an interactive fixation target has properties such that, when it is displayed, the patient's attention is attracted to a particular point on a test area such that the patient is able to perform a continuous task successfully.

To enhance patient cooperation, a fixation target can be modified in various ways. In some embodiments, the fixation target can be in the form of a movable object, such as, for example, a car driving along a winding road, a fighter plane flying away (as it is viewed by the patient), or any other object which can be displayed in conjunction with a certain background. In some embodiments, test targets or stimuli are presented on a display when a head pointer at least partially overlaps with a fixation target (e.g., in the form of a circle) and when the head pointer follows the fixation target through a certain number of successive movements of the fixation target. A size, color and contrast of the fixation target are adjustable so that this visual tracking is possible only when the patient looks directly at the target. For example, the principle of Gabor Stimuli can be followed. In some embodiments, a pixelated grid allows generating fixation targets having various (e.g., complex) shapes, colors, color patterns, etc. In one embodiment, default diameters of the head pointer, test target, and fixation target are 0.5 degrees, 0.43 degrees, and 0.8 degrees respectively. In at least one embodiment, the test target can be in the form of a dark grey object (e.g., a spot) on a fixation target that is light-grey, so that the average light intensity of the entire target equals that of the background.

Non-limiting examples of various tasks that a system in accordance with the described techniques is configured to administer are described below.

High Acuity Pattern (HAP) Discrimination Task

Figure 7A:
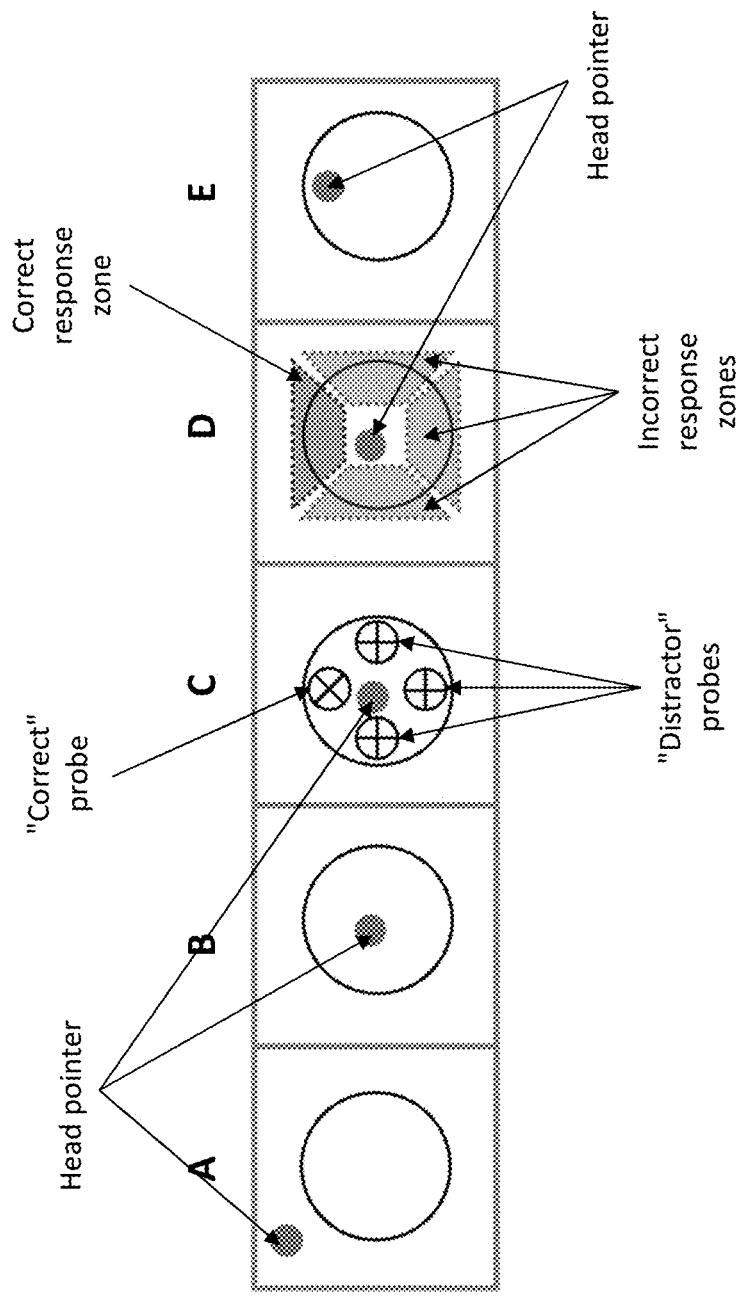
FIG. 7A is a schematic illustration of one example of visual information that can be presented as part of a high acuity pattern determination task, in accordance with some embodiments.

FIG. 7A illustrates an example of visual information that can be presented as part of a high acuity pattern determination task. In this example, once a head pointer is within a fixation target, four probe locations within the fixation target are briefly filled with objects, such as with one "correct" object or probe and with three "distractor" objects or probes. The patient attempts to move the head pointer to the correct probe. If any of the distractor probes are "hit" by the head pointer (meaning that the patient moves his/her head such that the head pointer visible to the patient overlaps with the distractor probe), the task is repeated, in order to guarantee that fixation is in a neighborhood of the task. Because the probes are of a small size and are located close to each other, this task cannot be done without proper fixation on the probes.

FIG. 7A illustrates schematically a sequence of visual features that can be presented on a display device (e.g., on a display of a head-mountable device, a smartphone, a smartwatch, a computer, a TV, etc.) to a patient, in accordance with the described techniques. Section A of FIG. 7A shows a pointer (which can be shown in red or another color) and a fixation target in the form of a circle, with the pointer and the fixation target being located in a detection zone. The pointer can be a head pointer if this information is presented to a wearer of a head-mountable device, or another type of pointer, such as, e.g., a joystick pointer, a button pad pointer, etc. In Section A of FIG. 7A, the fixation target has just become visible (because the patient appropriately moved the head pointer into a detection zone) but the pointer is still located outside the fixation circle. In Section B of FIG. 7A, the patient has moved the pointer into the fixation target such that the pointer is disposed within the circle representing the fixation target. Once the pointer has been moved into within the fixation target, four probes are displayed within the fixation target—the correct probe ("x") and three "distractor" probes ("+"), as shown if Section C of FIG. 7A. The correct probe is the probe towards which the patient should move the pointer. The four probes are displayed for a predetermined period of time such as, in at least one embodiment, 50 milliseconds. However, the probes can be displayed for any other period of time.

Section D of FIG. 7A illustrates schematically four response zones which are not visible to the patient. One of the four response zones includes the correct probe. In Section E of FIG. 7A, the pointer is shown after it has been moved towards the correct probe. Thus, the correct fixation for the test target has been confirmed.

Figure 7B:
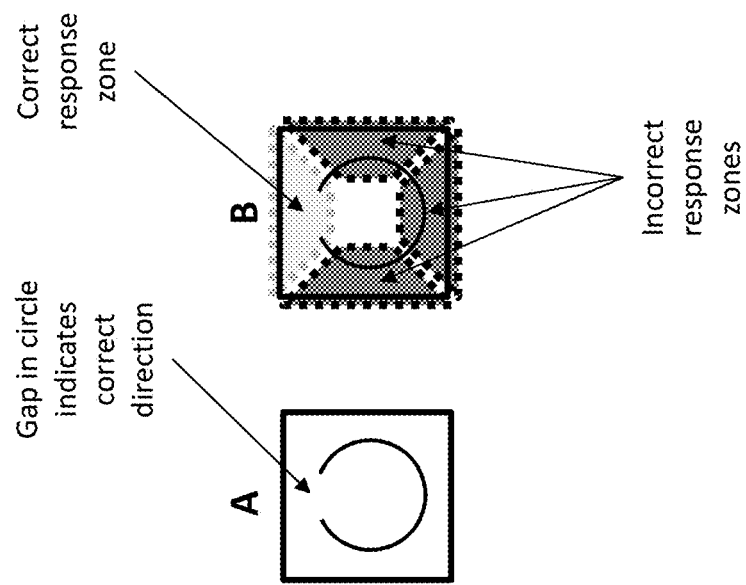
FIG. 7B illustrates a simplified probe using the rotational orientation of a single figure requiring high acuity vision, such as a "Landolt C".

FIG. 7B illustrates a simplified probe using the rotational orientation of a single figure requiring high acuity vision, such as a "Landolt C," as illustrated in Section A of FIG. 7B. Section A corresponds to the view that a user sees during the test. Section B of FIG. 7B illustrates four response zones that the patient can select. In this example fixation would be verified when the patient identifies that the gap in the "Landolt C" is at the top of the figure, and, for example, moves the pointer to the top response zone. The zone can be one side of the square that contains the "Landolt C," so that passing the pointer through the top side of the square satisfies the requirement for fixation.

Circle in Circle Task

This task is administered such that a patient is required to maintain a pointer (e.g., a head pointer in the form of a spot) within a fixation target (e.g., a circle). The fixation target can be in the form of the circle that is displayed as moving randomly in horizontal and vertical directions. The spot is controlled by the patient moving his/her head, moving the patient moving a hand-held device, or the patient moving his/her eyes in a required direction. The level of the task (e.g., its difficulty) can be adjusted automatically (e.g., within a predetermined range) according to the success with which the patient is able to keep the pointer within the circle. For example, the level of the task can be adjusted based on a ratio of a duration of time when the pointer is located within the boundaries of the circle and a duration of time when the pointer is located outside of the boundaries of the circle Tracing Task The fixation task is administered such that a patient traces out a small object of a certain shape (e.g., letter, number, square, triangle, circle) by using either an input device, such as any suitable controller (e.g., a joystick, button, pointer, head pointer, etc.). The object is small enough so that the task can be performed accurately only if peripheral vision is exploited.

Small Spinner Task

An object such as, for example, a small plus-sign of an appropriate correct size, can be displayed as spinning on a display. A patient can only determine the direction of the spin with his/her foveal vision. A user input is acquired from the patient, with the goal of determining whether the patient can discern the way in which the object is spinning, such that the system can determine whether the patient is using his/her fovea. If it is determined that the patient is using his/her fovea, a test target (test target) can be displayed (flashed) in a desired location on the display corresponding to a location in retina that is being tested.

Grouping by Common Fate Task

A flashing target can be flashed (e.g., displayed for a relatively brief period of time, such that the patient perceives it as being "flashed") in a center of a display (i.e., in the patient's central vision), and another target can be flashed in patient's peripheral vision (i.e., in an area of the display that is peripheral to the center that is the focus. The task can be administered such that the patient is required to determine whether the task in the center is flashing synchronously with the target in peripheral vision. The target in central vision can be maintained in the same position throughout a test or a session (part of the test), whereas targets in peripheral vision can be flashed at varied locations. The target in central vision can be, for example, a small object and it can have balanced luminance contrast. In some implementations, more than one type of targets can be flashed in peripheral vision, for example, at different rates or at another phase. For example, one type of target can be flashed at one rate and another type of targets can be flashed in peripheral vision in a different rate. The target of one type can be different from a target of another type by size, color, shape, luminance, or by any other one or more properties.

Luminance Balanced Fixation Target Task

A test can be administered such that a fixation target is displayed on a display that a patient is expected to see using his/her foveal vision. Such target can be luminance balanced and it can be displayed such that its color alternates from frame to frame, in which case the target is visible in foveal vision while remaining invisible to peripheral vision. The target can be visible in foveal vision even without moving a pointer, or moving the pointer only partially towards a fixation target. The target can be in the form of, for example, a small fixation spot centered or not centered within a larger circle, the larger circle being easily visible so that the patient can find the fixation spot within his/her visual field.

In addition, a property of the fixation target (e.g., a rate at which the fixation target is flashing, the temporal phase of the flashing, color, motion direction, etc.) can be paired with that of a peripheral target. In this way, the task can be administered such that the patient is required to verify that he/she is fixating on the fixation target and is also using one or more properties of the fixation target to select one of one or more peripheral targets to orient towards. Detecting of the commonality (e.g., one or more identical or similar property) between the fixation target and the peripheral target can be based, e.g., on an instruction provided to the patient in a suitable format. Additionally or alternatively, the identification of common properties among the fixation target and the peripheral target can occur as an automatic response to the manner in which the targets and other information are presented to the patient. In this way, this task can be similar to the task of grouping by common fate, discussed above.

Figure 8:
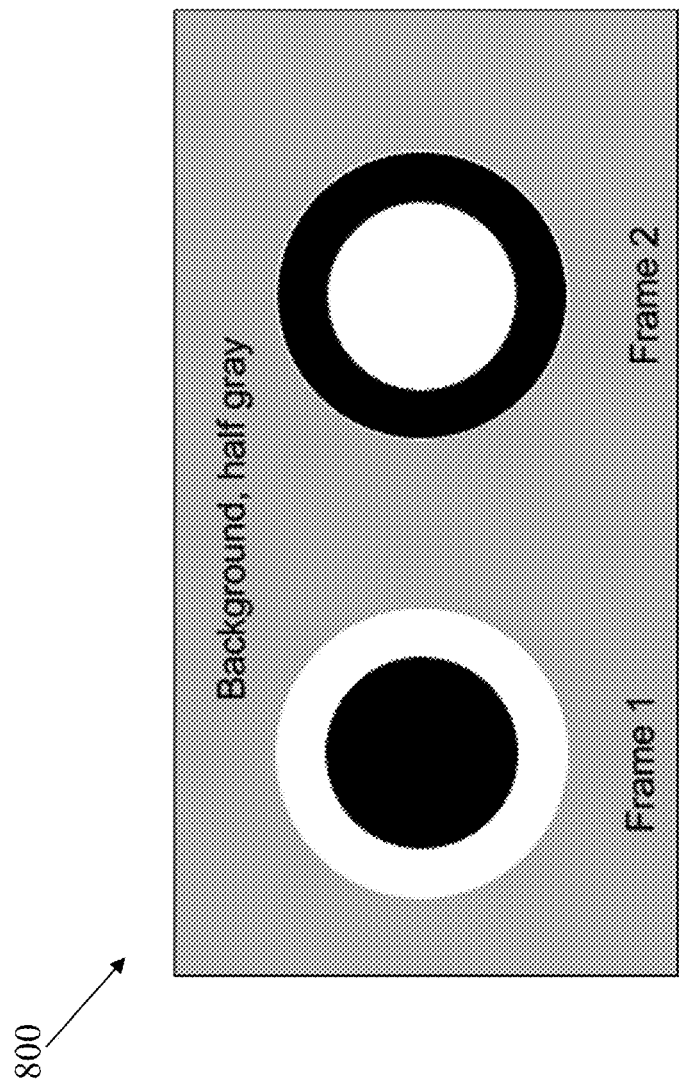
FIG. 8 is a schematic illustration of one example of a scene that can be displayed on a suitable display, in accordance with some embodiments.

FIG. 8 illustrates an example of a scene 800 that can be displayed on a suitable display, the scene including a background ("half-gray," in this example) and a fixation target. As shown, the fixation target has changed its colors (in this case, the way in which it is colored) from Frame 1 to Frame 2. Total luminance of the scene remains constant as the test target flickers.

Test Targets

Various types of test stimuli or test targets can be rendered on a display of a head-mountable VR device or another device, in accordance with the described embodiments. Different types of test targets can be used to probe different attributes of visual processing. In some embodiments, the test targets can vary by size, texture, luminance polarity (e.g., they can be dark on a light background, or vice versa), spatial distribution, color, duration, temporal characteristics, shape, pattern, location on the display, and by other parameters.

The test can have various sizes. In some embodiments, a size of the test target can be adjusted to use larger dots in peripheral vision where resolution is not as good as it is in central vision. Larger targets can be used in tests intended to be administered to patients with advanced retinal disease—such patients may not be able to see small targets. The larger targets can be displayed as part of an adaptive testing procedure, which involves increasing the size of the targets during testing until the patient can see them.

The test targets can have various textures. In some embodiments, test targets are in the form of distributed dots or texture. Persons with amblyopia do not integrate visual stimulation normally across space. It has been observed that such persons show deficits in "global motion perception" and "global form perception" even when viewing test targets with their non-amblyopic eye. These deficits (defects) may not be uniform across the visual field and can thus be tested by region.

The test targets can be spatially distributed on a display in various manners. In some embodiments, a spatial distribution of the test targets can be in the form of a lattice of targets, such as, e.g., a square lattice, hexagonal lattice, or another type of lattice. The lattice can be uniform in size or anisotropic. For example, in one embodiment, it can be denser in central vision, and it can be presented with a target that is being made to disappear or change its appearance. The patient will be asked to detect the target.

The test targets can have any suitable color or a combination of colors. Some people with anomalous color vision show differences in the mix of cone photoreceptor types between the eyes, or between regions of the eyes. People with normal vision express different ratios of the three cone classes for color vision, and these may vary geographically across the retina or between eyes. This can be measured with a visual field test using colored test targets. For example, the ability to discriminate red test targets from green test targets requires that L or M cones be present at the tested region of the visual field. Also, the test stimuli can differ from the background color along the blue-yellow color axis. Blue-yellow color perimetry can be more sensitive than white-on-white perimetry for early detection of glaucoma.

The test targets can be displayed for any suitable duration of time, and they can have various temporal characteristics. In some embodiments, test targets can be displayed or "flashed" very briefly, such that a test target is made to appear in a location on a display corresponding to one specific retinal location, because there is not enough time for an eye movement to displace the image on the retina. Test targets with greater duration, or that flash on and off, can be easier for a patient to detect. However, there may be uncertainty in the maintenance of retinal location of the image. In some embodiments, eye position is monitored, such that multiple retinal locations of at least one test target can be inferred.

The ability to discriminate flicker from non-flicker depends on the "flicker fusion frequency" or "flicker fusion rate" and the temporal frequency of flicker that can be discriminated from a steady state test target (of the same mean luminance) depends on retinal location, state of adaptation to the overall light levels, and factors that differ between individuals and perhaps between the eyes of an individual, especially an individual with disease. Asymmetry between the eyes in the flicker fusion rate at a particular location in the visual field may be diagnostic of disease causing one eye to have more sluggish responses than the other, and thus a lower (worse) temporal frequency threshold for flicker fusion.

The test targets can have various shapes and patterns. Non-limiting examples of shapes include geometric shapes such as, e.g., spots, circles, squares, and triangles. The test targets can also be in the form of faces of people or animals, photographs, cartoons, or animated objects including animals or animated faces. Furthermore, a patient may be better able to complete their tests if targets presented to that patient have shapes that are of interest to the patient. This approach may be especially well suited for administering tests to children. Thus, test targets presented to a child can include cartoon characters, images of animals, toys, faces of people familiar to the child, etc. In this way, a test can be presented in the form of a game to a child. Any visual character of test targets presented to a patient can be selected and, if desired, adjusted, based on the patient's age, gender, preferences, and may other factors, etc. In addition to creating greater interest, shapes can be used to test cortical processing. For example, a person with prosopagnosia may not discriminate faces well, and a person with autism spectrum disorder may not discriminate some of the emotions depicted by targets in the form of images of faces.

In some embodiments, any test target parameter can be varied automatically, for example, through control by a staircase or any other adaptive procedure. One or more parameters of a test target can be set before a test procedure begins. For example, a suitable user interface of a computing device can receive user input (e.g., from a clinician) via one or more slide bar or any other input feature rendered on the user interface. Additionally or alternatively, parameter(s) of a test target can be adjusted in real time, as the test (task) is being performed by a patient. In some embodiments, in advance of a test, by a clinician. In some embodiments, results of the test can be made visible to the patient, including, in some cases, in real time.

Test targets are displayed in various locations of a display visible to a patient. The locations can be determined using a testing algorithm. The locations can be predetermined. Additionally or alternatively, in some embodiments, the locations can be adjusted in real time, e.g., based on the patient's current performance of the test. Test targets can be shown only to one eye or the other, or binocularly to both eyes at once, such that a single binocular map can be generated.

In some embodiments, test targets can be created to make overall luminance against the background constant. For example, on a gray background, the targets can be white-and-black, so that a person with poor spatial resolution will not be able to see the modulation of luminance in the target.

Test Background

In some embodiments, a test background has a single color. In other embodiments, the test background has more than one color, and it can have various patterns. In some embodiments, the test background can include concentric areas, with the width of each area being adjustable in every meridian by dragging its edges. The background color and brightness of each area can be adjusted (e.g., by sliding pointers on slider bars, or via any other input features). Various visual properties of the test background can be set before the test or at least some of the properties can be adjusted in real time, during the test (manually or automatically). In some implementations, the test background can be different at least one aspect for each test target presentation.

Furthermore, in some embodiments, the test background has visual features, such as, e.g., a still image, a movie, or an entire three-dimensional scene. The test background can be in the form of a computer game. One or more features included in the test background can have the brightness and hue of the entire feature or a portion thereof change over time, which can be controlled automatically.

Test Duration

A test in accordance with the described techniques can be controlled to begin and end in any suitable manner. The test can begin upon a suitable trigger, such as, e.g., upon user input instructing the test system to begin displaying images (test targets, fixation target, pointer on a background, etc.) on a display visible to a patient. In some embodiments, it can be determined whether to terminate the test based on one or more of the following: (a) when all test targets have been presented, (b) when a particular test target has been missed, or (c) after a specified test duration. Other factors can be used additionally or alternatively to determine when to terminate the test. The test can be executed in an automatic mode. In some implementations, a test can be administered to determine a probability of developing one or more diseases by a patient, and the test can be executed until a predetermined certainty or probability regarding the disease(s) affecting the patient's vision has been reached.

Test Laterality

In some embodiments, a test can be administered such that both eyes of a patient are being tested simultaneously, with test targets being presented to each eye. This can be done in a semi-random manner (e.g., randomization of each left-right pair of). In some embodiments, however, a test can be administered such that one of the patient's eyes is being tested. Laterality, color, and brightness of a field presented to the fellow (unexamined) eye can be selected as appropriate for a particular test. Furthermore, in some embodiments, the test can involve presenting test targets to ether one or both eyes of a patient, e.g., in an alternating or another manner.

Response Modes

The described techniques can determine whether the patient has seen a test target in various ways. For example, this can be performed using a discrete-trial subjective mode, discrete-trial objective mode, a continuous tracking mode, or in any other manner.

Discrete-Trial Subjective Mode

In a subjective task, a patient follows an instruction to report what he/she sees during the test. This requires that the patient be aware of the test target. The patient indicates his/her awareness of the test target by moving his/her head, hand-held pointer (e.g., "pistol"), or patient's eyes towards a location of the test target (the test target having disappeared by the time the patient reacts). This movement is signaled by the gaze pointer moving with the patient's head, eyes, hand-held device, or in another manner. Detection of the test target is indicated by the gaze pointer entering an invisible detection zone (or "hit-zone") encompassing the test target. The size and shape of this detection zone are adjusted for each test target presentation, automatically or manually (e.g., via a user interface presented to a clinician supervising the patient being administered the test). In some cases, the detection zone can be in the form of a triangle with its apex pointing towards the fixation target, though it should be appreciated the detection zone can have various other shapes, and it can have various sizes.

In some embodiments, when the test target is determined to be detected by the patient, a fixation target is displayed on the display viewed by the patient, and the process is repeated. Alternatively, in some embodiments, a new fixation target appears closer to the tip of the "hit-zone" and where the patient's gaze is directed.

If the test target is determined to be not detected by the patient within a specified time, the prior fixation target may remain being displayed, and a next test target is presented, either in the same location (e.g., a "stronger" test target, such that one or more of its properties are adjusted with the goal of the test target being more visible to the patient), or in a different part of the patient's visual field. Also the fixation target can be moved after the stimulus is determined to be not detected.

Non-limiting examples of subjective inputs include patient's head, eye or another movement, inputs received via one or more of a controller device, positionally tracked controller, via patient's voice, mouse and/or keyboard, touch interface, etc.

Discrete-Trial Objective Mode

In an objectively-measured task, the patient responds automatically to a test target, which may be a "natural" response—e.g., movement towards or another reaction to appearance of a new test target. This may not require a prior training of the patient. Also, the patient may or may not be aware of the test target. The objective mode can use eye tracking (or other sensors) to automatically detect whether or not the patient sees a test target and where the patient's gaze is fixating. Thus, the patient may not be required to provide an explicit indication that she/he saw the test target.

In some embodiments, individualized adaptive Bayesian response measurements can be acquired. A patient's response profile in an objective mode can be generated by measuring one or more of the response metrics. This can be performed, e.g., during a training mode administrated to the patient before the test begins. The training mode can involve administrating to the patient an activity similar to the actual test, or another type of activity intended to acquire user input so as to collect appropriate response metrics. Measurements acquired during the training mode can be used to generate priors that are used in the testing mode to determine if response metrics acquired during the test mode should indicate as a "seen" or "missed" test target. This can increase accuracy of results of the testing. For example, some people turn their eyes towards a target when the see it, and some turn their head and eyes. The described techniques can determine for each individual when the target has been seen, based on a combination of measurements of these responses (and, in some cases, in combination with other responses, e.g., pupil dilation). The response metrics can be adjusted based on results acquired during the testing mode. In this way, as the patient is administered tests, accuracy of the interpretation of the results can increase from test to test. The response metrics can be adjusted for each patient, for each test, and/or in any other manner.

Continuous Tracking Mode

In some embodiments, in a visual field test, peripheral test targets can be presented, on a display viewed by a patient briefly, to ensure that the test target is not discovered by the patient by the process of visual search. In some cases, the test target can be displayed on the display for about 0.5 seconds, such that the patient is typically able to "find" that target on the display. Alternatively, the new target can appear at the desired retinal location, and remain on the screen for as long as it takes the patient to find it using a search strategy. The patient's task can be to look at the target, in which case the dependent response measurement is eye position; or the task can be to point with the hand or a head-pointer at the target, in which case the dependent response measurement is a hand or head position. Whether the target was detected at onset (or how quickly it was detected) can then be determined based on the measurements acquired during tracking. For example, the patient may initiate movement of his/her head pointer towards the target with a very short response latency in the case of a target that was seen, but require much longer for a target that was not see until after the patient searched for it using eye movements.

In some embodiments, a tracking mode task can require performance of the tracking over time for a moving target that "jumps" to new locations. For example, the task can be to keep the head pointer inside a target circle that moves across the screen on a motion path with random components. This task requires fixation. To test a new location, the target circle jumps to that location in the visual field and the patient resumes tracking as soon as the patient sees the target. For example, in at least one embodiment, the delay in responding to the onset of a new target can be measured as the temporal offset in the peak probability in a cross-correlogram, between the dependent measured signal and the test target. This can be done, for example, as described by Bonnen, K., Burge, J., Yates, J., Pillow, J., & Cormack, L. K. (2015). Continuous psychophysics: Target-tracking to measure visual sensitivity. Journal of Vision, 15(3):14, 1-16.

Testing Approaches

In some embodiments, a Bayesian approach in used for visual field testing, which uses available information to determine locations to test in the visual field. In some embodiments, before a test is administered, patient data can be updated and locations to test are determined based on the update. A Bayesian classifier can be used to determine current probability of having each disease. The test can be manually ended, set to a timer, or it can be configured to end when a specific confidence has been reached.

Information used to generate prior probability distributions is stored in a suitable memory location of a computing device. In some embodiments, a database of test data (e.g., a database of Humphrey visual field (HVF) results) can be generated and used to generate the prior probability distributions. In some embodiments, a Monte Carlo Markov Chain (MCMC) Bayesian approach is used to construct probability distributions and to measure a new point in the field.

In some embodiments, predictor and classifier modules can be employed, which can be implemented in suitable computing software. In some embodiments, a predictor module receives patient data as input and generates a two-dimensional probability map across the visual field. In some cases, misses (i.e., test targets not seen by the patients) or hits (i.e., test targets seen by the patient) at each location are predicted. In some embodiments, a fixed brightness at each location is used as a cutoff normalized across the field to account for normal sensitivity differences between central and peripheral vision based on a database of visual field tests.

Figure 9:
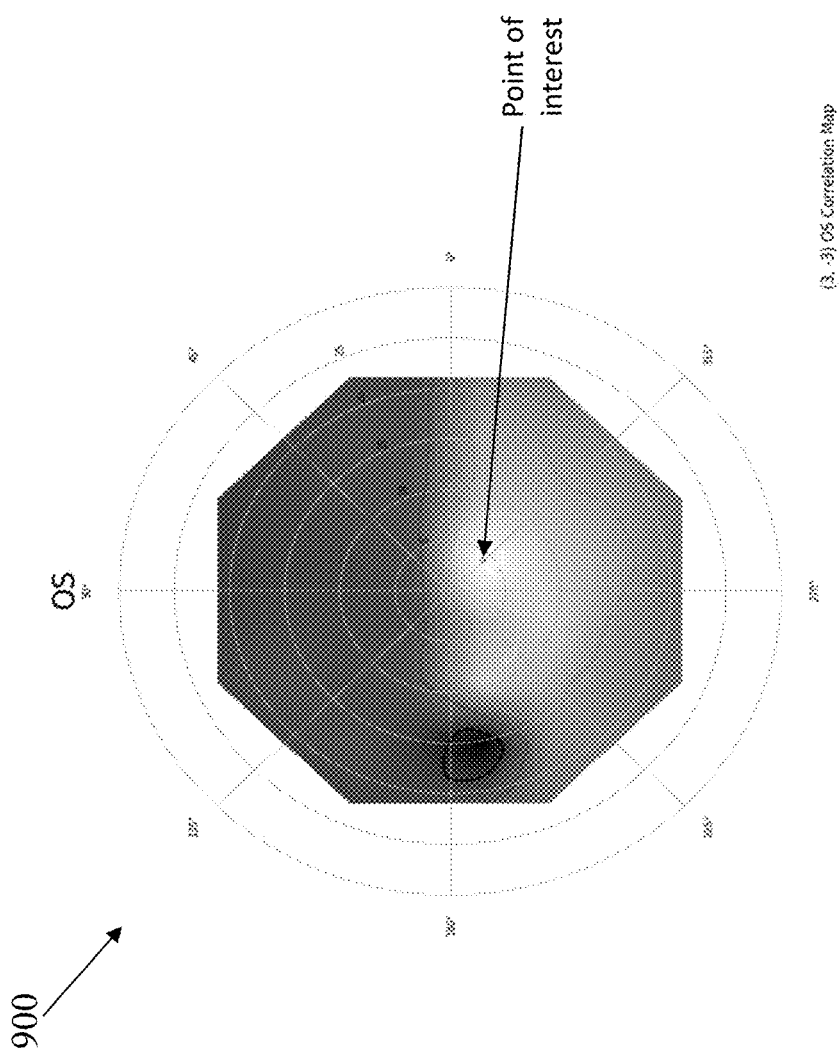
FIG. 9 is an example of a correlation map that is generated for a single point on a visual field, showing correlation between that point and each of the other points, in accordance with some embodiments.

The predictor module can also use correlation maps. Once a single point in the visual field is measured, a correlation map matching the demographic data can be generated. The correlation map can indicate how correlated each point in the visual field is with other points, given the patient's current probabilities provided by the classifier. This information can indicate which points will provide the highest likelihood of learning new information for this patient. FIG. 9 illustrates a correlation map 900 for a single point ("Point of interest") on the visual field, showing how correlated each other point is to that point.

Once a map of the probability that a patient will miss/see a test target at each location in the visual field is generated, this map can be used when measurements are acquired. The acquired measurements can be added to the prior knowledge collected for that patient, and a classifier module can be executed. The classifier module uses information acquired on the patient to produce a set of probabilities for potential diagnoses. The classifier module can be a neural net, boosted decision tree, or any other classifier. More than one classifier can be. A confidence score will be generated in connection with each result. The probabilities produced by the classifier module are also used to update the prior used for the predictor module.

In addition, a Bayes classifier configured to detect a particular disease can be different from a Bayes classifier configured to estimate target thresholds at all tested locations in the visual field. In the latter case, the goal can be to construct a visual field map that characterizes ability to see at multiple locations in the visual field under some constraint, e.g., no more than a certain number of target presentations, a time limit for the test, etc. For the Bayes classifier configured to detect a particular, the goal is to estimate a probability that the patient has a particular condition, and this may not require estimating thresholds, or it may not require estimating threshold at all locations in the visual field.

In some embodiments, a continuous approach to visual field testing is utilized. For example, some embodiments include modeling attention to spatial location, boredom, ability to fixate, and response time as specific sources of variability that would affect an individual's performance on a test. These factors can be taken into account when performing a probabilistic test to screen for glaucoma or build a field map (or track progression over time). Relatively straightforward target detections (e.g., near fovea or where there is known to be no scotoma) can be used to characterize these aspects of the observer-responder.

In some embodiments, a task can be administered that permits testing multiple locations in the patient's visual field at once—e.g., an indication acquired from the patient as a result of presenting test information to the patient will depend on more than one (or all) of the locations being tested. In some embodiments, ability of people to fixate easier on images of some objects than others can be exploited. For example, empty boxes can give steadier fixation than solid dots. Also, people tend to fixate on human faces at the highest-information place—between the nose and eyes. Thus, in some embodiments, human faces (e.g., faces of actual people, fictional or computer-generated faces, etc.), and/or specific areas of the faces can be used for accurate fixation. In some embodiments, faces familiar to the patient can be acquired from the patient or from social media sites.

Continuous tracking can be combined with step changes in position. There can be one task to do if a patient needs to track a target that jumps to a new location. The accuracy of tracking can be used to determine fixation, and the patient's tracking can be detected via head tracking, a suitable controller, or a pointing device. In some embodiments, tracking can be performed with a patient's finger using a tracker such as, e.g., the Magic Leap or optical tracking sensors (e.g., a sensor built into a Microsoft VR headset) that do not require wearing a trackable badge on the finger. In some embodiments, a tracking device can be worn by a patient. The headset can be an augmented reality (AR) display that allows a person wearing the headset to see his/her real finger.

In some embodiments, a task can be to keep a pointing device (e.g., a tracking spot) inside a target (e.g., in the form of a circle) that moves in a random manner. At certain time intervals (e.g., about 1 second), the target "jumps" to a new location (that is being tested). If the patient sees the target, the pointing device is moved towards the target. If the patient does not see the target, the patient starts searching his/her field of view for the target, which can be detected as one or more of a response time in the pointer's movement, the direction in which the pointing device is moved by the patient, and detection of an eye movement (response time and, optionally, also direction of motion). In one embodiment, if the target moves along a linear trajectory, one could use the moment at which it is seen, meaning that it has emerged from the scotoma, as a way to do dynamic perimetry, provided the response is made within about 200 msec or so, which would allow for about 80 msec perceptual processing plus about 100 msec to initiate the saccade. Fixation can be determined during the tracking task, followed by a period of only minimal eye movement during the about 150 msec after target offset (and its simultaneous or asynchronous re-appearance elsewhere), so that moving the eyes, or the pointer, to the new target within 200 msec serves be a reliable indicator that the new target was seen at the retinal location being tested (based on the vector from the previous target at fovea to the new peripheral target). This procedure can be repeated until the visual field is mapped.

In some embodiments, as mentioned above, a target can be a face. Accurate face-tracking can be automatic and reliable, in which case an easy task can be used in central vision, which would allow for more visual attention to be allocated to the peripheral visual field and improved measurements of sensitivity.

In some embodiments, a "standard" supra-threshold test can be administered. In such embodiments, N supra-threshold, black-on-white test targets can be presented in the central 24-degree field in order of priority until all are examined or until a specified time (e.g., about 180 seconds per eye) is reached, whichever occurs first. When all points have been examined, any missed points are re-tested except in clusters of missed points (e.g., greater than a certain number of adjacent points). Blindspot test targets that are seen can be re-tested. In some embodiment's, in the standard supra-threshold test, prioritization can be as follows: Category 1—4 quadrants (i.e., 45-degree meridian) at eccentricity of 24-degrees; Category 2—Inferior hemisphere at eccentricity of 16-degrees; Category 3—Superior hemisphere at eccentricity of 12-degrees; Category 4—blind spots at eccentricity of 15.5 degrees, 3-degrees above/below horizontal; Category 5—Nasal area, 15-degrees above and below horizontal at eccentricities of 16, 20 and 24-degrees; Category 6—paracentral zone at eccentricity of 4-degrees and at 45-degree meridians. Test targets within each category can be randomized.

In some embodiments, a detailed supra-threshold test can be administered. If specified test duration is not reached (e.g., 5 minutes per eye), the standard supra-threshold test continues by testing points intervening between seen and missed test targets. The test stops when at the specified test duration.

In some embodiments, a brief supra-threshold screening test can be administered. The standard supra-threshold test stops after a specified duration or if any test target is missed twice, such a missed test target being re-tested immediately after one test target in the next location is tested. The normal blind spots are tested.

In some embodiments, a threshold test can be administered. The standard threshold test is performed with weak stimuli test targets (e.g., light grey). Any missed points are re-tested with a moderate stimulus test target (e.g., dark grey). Any points missed a second time are re-tested with a strong stimulus test target (e.g., black). The intensity of the weak stimuli will be based on normal values (i.e., healthy individuals matched for age and gender).

In some embodiments, a chloroquine retinopathy screening can be administered. For example, yellow-on-blue stimuli are presented at 4-degrees eccentricity in all meridians, with missed points being re-tested unless missed more than 2 adjacent points are missed.

In some embodiments, points between previously-missed and previously-seen test targets are examined first, with the test then proceeding according to the strategy used previously.

In some embodiments, pairs of test targets from each category are presented simultaneously with one test target in each vertical hemisphere (i.e., medial and lateral). The pairs are randomized (e.g., supero-temporal and supero-nasal, supero-nasal and infero-temporal). The patient is required to look at both test target locations being free to choose which location is looked at first.

In some embodiments, a constriction test can be administered. For example, test targets are presented only in 45-degree meridians and in nasal areas 15-degrees above and below horizontal at 4-degrees eccentricity, then 12-degrees, then 20-degrees, then between seen and missed points at 8-degrees, then 16-degrees.

In some embodiments, a blindspot test can be administered. With black-on-white, small test targets, the center of the blindspot is tested in vertical, horizontal and oblique meridians with respect to center of blindspot, with each test target separated radially by 2 degrees, with radial points between seen and missed points being tested.

The described techniques involve presented information that is intended to train patients to perform various tests. In this way, text, still images, animated graphics, speech and information in any other format (or a combination of formats) can be used to educate patients as to how to perform the test, what is the visual field, what causes visual field loss, etc. The training can also involve administering a training "test" to the patient, before an actual test is executed. Information can be presented on a personal computer, smartphone, tablet, smart watch, or on a virtual reality device that is worn by the patient during the test. Also, the described techniques involve presented training and educational information to clinicians.

Figure 10A:
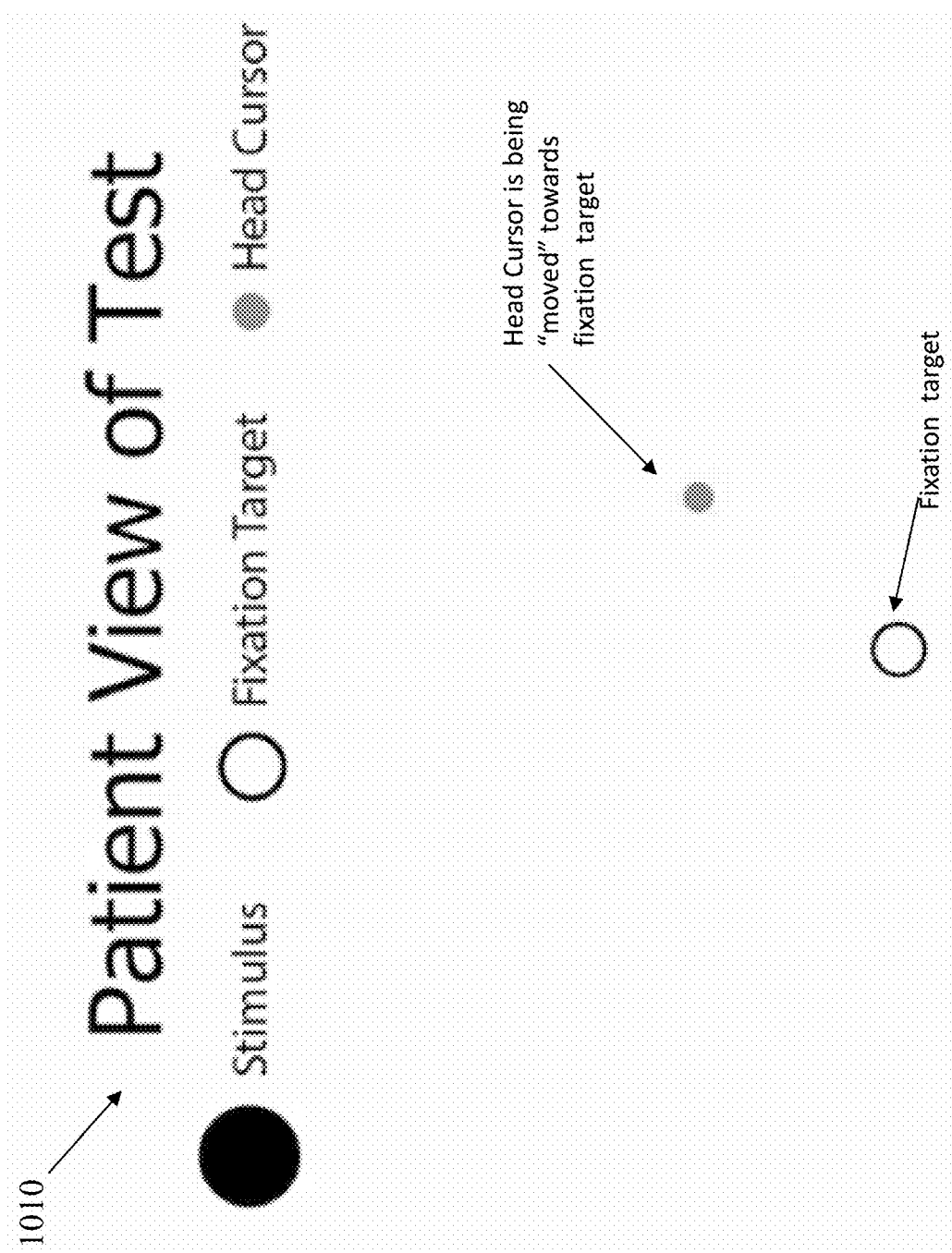
FIGS. 10A-10C are schematic illustrations of one embodiment of a method of testing a visual field of a patient using a pointer displayed in a VR environment of a display of a head-mountable device, in accordance with some embodiments.
Figure 10B:
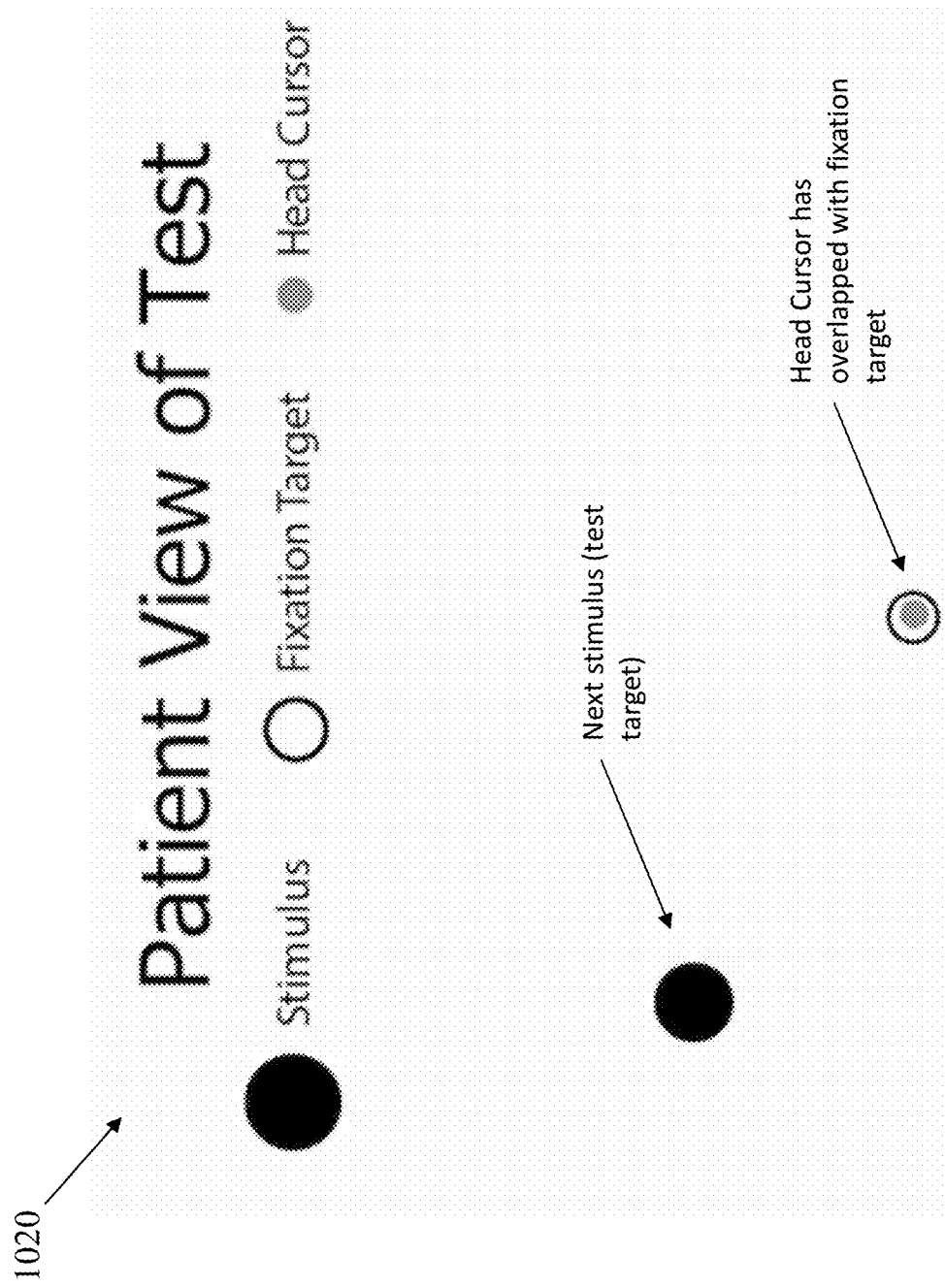
Figure 10C:
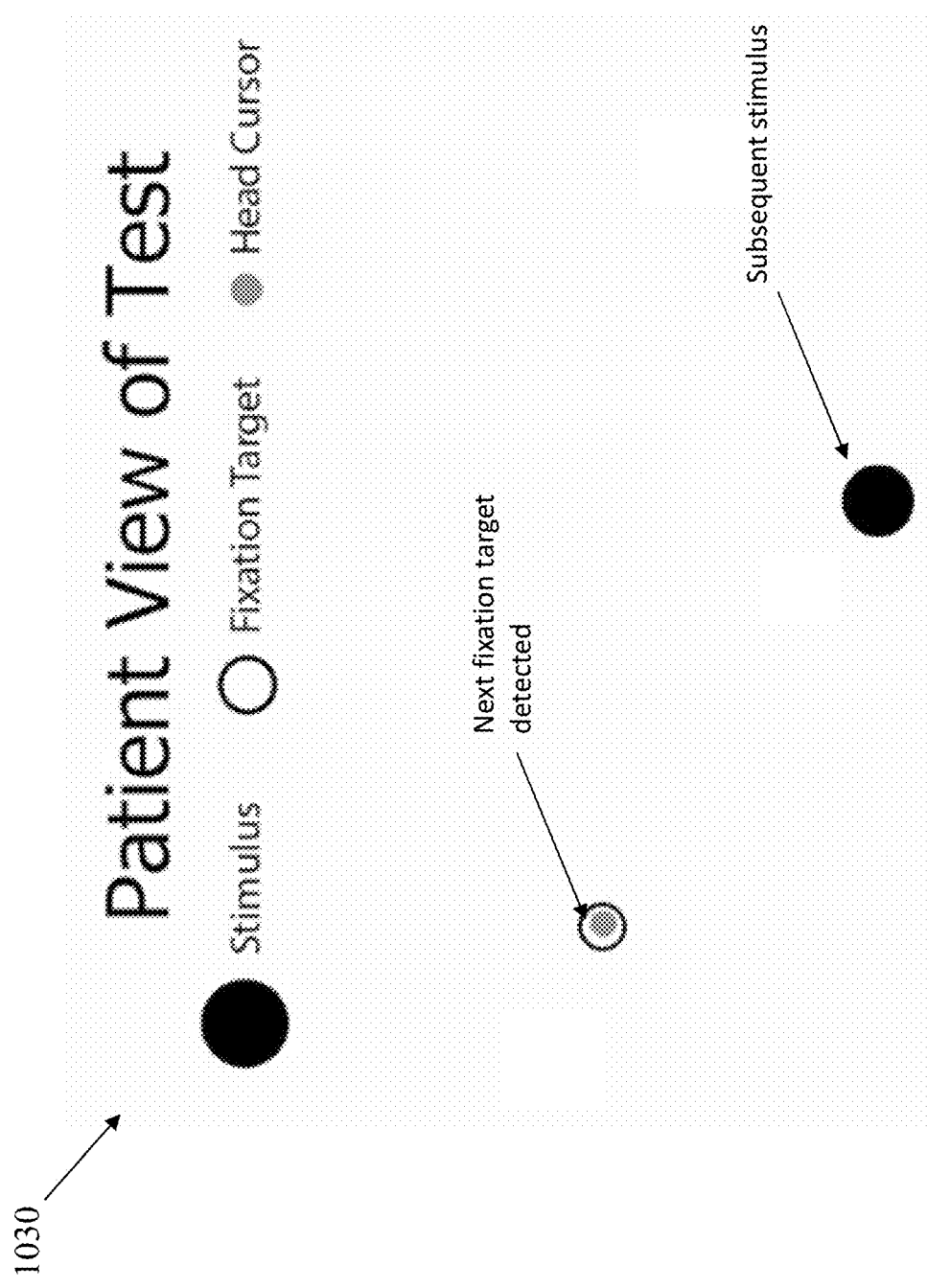

FIGS. 10A-10C illustrate one embodiment of a method of testing a visual field of a patient using a pointer (e.g., a head pointer or head cursor) that can be displayed in VR environment of a display of a head-mountable device. The views 1010, 1020, and 1030 shown in FIGS. 10A-10C is a view as seen by the patient during a test. The patient moves the head pointer (a dot, in this example) towards a fixation target (e.g., a circle having a diameter that is larger than a diameter of the head pointer) rendered on the display, as shown in FIG. 10A. This can occur, for example, when a prior test target was displayed and the head pointer is moving towards the location where the prior test target was displayed. Alternatively, the fixation target can be a first fixation target displayed, in this example, on a VR display. As the head pointer at least partially overlaps with the fixation target, a next test target or test target appears. Thus, as shown in FIG. 10B, in this example, once the head pointer is within the fixation target, a next test target is rendered. If the head pointer starts moving towards where that next test target has been displayed, it is determined that the patient saw this next test target; and the next fixation target appears in the vicinity of the location where the next test target has just appeared. FIG. 10C shows the patient's view once the next fixation target was detected (i.e., in this example, the pointer has been moved to be displayed within that fixation target), and a subsequent test target is displayed. The process can thus continue until all test targets that are intended to be displayed in accordance with this test have been presented. Each of the displayed test targets can be categorized as detected or missed, based on a determination of whether the head pointer was moving towards that test target when the test target was displayed.

Figure 10D:
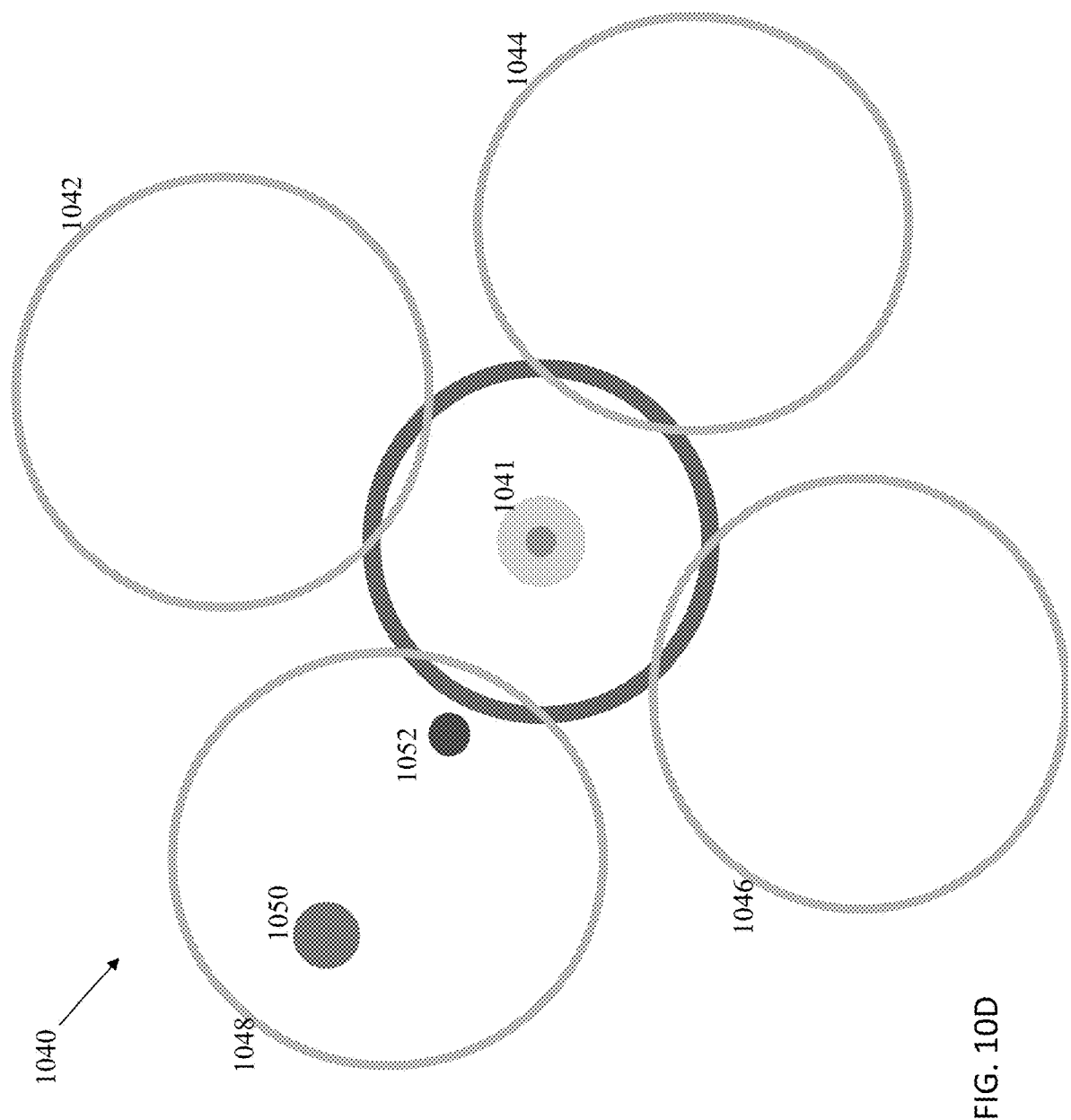
FIG. 10D illustrates a test for which a patient may respond by specifying one of four possible circular regions for the location of a test target.

Alternatively, the patient may respond by specifying the location of the target at one of two or more locations. FIG. 10D shows an example in which four responses 1042, 1044, 1046, 1048 are possible on each trial. The target is flashed at the location 1050 shown by the solid dark gray spot. Simultaneously with the target or preceding the target or following the target, or any combination of these, four response zones 1042, 1044, 1046, and 1048 are displayed. While fixating on the fixation mark 1041, the patient sees these response zones, shown here by four gray circles 1042, 1044, 1046, and 1048. The patient can respond by moving the cursor into one of these response zones or by failing to move the cursor into one of the response zones within some specified period of time, such as 2 seconds. The response zones can be of a number other than four, and they can be regularly spaced as in FIG. 10D, or they can be irregularly spaced. In this example, the head cursor 1052 has been moved into the correct zone that previously contained the target. It is not advisable to use an odd number of regularly spaced response zones because, in that case, the patient can sometimes guess the correct zone as being a zone that is to the right or left of fixation, in case of presentation of the target in the normal physiological blind spot.

FIG. 10E shows an example in which there are seven possible responses. In this example, there are six sectors defined by separating lines 1074 into which the cursor 1078 can be moved to select the location of the target 1076, or the patient can wait until the end of the trial without selecting any of the displayed sectors corresponding to regions 1062, 1064, 1066, 1068, 1070, 1072. The lines 1074 that separate the sectors are shown to the patient. In addition, as shown by the colored regions with dashed-line boundaries, the boundaries of the sectors can be extended towards the fixation mark 1061 to make it easier to respond in the case of a target 1076 that is displayed closer to the fixation mark 1061 than the ends of the lines that separate the sectors. It is helpful not to place visible features of the response zones, such as circles or lines of FIGS. 10D and 10E, too close to the target location, because doing so will to reduce the visibility of the target through forward masking (if the features are presented before the target) or simultaneous masking or backward masking (if the features are presented soon after the target).

Figure 11A:
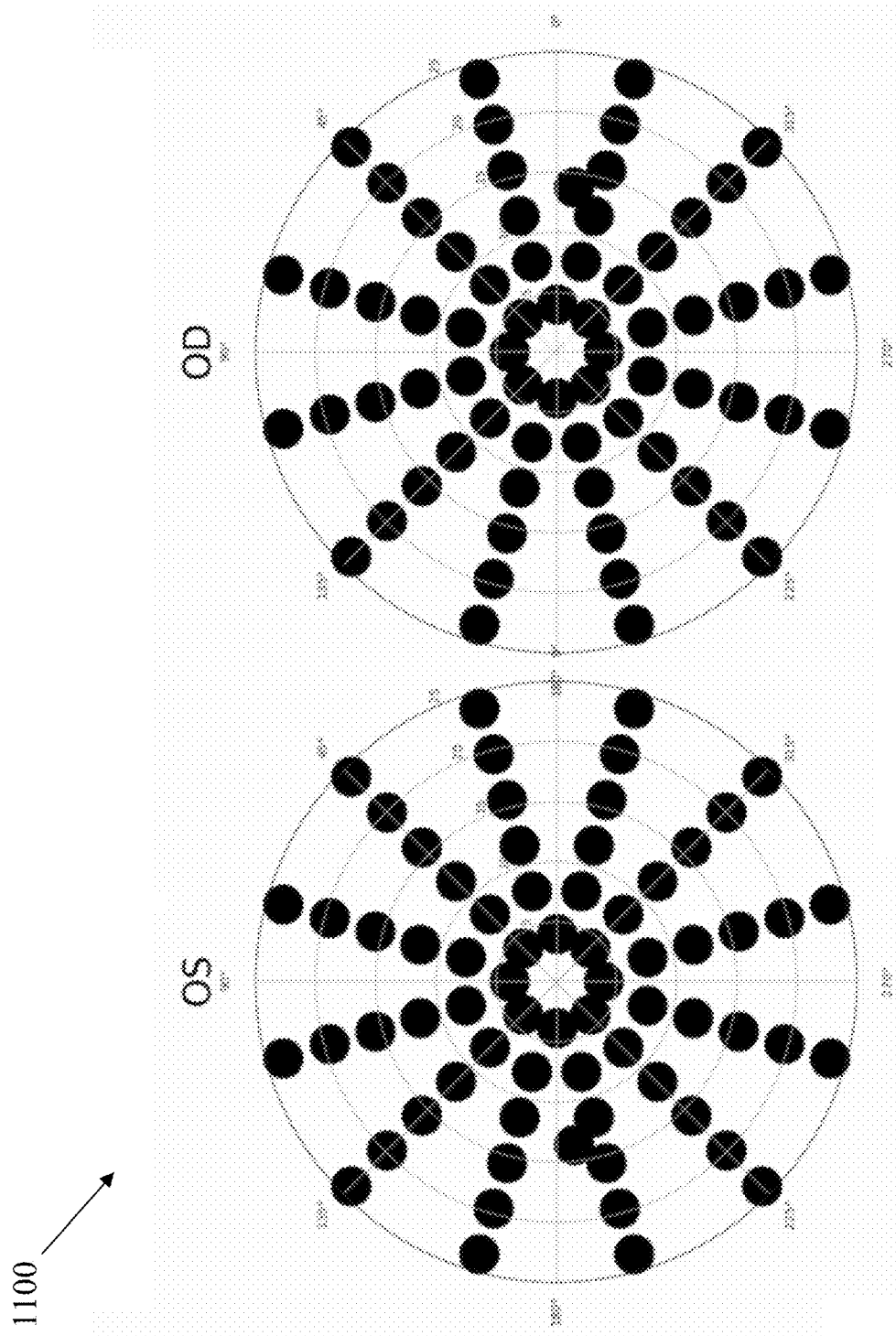
FIG. 11A is a schematic illustration of one example of a test layout in accordance with some embodiments.

FIG. 11A illustrates an example 1100 of a test layout including 69 locations per each eye (the left eye ("OS") and the right eye ("OD")) that can be tested in one embodiment. In this example, each test target is in the form of a dark (e.g., black) spot displayed on a white background. Each test target can be a 1° object, displayed for 300 ms, and a certain number of times per location. The test targets can be presented randomly, such that all 69 locations in the patient's visual field are ultimately tested.

Figure 11B:
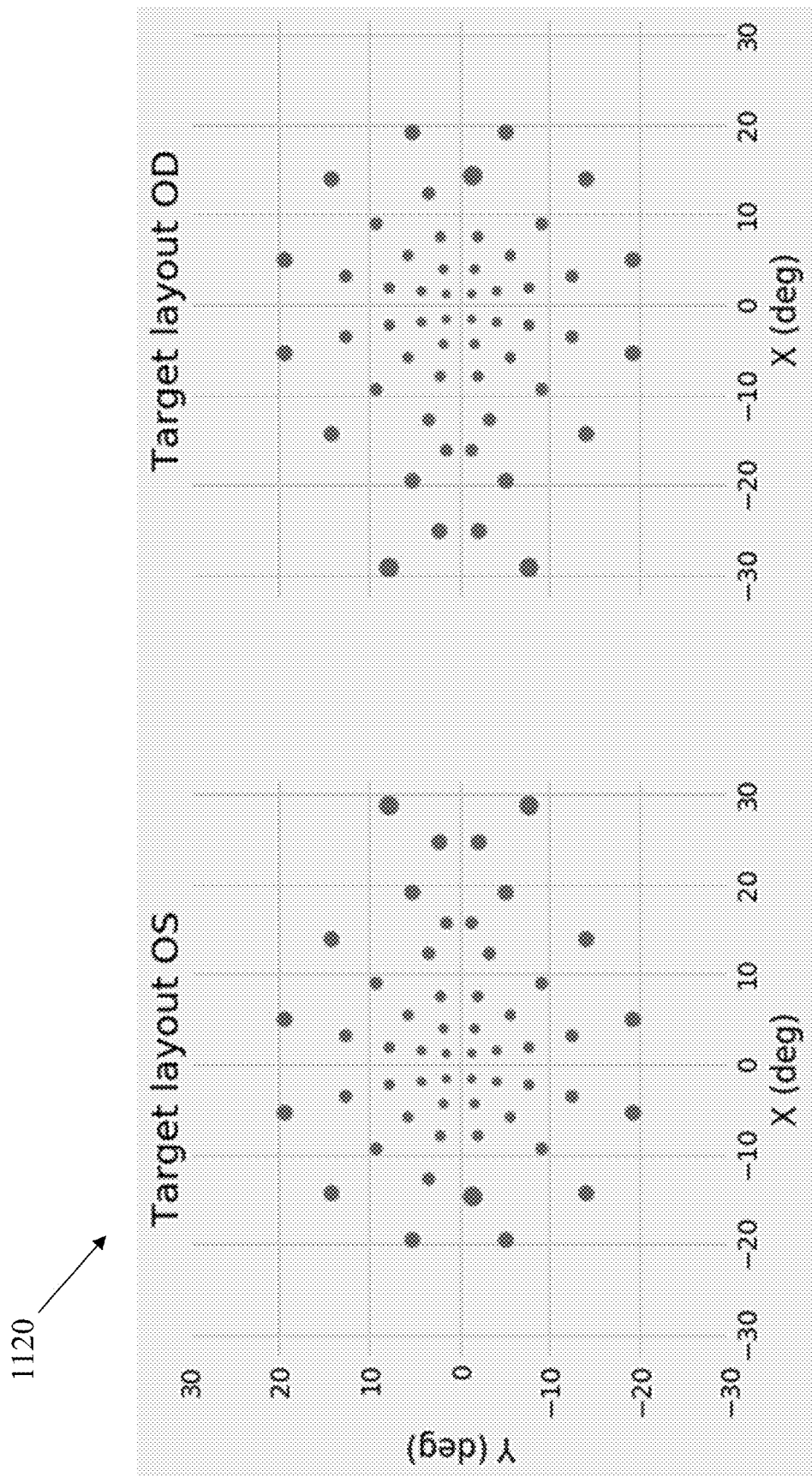
FIG. 11B is a schematic illustration of one example of a test layout, in the shape of a ladybug, in accordance with some embodiments.

FIG. 11B illustrates an example 1120 of a test layout including 54 locations per each eye (the left eye ("OS") and the right eye ("OD")) that can be tested in one embodiment. This example is a "Ladybug" design, so-called because its appearance resembles a ladybug. In this example, each stimulus (represented by a blue disk) is in the form of a gray spot displayed on a light gray background. In this embodiment of the test, sampling is denser in central vision than in peripheral vision, which is appropriate because ganglion cells are denser in central vision than in peripheral vision. In one embodiment not shown, the spatial layout of the targets reflects ganglion cell density precisely, so that each target location has approximately the same number of ganglion cells nearby. In one embodiment not shown, the sizes and shapes of the targets are designed to tile the visual field, so that the receptive fields of all ganglion cells contribute to the visual system's response to at least one target.

The stimulus layout shown in FIG. 11B is intended for use in a screening test for glaucoma. It therefore includes denser sampling at locations in the nasal visual field that may be needed to detect the "nasal step" pattern of sensitivity loss that are common in glaucoma.

Figure 11C:
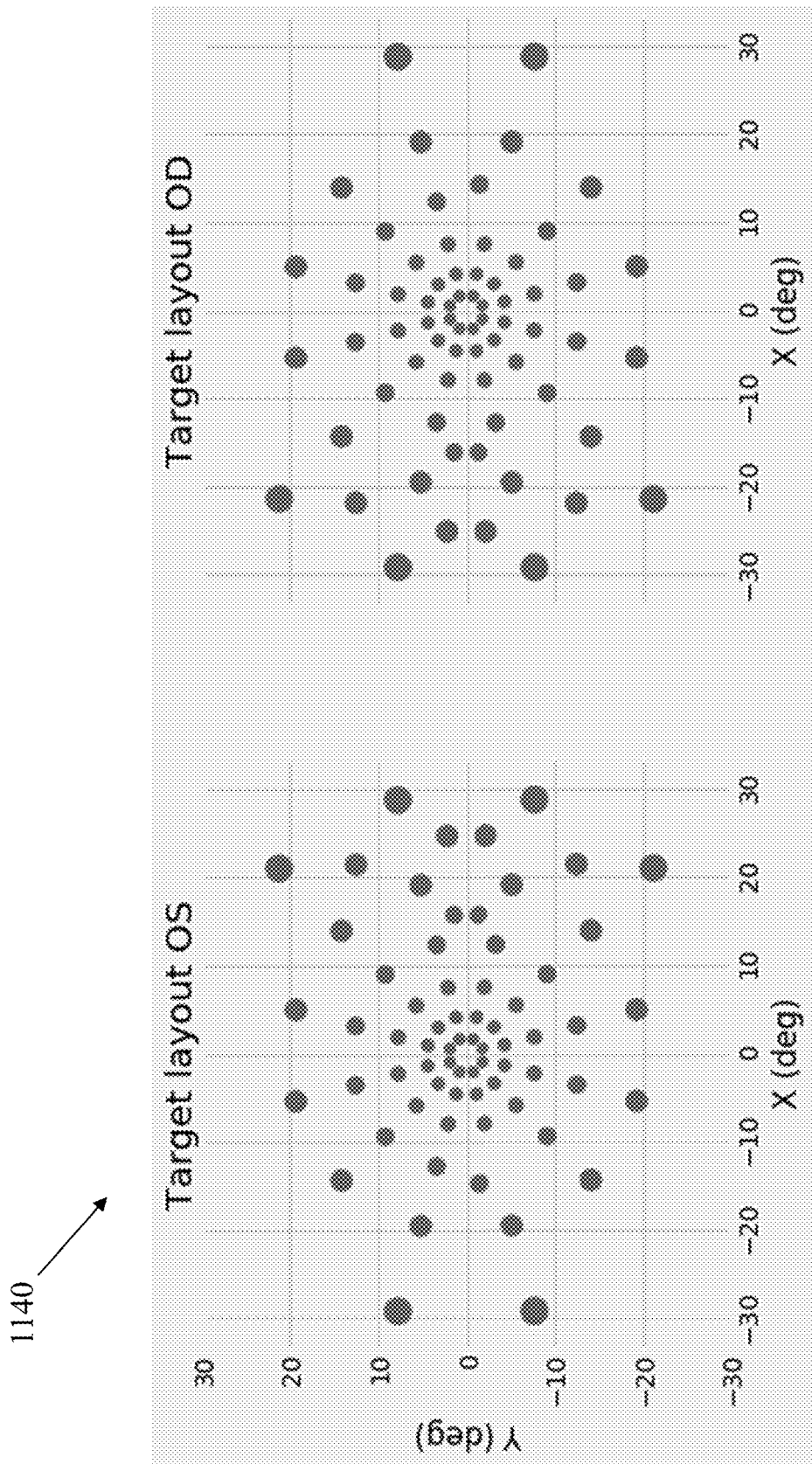
FIG. 11C is a schematic illustration of one example of a test layout, in the shape of a tortoise, in accordance with some embodiments.

FIG. 11C illustrates an example of a test layout 1140 including 62 locations per each eye (the left eye ("OS") and the right eye ("OD")) that can be tested in one embodiment. This example is a "Tortoise" design, so-called because its appearance resembles a tortoise. The stimulus layout shown in FIG. 11B is intended for use in a monitoring test for glaucoma. It is similar to the screening test layout of FIG. 11A, but it because it has more stimulus locations, testing will take longer. The benefit to a patient with glaucoma is that that a larger fraction of the patient's visual field is tested, which is beneficial for monitoring the progression of vision loss over time.

An additional advantage of testing more densely in central vision is that the target locations reflect equal spacing after cortical magnification for the type of target used is taken into account, so that stimuli sample the functionally relevant map of the visual field more uniformly than would be the case for samples with uniform spacing on the retina.

Cortical magnification is greater for pattern identification tasks and pattern discrimination tasks than it is for detection tasks, meaning that the ability to identify or discriminate letters or other objects from one another falls off with eccentricity more quickly than the ability to detect a transient change in luminance. Accordingly, stimuli that require identification or discrimination will be spaced more densely in central vision and more sparsely in peripheral vision than stimuli that require detection of luminance change, and will also grow in size more quickly as eccentricity increases.

In FIGS. 11A, 11B, and 11C, each stimulus can be an object, the size of which increases with the stimulus' eccentricity, so that the threshold luminance for stimulus detection is approximately constant for all stimuli in the display for a normally sighted observer. For example, the sizes of the stimuli can be chosen so that on average, a person of the same age as the patient will correctly report the location of the target on 95% of presentations. For example, all stimuli in the display could be presented at a luminance equal to 90% of the background luminance, and any missed stimuli could be presented again at 0% of the background luminance, to create a "3-zone" test in which the stimulus was either seen, missed and then seen, or missed and then missed again.

The stimuli in a layout such as FIG. 11A, 11B, or 11C can be presented at one eccentricity at a time, so that the patient can expect the target to occur within this limited region of the display. For example, the first targets tested could be the central-most targets, followed by the next-most central ring of targets, and so on. The patient is therefore able to allocate their visual attention to a specific annulus of the display, which may improve detection thresholds as compared to when visual attention must be allocated diffusely across the entire display. In addition, patients may experience the test as easier to take if they can simply maintain attention on one annular region of the display at a time, as compared to attending to all of the display for the full duration of the test.

Figure 12:
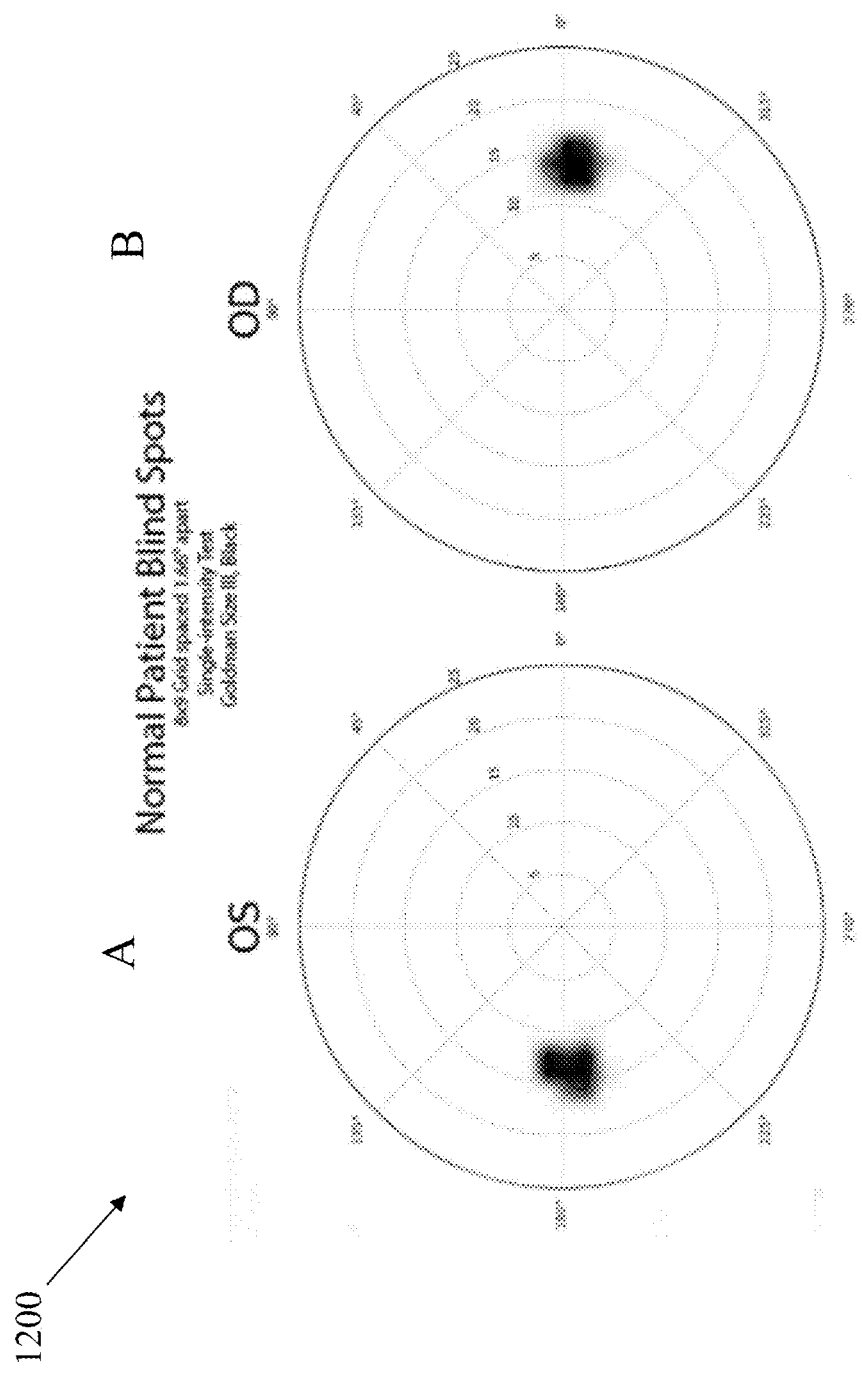
FIG. 12 shows an example of a result of assessment of a patient's visual field using a head-pointer approach, in accordance with some embodiments.

FIG. 12 shows an example of a result 1200 of using the described system using a head-pointer approach, illustrating that this method is effective. An example of a test involves locating blind spots in a patient with normal vision. The results are shown in FIG. 4, where section A ("OS," shown on the left) indicates the location and size of the blind spot of the patient's left eye, and section B ("OD," shown on the right) indicates the location and size of the blind spot of the patient's right eye. As shown, the system has correctly determined the location and size of the blind spots.

Figure 13:
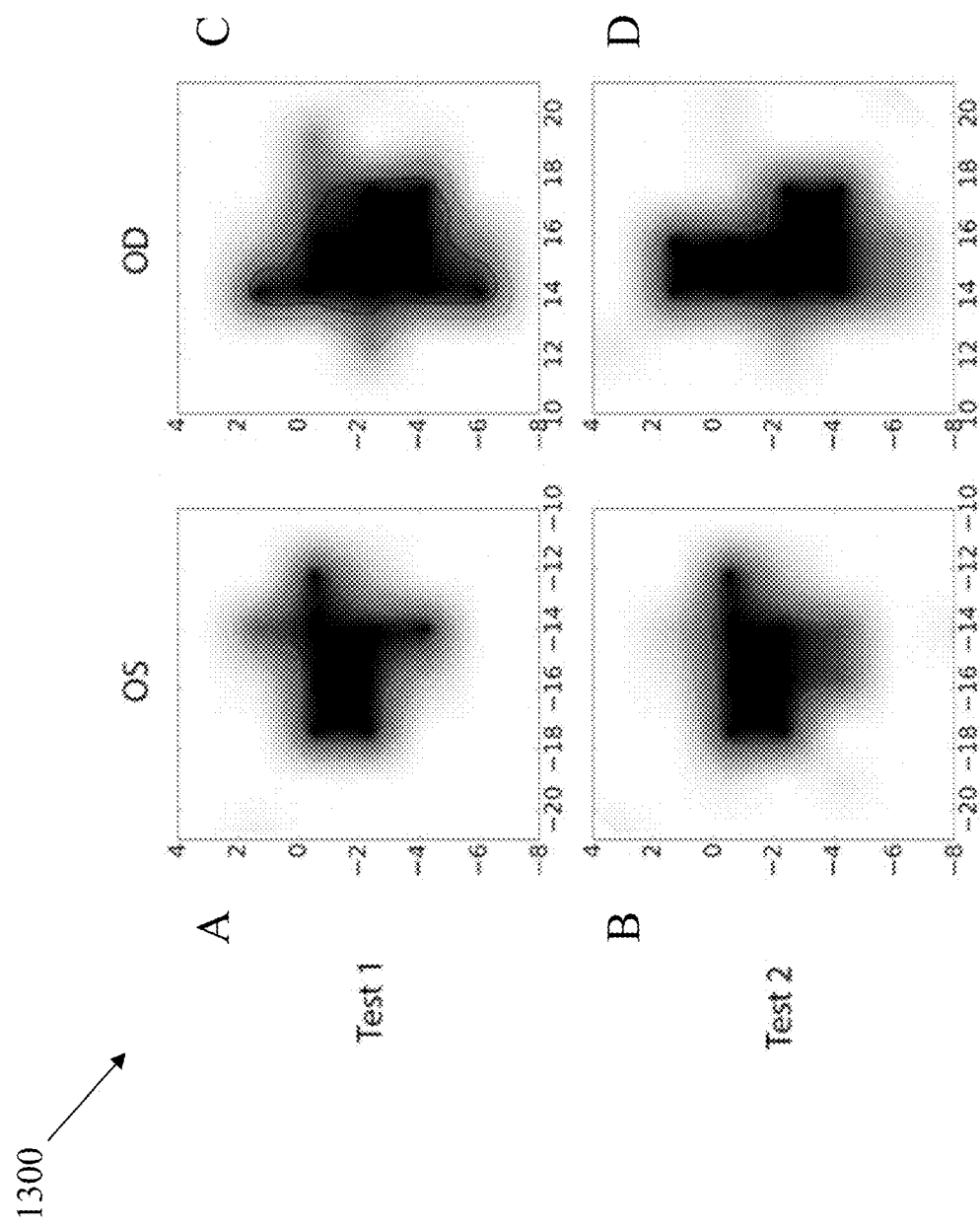
FIG. 13 shows an example of results from two tests using a head-pointer approach, in accordance with some embodiments.

FIG. 13 shows another example of results 1300 from two tests using a head-pointer approach. The "OS" sections A and B, and the "OD" sections C and D shows the results of testing user's left and right eyes, respectively. In this case, sampling was dense in the blind spot, with targets in an 8×9 grid centered on and extending beyond the expected location of the blind spots. Each location was sampled 5 times. The map interpolates fraction of targets detected in the test, from 0/5 (black) to 5/5 (white). The top (A and C) and bottom (B and D) sections show the first and second replications of the test, respectively. FIG. 13 illustrates that the test can give reliable (test-retest) results in patients with normal vision.

Figure 14:
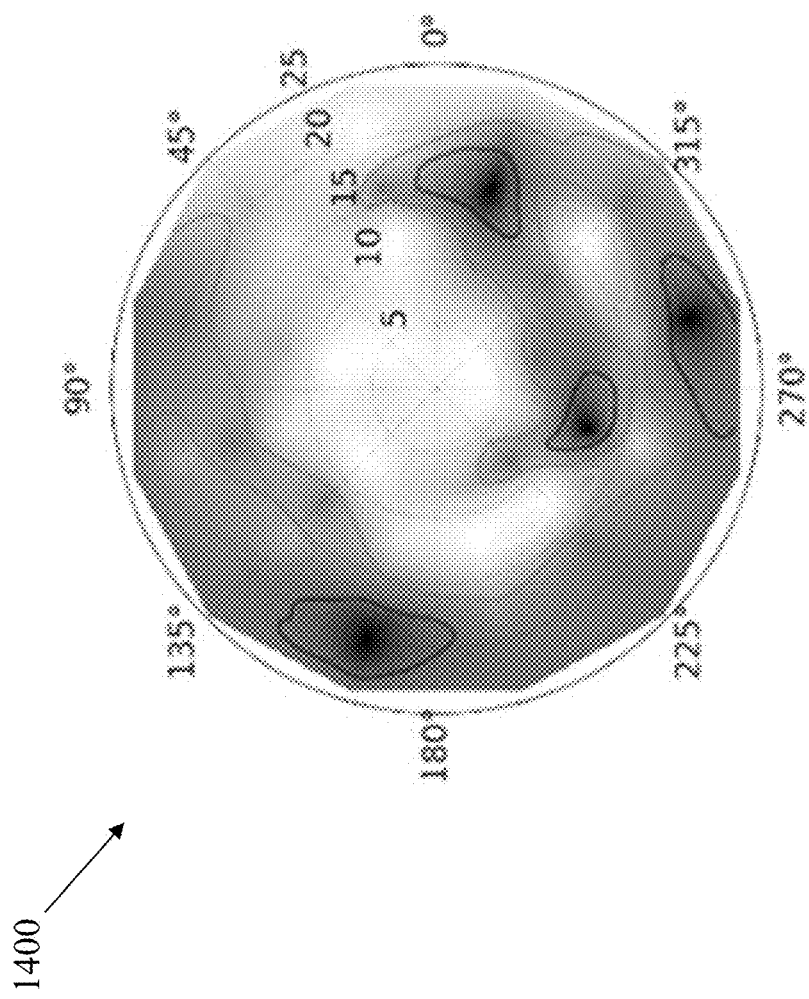
FIG. 14 is an example of a result of assessment of a visual field of a patient with primary open-angle glaucoma using a head-pointer approach, in accordance with some embodiments.
Figure 15:
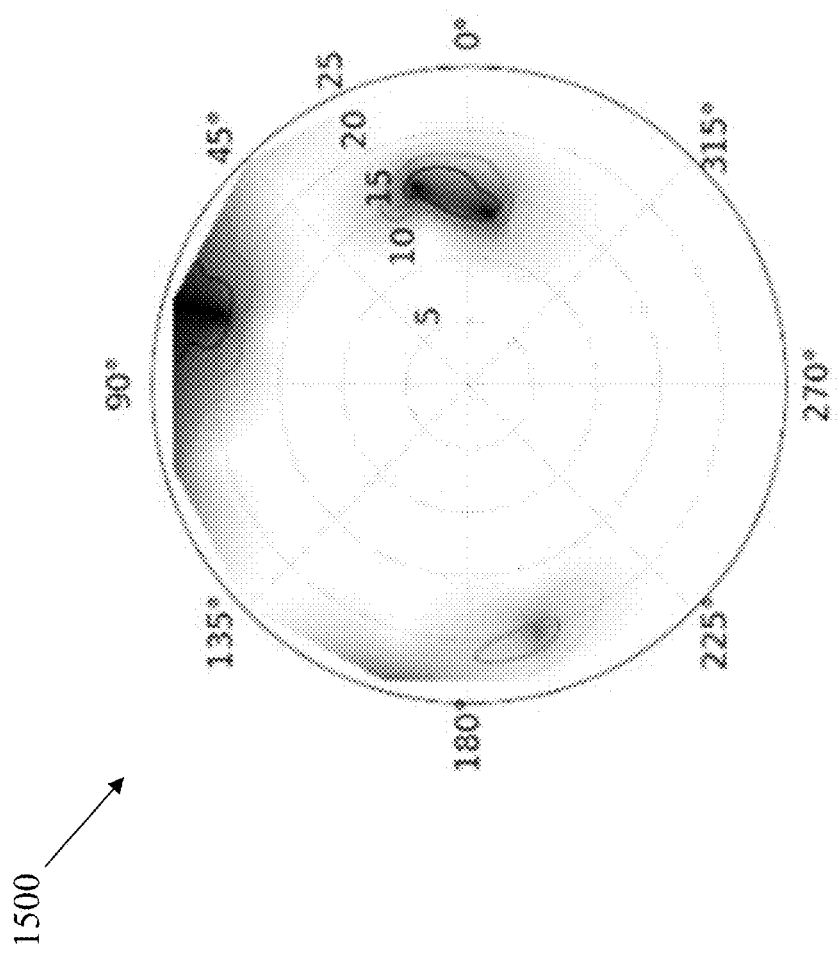
FIG. 15 is an example of a result of assessment of a visual field of another patient with primary open-angle glaucoma using a head-pointer approach, in accordance with some embodiments.

FIGS. 14 and 15 show examples of a result of using the described system for the head-pointer test in two patients with primary open-angle glaucoma. FIG. 14 shows results plotted 1400 based on data acquired for the right eye of a 50-year-old man with severe primary open angle glaucoma (POAG) OU. The result shows a deviation in test results from age-matched normal results. FIG. 15 shows results plotted 1500 based on data acquired for the right eye of n 80-year-old man with mild POAG OU, for whom OCT (nerve) showed inferotemporal borderline thinning OD, and who had some cataract. The result shows an estimated sensitivity across the visual field. The normal blind spot in both patients is shown in FIGS. 14 and 15. In FIG. 15, a superior defect is shown, in addition to slight constriction of the nasal field and loss of sensitivity superior to the normal blind spot.

Figure 16:
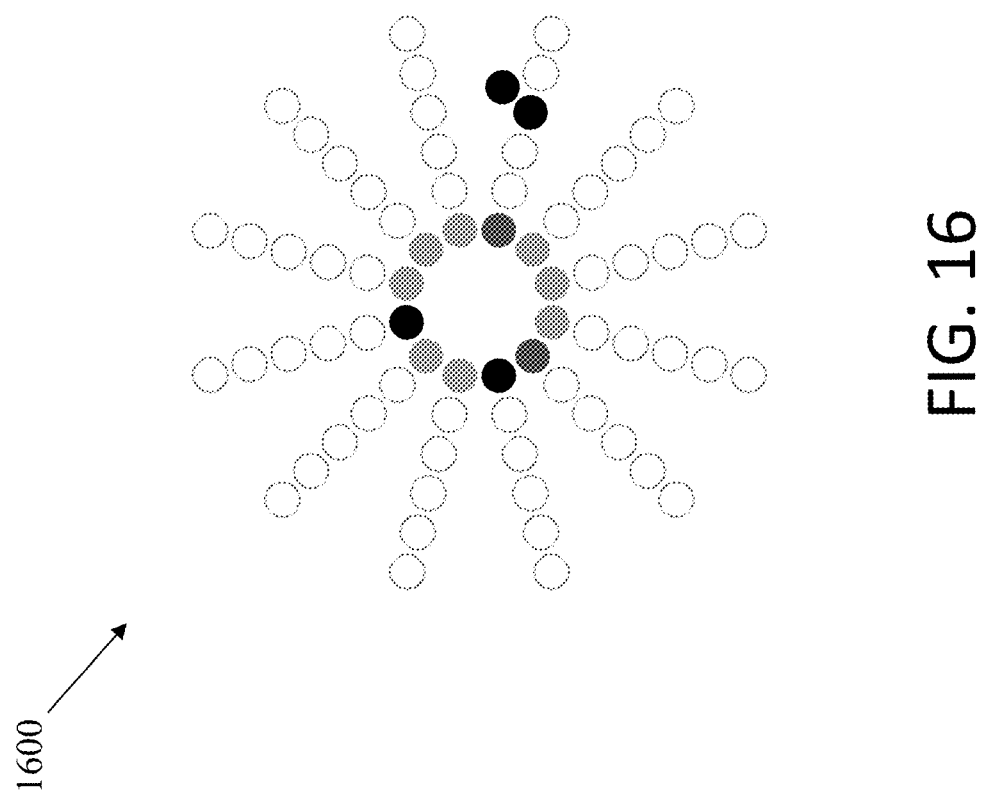
FIG. 16 shows a graph for representing the results of a visual field test, in which raw data are show in a schematic layout that corresponds to the spatial layout of the test targets.

FIG. 16 shows a graph 1600 for representing the results of a visual field test. In this format, raw data are show in a schematic layout 1600 that corresponds to the spatial layout of the stimuli, in which test target spacing is not proportional to the test target spacing in the test. Instead, eccentricity and target size are transformed to be regular, to facilitate comparison of results across test locations. In this example, the data show central targets that were missed some of the time (light gray or dark gray color) or all of the time (black color), and peripheral targets were seen all of the time (white color outlined by gray circle) except near the normal blind spot. The normal blind spot was not seen (black color).

Figure 17:
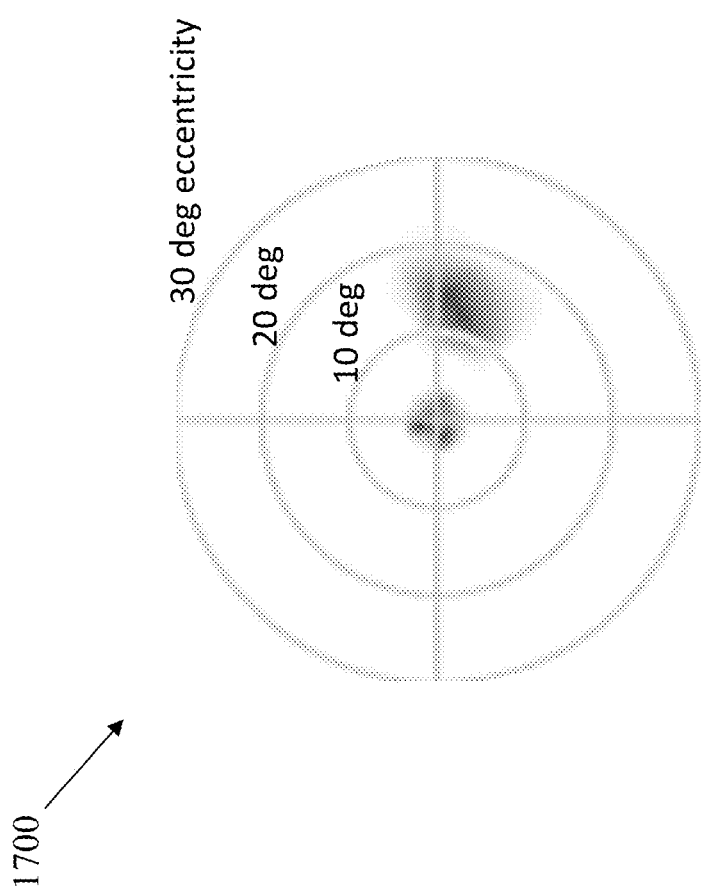
FIG. 17 shows a graph for representing the results of a visual field test, in which a colormap is created by interpolation and extrapolation from sample points that are spaced proportionally to the test target spacing in the test.

FIG. 17 shows a graph 1700 for representing the results of a visual field test. Loss of sensitivity, relative to normal, progresses from white (normal) to gray (some loss) to black (severe loss). Unlike the schematic layout of FIG. 16, in FIG. 17 the colormap is not systematically distorted. The colormap was created by interpolation and extrapolation from sample points that are spaced proportionally to the test target spacing in the test.

Figure 18:
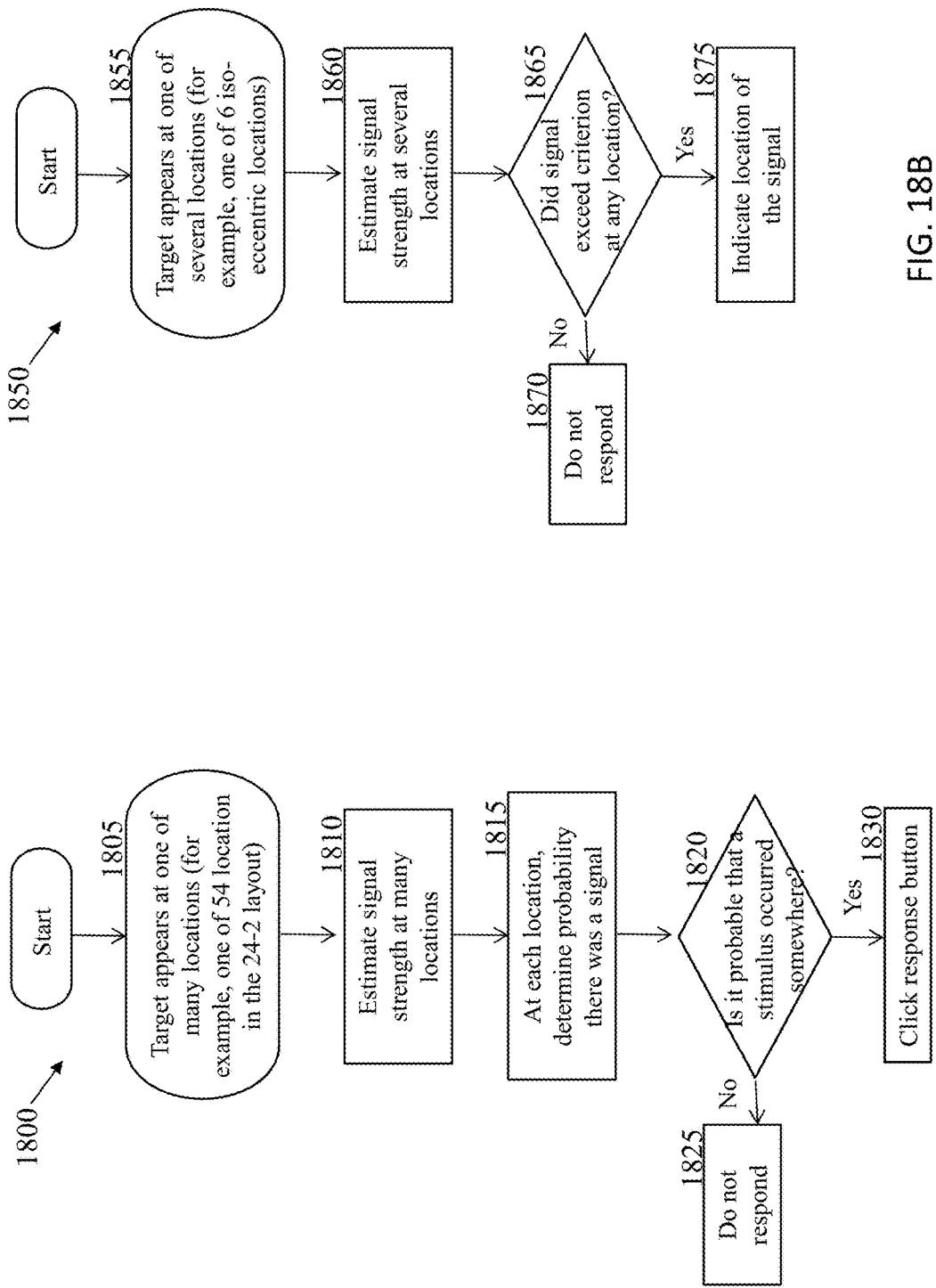
FIG. 18A shows a model of the patient's cognitive process for traditional perimetry.
FIG. 18B shows a model of the patient's cognitive process for the methods of perimetry according to various embodiments of the disclosed technology.

FIG. 18A shows a model 1800 of the patient's cognitive process for traditional perimetry. At 1805, a test target appears at one of many (for example, 54) locations. At 1810, the patient estimates signal strength of the test target at many locations. At 1815, the patient determines the probability that there was a signal at each location. At 1820, the patient considers whether it's probable that a stimulus (test target) flashed. If not, at 1825 the patient does not respond. If so, at 1830 the patient clicks a response button.

FIG. 18B shows a model 1850 of the patient's cognitive process for the methods of perimetry according to various embodiments of the disclosed technology. At 1855, a test target appears at one of several (for example, 6) locations. At 1860, the patient estimates signal strength at several locations. At 1865, the patient considers whether the signal strength of the test target exceed criterion at any location. If not, at 1870 the patient does not respond. If so, at 1875 the patient indicates the location of the signal.

Therefore, in traditional perimetry of FIG. 18A, the patient makes a single "go/no-go" decision, so a decision not to respond is made during the final stage of cognitive processing on that trial. In the methods according to the disclosed technology of FIG. 18B, the patient reports the location of the target on "go" responses. For example, the patient might choose one of six possible locations at which the stimulus could have occurred on that trial. This change in task requirement is subtle but it can have a profound effect on the comfort of the patient, for two reasons. (1) The patient can be instructed, "if you see the stimulus, report where it was." In fact, people with intact neurology do not detect an object without also perceiving the object's location. Given that the location of the stimulus is always encoded, there is no additional cost to the patient in reporting the stimulus location. In particular, consider a situation in which the patient is 75% sure that a target appeared at location A and 75% sure that a target appeared at location B. This situation could happen if the patient has low sensitivity at locations A and B, or if the stimulus has low contrast. In the traditional test, it is likely that the stimulus occurred, even though the patient is unsure where it occurred. The optimal choice is to click the response button. In the new test, the optimal choice is to not respond, because the stimulus did not exceed criterion at either location separately, and either location has a 50% chance of being incorrect. It may be difficult and unnatural to combine probabilities across locations in the manner needed for optimal threshold-level performance in the traditional no/no-go task design. (2) The patient can use a higher criterion for responding, which allows the use of stronger (for example, higher contrast) stimuli during the test. As a consequence, the patient is likely to feel more comfortable with his or her decision to respond or not: it is less distressing to choose "not seen" when the optimal decision rule is simply that no location exceeded criterion. Another way to say this is that, with the new method, the patient feels comfortable in not responding if he or she has high uncertainty as to where the target appeared.

In some embodiments, in addition to head tracking, tracking of patient's eyes is also performed, which can improve performance of tests using the described system.

Thus, the head tracking is combined with the eye tracking, which provides improved user experience. While being comfortable to patients, the system is also accurate for mapping visual fields.

In some embodiments, a test performed by a patient can be in the form of a game. In-game VR-based diagnostic vision testing can be done at home or other setting outside a medical facility. A user interface presented to a patient (on a user's at-home computing device or on an in-clinic computing device) can be configured to receive user login information and further information associated with user's performing in-game VR tests in-clinic or at-home. In some cases, the testing can be accompanied by simultaneous real-time monitoring of test results and patient compliance by medical personnel. Thus, patients' compliance can be monitored remotely, while real-time, at-home diagnostic tests are administered in a patient's home (or other location other than a medical facility). Data acquired by the system (e.g., via the computing device) as the patient performs tests in a home environment can be supplemented with data acquired in a medical facility, under supervision of a trained medical professional.

Furthermore, as discussed above, in some embodiments, foveation (angling the eyes to focus on an object) can be used, such that a patient is encouraged to make eye movements toward peripheral targets when they appear. Additionally, as mentioned above, a patient can be instructed to select from among a number of alternative eye-movement choices. Thus, the patient can be allowed to specify a direction towards the target using a natural eye movement. For example, patient's eyes can be tracked during the patient's performing a test and/or activity.

In some embodiments, during perimetry, a plurality of targets can be displayed on a display of a head-mountable device with an interval of 2 seconds. Such an interval can allow the patient to re-fixate on a central target (which can be unchanging), redeploy attention broadly, and check that fixation is accurate. On the other hand, humans can make sequential fixations at 2 Hz or faster, resulting in a factor of 4 or better reduction in testing time. Accordingly, the described techniques utilize, for perimetry, tracking of eye movements towards visual targets, where the visual targets become fixation targets for a next trial. Allowing a patient to foveate the target can provide testing with improved speed and generally improved patient's experience.

In some embodiments, both head-pointing and eye tracking are used to create a sensitivity map. Eye tracking can be used to determine the patient's response (whether the patient saw the target) and to determine patient's eye position at the moment of the next target presentation. The eye position and head-pointer information can be combined to build a metric for the direction of the patient's orienting response.

The described systems and techniques use various computational algorithms. For example, in some embodiments, a "filling in" mesh algorithm can be used to dynamically cause sampling to be denser in areas of detected scotomas. Common forms of vision loss do not affect all parts of the retina equally, but have stereotypical geography. Thus, efficient screening may require deviating from isotropic sampling to make use of prior probabilities. Similarly, to monitor progression of glaucoma, with its characteristic arcuate geography, an efficient algorithm would place each test target at a location, and contrast, to maximize information about the dB sensitivity map as a whole. In some embodiments, to monitor progression of glaucoma, Bayes-optimal algorithms are used that are adapted from models of humans' fixation behavior when a goal is to search for a hidden visual target. Test locations can be re-allocated according to history earlier in the session and/or previous sessions. A slope of a psychometric function (whether it is shallow enough) relative to an abruptness of change in sensitivity across space can be determined. Furthermore, a purpose of each trial can be an improvement in the overall map of sensitivity.

Furthermore, in some embodiments, instructions to a patient can be provided in the form of a game, which can be done in conjunction with auditory feedback during training and testing. For example, the auditory feedback can be intended to motivate the patient to perform the required procedures in a proper manner, and to "reward" the patient for proper performance. In addition, the system can be configured to process images acquired from cameras (which can be built-in into the head-mountable device) to detect fogging, proper centration, and other features that can affect patient's performance. Moreover, in some embodiments, no audio instructions are provided to the patient, and any instructions and/or prompts are in the visual form. For example, in at least some embodiments, instructions to a patient can be provided in the form of a video illustrating an example of a proper performance of a test. In some embodiments, the training can involve providing a "reward" to the patient in the form of a pleasing auditory signal (or visual signal for a deaf person).

As mentioned above, various information related to visual testing (e.g., instructions, patient information, results in a graphical or any other format, etc.) can be displayed on a display of one or more computing devices, which can be a mobile device. For example, on a user interface that can be presented to a clinician a login page of a patient portal used at initial clinic visit to create a secure patient account can be displayed. As another example, a user interface can be rendered by an online platform with clinical research features such as, e.g., masking, remote randomization, enrollment, privacy, auditing, remote monitoring of results and compliance, and other features used to remotely monitor status of patient. The data can be displayed based on permissions—e.g., different permissions can be set (in a changeable manner) for each person. A user interface can display a visual representation of diagnostic results and test-taking compliance data for a particular patient, where the data can be updated in real-time.

Figure 19:
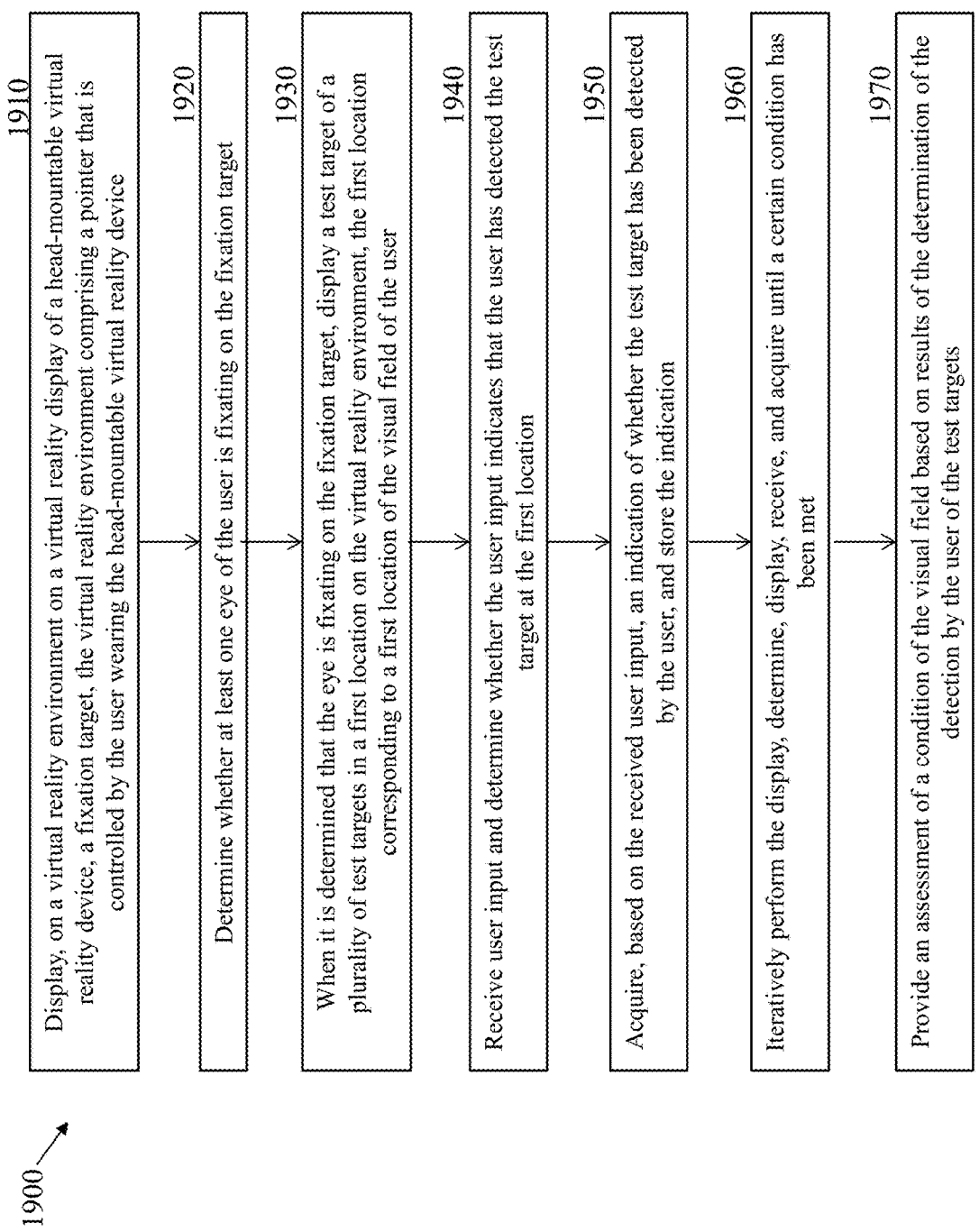
FIG. 19 is a flowchart of a process for assessing a visual field of a user according to various embodiments of the disclosed technology.

FIG. 19 is a flowchart of a process 1900 for assessing a visual field of a user according to various embodiments of the disclosed technology. Referring to FIGS. 2A, 2B and 19, the process 1900 may be performed by the computing device 202 or the user computing device 230.

At 1910, the computing device 202 displays, on a virtual reality environment on a virtual reality display 210 of a head-mountable virtual reality device 208, a fixation target, the virtual reality environment comprising a pointer that is controlled by the user wearing the head-mountable virtual reality device 208.

At 1920, the computing device 202 determines whether at least one eye of the user is fixating on the fixation target.

At 1930, when the computing device 202 determines that the eye is fixating on the fixation target, computing device 202 displays a test target in a first location on the virtual reality environment. The first location corresponds to a first location of the visual field of the user.

At 1940, the computing device 202 receives user input and determines whether the user input indicates that the user has detected the test target location.

At 1950, the computing device 202 acquires, based on the received user input, an indication of whether the test target has been detected by the user, and storing the indication.

At 1960, the computing device 202 iteratively performs the displaying, determining, displaying, receiving, and acquiring until a certain condition has been met.

At 1970, the computing device 202 provides an assessment of a condition of the visual field based on results of the determination of the detection by the user of the test targets during the iterative performance of the displaying, determining, displaying, receiving, and acquiring steps.

In various embodiments, the user input indicating that the user has detected the test target at the first location includes determining whether the user input indicates that the pointer is moving towards the first location. In various embodiments, the user input indicating that the user has detected the test target at the first location includes determining whether the user input indicates that a head of the user is moving towards the first location. In various embodiments, the user input indicating that the user has detected the test target at the first location includes determining whether the user input comprises a pupil response. In various embodiments, the user input indicating that the user has detected the test target at the first location includes determining whether the user input comprises a button press.

In various embodiments, the process 1900 includes determining a position of the eye and/or pupil when it is determined that the eye is fixating on the fixation target.

In various embodiments, the iterative performance of the displaying, determining, displaying, receiving, and acquiring steps continues until all test targets of the plurality of test targets have been displayed. In various embodiments, the iterative performance of the displaying, determining, displaying, receiving, and acquiring steps continues until a predetermined period of time has passed. In various embodiments, the iterative performance of the displaying, determining, displaying, receiving, and acquiring steps continues until a predetermined level of statistical confidence in an assessment has been reached.

In various embodiments, the test target is displayed at least partially simultaneously with displaying the fixation target when it is determined that the eye is fixating on the fixation target. In various embodiments, determining whether the eye is fixating on the fixation target includes determining whether the patient's fovea is fixated on the fixation target.

In various embodiments the process 1900 includes comparing a stability of the patient's binocular fixation to a stability of the patient's monocular fixation in each eye to determine whether to display the fixation target one eye at a time or to both eyes simultaneously.

In various embodiments, the user input includes an indication of movement of the pointer in the virtual reality environment.

In various embodiments, acquiring the indication that the test target has been detected by the user includes determining that the pointer is positioned within a predetermined distance from the first location. In various embodiments, acquiring the indication that the test target has been detected by the user includes acquiring an indication that the location of the test stimulus has been detected by the user. In various embodiments, acquiring the indication that the test target has been detected by the user includes determining a movement of one or both eyes, a head, facial muscles, one or both pupils, and or body of the user.

In various embodiments, the iterative performance of the displaying, determining, displaying, receiving, and acquiring steps includes displaying, in a second location on the virtual reality environment corresponding to a second location of the visual field of the user that is different from the first location of the visual field of the user, a subsequent test target of the plurality of test targets.

In various embodiments, the iterative performance of the displaying, determining, displaying, receiving, and acquiring steps includes displaying, on the virtual reality environment, a subsequent fixation target; determining whether the eye is fixating on the subsequent fixation target; when it is determined that the eye is fixating on the subsequent fixation target, displaying, in a second location on the virtual reality environment corresponding to a second location of the visual field of the user that is different from the first location of the visual field of the user, a subsequent test target of the plurality of test targets; receiving user input comprising an indication that the user has detected the subsequent test target at the second location; and acquiring, based on the received user input, a second indication of whether the subsequent test target has been detected by the user, and storing the second indication. In various embodiments, the subsequent test target has at least one property that is different from at least one property of the test target that was displayed in the first location.

In various embodiments, determining whether the eye is fixating on the fixation target includes determining whether the pointer has moved such that the pointer at least partially overlaps with the fixation target. In various embodiments, the fixation target includes a representation of at least one movable object. In various embodiments, the fixation target is displayed in the vicinity of the first location.

In various embodiments, receiving user input further includes acquiring eye tracking information using a sensor monitoring at least one of the eyes of the user wearing the head-mountable virtual reality device.

In various embodiments, the head-mountable virtual reality device includes glasses.

In various embodiments, the user input is further received from at least one input device selected from the group consisting of a mouse, a joystick, a keyboard, a hand-held gesture and motion tracking device, a gesture and motion device that is not hand-held, a microphone, at least one camera, an omnidirectional treadmill, a head tracking device, a body tracking device, a facial muscle sensor, and a game pad.

In various embodiments, the system 250 includes a mobile computing device including the computing hardware. In various embodiments, the pointer includes a head pointer and/or a hand pointer.

In various embodiments, physical and other characteristics of the fixation target or test targets and the rules for whether and how they are displayed are described within a spread sheet or data file that can be altered by the person conducting the test. In various embodiments, physical and other characteristics of the fixation target or test targets and the rules for whether and how they are displayed are configured on a separate computing device and received on the device that administers the test through a network connection.

In various embodiments, the results and data collected during the testing are sent to a separate computing device. In various embodiments, one or more properties of the test stimulus are at least in part determined by prior test results from the current patient and/or other patients.

In various embodiments, acquiring the indication that the test stimulus has been detected by the user includes determining that the pointer is positioned within one of at least two sectors surrounding the location of the fixation target.

In various embodiments the assessment of a condition of the visual field includes information on the identification, status, and/or progression of glaucoma, multiple sclerosis, macular degeneration, diabetic retinopathy, neurological function, retinitis pigmentosa, color vision, binocular vision including suppression scotomas, and/or vascular disease.

In various embodiments, a method for assessment of a visual field of a user includes displaying, on a user interface rendered on a display associated with a computing device, a fixation target. The user interface includes a pointer that is controlled by the user viewing the user interface. The method further includes determining whether at least one eye of the user is fixating on the fixation target. When it is determined that the eye is fixating on the fixation target, the method further includes displaying a test target of a plurality of test targets in a first location on the user interface, the first location corresponding to a first location of the visual field of the user. The method further includes receiving user input comprising an indication that the user has detected the test target at the first location. The method further includes acquiring, based on the received user input, an indication of whether the test target has been detected by the user, and storing the indication. The method further includes iteratively performing the displaying, determining, displaying, receiving, and acquiring until a certain condition has been met. The method further includes providing an assessment of a condition of the visual field based on results of the determination of the detection by the user of the test targets during the iterative performance of the displaying, determining, displaying, receiving, and acquiring steps. In various embodiments, the computing device comprises a smartphone. In various embodiments, the computing hardware is included in the computing device. In various embodiments, the display is part of the computing device. In various embodiments the computing device includes a smart television. In various embodiments, the computing device includes a personal computer. In various embodiments, the user interface includes a virtual reality environment on a virtual reality display of a head-mountable virtual reality device. In various embodiments, the user input is further received from at least one input device selected from the group consisting of a mouse, a joystick, a keyboard, a gesture and motion tracking device, a microphone, at least one camera, an omnidirectional treadmill, and a game pad.

It should be appreciated that the various embodiments described herein can have various modifications. For example, images presented on a display viewed by a patient using a visual test assessment can be presented to one or both of the patient's left and right eyes. In some embodiments, one of the eyes can be tested without the patient being aware that this particular eye is being tested.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable computer hardware, which can be special or general purpose processor, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A system for assessment of a visual field of a user, the system comprising: computing hardware configured to perform operations comprising:
    (a). displaying, on a virtual reality environment on a virtual reality display of a head-mountable virtual reality device, a first fixation target, the virtual reality environment comprising a pointer that is controlled by a user wearing the head-mountable virtual reality device, the first fixation target being one of a plurality of fixation targets;
    (b). determining whether a fixation task associated with the first fixation target has been completed by the user, wherein the fixation task is completed when the pointer overlaps at least a portion of the first fixation target, and wherein the first fixation target is configured such that it requires foveal vision of the user to complete the fixation task;
    (c). in response to that the fixation task is completed, displaying, on the virtual reality display, a first test target at a first location, wherein the first test target is configured such that it requires the foveal vision of the user to complete a first test task, the first test target being one of a plurality of test targets, wherein a set of display properties of the first test target is adjusted based in part on the user's response to the fixation task;
    (d). determining whether the user has detected the first test target at the first location based on an analysis of user input; and
    (e). collecting, based on the user input, data related to the determining of whether the user has detected the first test target at the first location;
    automatically iteratively performing (a)-(e) for each of a subset of the plurality of fixation targets and corresponding ones of the plurality of test targets until a certain termination condition is met, and
    providing information related to a result of the visual field assessment of the user based at least on the collected data from the iterative performance of (a)-(e).

2. The system of claim 1, wherein the analysis of the user input comprises determining whether the user input indicates that the pointer is moving towards the first location.

3. The system of claim 1, wherein the analysis of the user input comprises determining whether the user input indicates that a head of the user is moving towards the first location.

4. The system of claim 1, the operations further comprise:
    displaying, at a second location on the virtual reality environment that is different from the first location, a second test target of the plurality of test targets.

5. The system of claim 1, wherein the first fixation target is displayed in vicinity of the first location.

6. The system of claim 1, the operations further comprise:
    based at least on determining that the fixation task associated with the first fixation target is not completed, modifying one or more properties associated with the first fixation target until the fixation task is completed.

7. The system of claim 1, wherein the first fixation target and the first test target are associated with a plurality of display properties to ensure that it requires foveal vision of the user to complete the fixation task and the first test task, wherein the plurality of display properties comprise size, luminance, contrast, and moving speed.

8. A method for assessment of a visual field of a user, the method comprising:
    (a). displaying, on a virtual reality environment on a virtual reality display of a head-mountable virtual reality device, a first fixation target, the virtual reality environment comprising a pointer that is controlled by a user wearing the head-mountable virtual reality device, the first fixation target being one of a plurality of fixation targets;
    (b). determining whether a fixation task associated with the first fixation target has been completed by the user, wherein the fixation task is completed when the pointer overlaps at least a portion of the first fixation target, and wherein the first fixation target is configured such that it requires foveal vision of the user to complete the fixation task;
    (c). in response to that the fixation task is completed, displaying, on the virtual reality display, a first test target at a first location, wherein the first test target is configured such that it requires the foveal vision of the user to complete a first test task, the first test target being one of a plurality of test targets, wherein a set of display properties of the first test target is adjusted based in part on the user's response to the fixation task;
    (d). determining whether the user has detected the first test target at the first location based on an analysis of user input; and
    (e). collecting, based on the user input, data related to the determining of whether the user has detected the first test target at the first location;
    automatically iteratively performing (a)-(e) for each of a subset of the plurality of fixation targets and corresponding ones of the plurality of test targets until a certain termination condition is met, and
    providing information related to a result of the visual field assessment of the user based at least on the collected data from the iterative performance of (a)-(e).

9. The method of claim 8, wherein the analysis of the user input comprises determining whether the user input indicates that the pointer is moving towards the first location.

10. The method of claim 8, wherein the analysis of the user input comprises determining whether the user input indicates that a head of the user is moving towards the first location.

11. The method of claim 8, further comprising:
displaying, at a second location on the virtual reality environment that is different from the first location, a second test target of the plurality of test targets.

12. The method of claim 8, wherein the first fixation target is displayed in vicinity of the first location.

13. The method of claim 8, further comprising:
based at least on determining that the fixation task associated with the first fixation target is not completed, modifying one or more properties associated with the first fixation target until the fixation task is completed.

14. The method of claim 8, wherein the first fixation target and the first test target are associated with a plurality of display properties to ensure that it requires foveal vision of the user to complete the fixation task and the first test task, wherein the plurality of display properties comprise size, luminance, contrast, and moving speed.

15. A non-transitory computer-readable medium for assessment of a visual field of a user, storing instructions, which when executed by at least one data processor, result in operations comprising:
(a). displaying, on a virtual reality environment on a virtual reality display of a head-mountable virtual reality device, a first fixation target, the virtual reality environment comprising a pointer that is controlled by a user wearing the head-mountable virtual reality device, the first fixation target being one of a plurality of fixation targets;
(b). determining whether a fixation task associated with the first fixation target has been completed by the user, wherein the fixation task is completed when the pointer overlaps at least a portion of the first fixation target, and wherein the first fixation target is configured such that it requires foveal vision of the user to complete the fixation task;
(c). in response to that the fixation task is completed, displaying, on the virtual reality display, a first test target at a first location, wherein the first test target is configured such that it requires the foveal vision of the user to complete a first test task, the first test target being one of a plurality of test targets, wherein a set of display properties of the first test target is adjusted based in part on the user's response to the fixation task;
(d). determining whether the user has detected the first test target at the first location based on an analysis of user input;
(e). collecting, based on the user input, data related to the determining of whether the user has detected the first test target at the first location; and
automatically iteratively performing (a)-(e) for each of a subset of the plurality of fixation targets and corresponding ones of the plurality of test targets until a certain termination condition is met, and
providing information related to a result of the visual field assessment of the user based at least on the collected data from the iterative performance of (a)-(e).

16. The non-transitory computer-readable medium of claim 15, wherein the analysis of the user input comprises determining whether the user input indicates that the pointer is moving towards the first location.

17. The non-transitory computer-readable medium of claim 15, wherein the analysis of the user input comprises determining whether the user input indicates that a head of the user is moving towards the first location.

18. The non-transitory computer-readable medium of claim 15, the operations further comprise:
displaying, at a second location on the virtual reality environment that is different from the first location, a second test target of the plurality of test targets.

19. The non-transitory computer-readable medium of claim 15, the operations further comprise:
based at least on determining that the fixation task associated with the first fixation target is not completed, modifying one or more properties associated with the first fixation target until the fixation task is completed.

20. The non-transitory computer-readable medium of claim 15, wherein the first fixation target and the first test target are associated with a plurality of display properties to ensure that it requires foveal vision of the user to complete the fixation task and the first test task, wherein the plurality of display properties comprise size, luminance, contrast, and moving speed.

* * * * *